(12) United States Patent
Hubbell et al.

(10) Patent No.: US 11,484,599 B2
(45) Date of Patent: Nov. 1, 2022

(54) POLYMER CONJUGATE VACCINES

(71) Applicant: The University of Chicago, Chicago, IL (US)

(72) Inventors: Jeffrey A. Hubbell, Chicago, IL (US); David Scott Wilson, Chicago, IL (US); Sachiko Hirosue, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 15/764,366

(22) PCT Filed: Sep. 29, 2016

(86) PCT No.: PCT/US2016/054315
§ 371 (c)(1),
(2) Date: Mar. 29, 2018

(87) PCT Pub. No.: WO2017/058996
PCT Pub. Date: Apr. 6, 2017

(65) Prior Publication Data
US 2018/0280524 A1    Oct. 4, 2018

Related U.S. Application Data

(60) Provisional application No. 62/234,352, filed on Sep. 29, 2015.

(51) Int. Cl.
*A61K 47/58* (2017.01)
*A61K 39/015* (2006.01)
(Continued)

(52) U.S. Cl.
CPC .......... *A61K 47/58* (2017.08); *A61K 31/787* (2013.01); *A61K 39/015* (2013.01);
(Continued)

(58) Field of Classification Search
CPC ...... C08F 8/00; C08F 220/56; C08F 2438/03; C07D 471/04; A61K 35/00; A61P 33/06;
(Continued)

(56) References Cited

U.S. PATENT DOCUMENTS 6,651,655 B1    11/2003  Licalsi et al.
2003/0187016 A1  10/2003  Crooks et al.
(Continued)

FOREIGN PATENT DOCUMENTS

CN         1479738        3/2004
CN       101861165       10/2010
(Continued)

OTHER PUBLICATIONS

Du, Jun, et al. "TLR8 agonists stimulate newly recruited monocyte-derived cells into potent APCs that enhance HBsAg immunogenicity." Vaccine 28.38 (2010): 6273-6281.*
(Continued)

*Primary Examiner* — Isaac Shomer
*Assistant Examiner* — Amanda Michelle Petritsch
(74) *Attorney, Agent, or Firm* — Norton Rose Fulbright US LLP

(57) ABSTRACT

Monomers and copolymers are provided that both target antigen presenting cells (APCs) and activate toll-like receptor (TLR) on the APCs. In some embodiments, compositions and methods involve a polymer that targets the mannose receptor on APCs, in addition to activating a TLR. These can then be conjugated to protein antigens to efficiently target antigens to DCs and simultaneously induce the up-regulation of co-stimulatory molecules that are essential for effective T cell activation. This copolymer is a more efficient activator of DCs, as measured by the surface expression of co-stimulatory molecules and the release of proinflammatory cytokines, than the monomeric form the TLR agonist
(Continued)

used in the polymer formulation. Aspects of the disclosure relate to novel compounds, methods, and compositions for treating diseases using the compounds, copolymers, and compositions described herein.

16 Claims, 25 Drawing Sheets

Specification includes a Sequence Listing.

(51) Int. Cl.
*A61K 39/39* (2006.01)
*A61K 31/787* (2006.01)
*A61K 47/54* (2017.01)
*C08F 8/00* (2006.01)
*C07D 471/04* (2006.01)
*A61P 35/00* (2006.01)
*A61P 33/06* (2006.01)
*A61K 39/145* (2006.01)
*C08F 220/56* (2006.01)
*A61K 39/00* (2006.01)

(52) U.S. Cl.
CPC ............ *A61K 39/145* (2013.01); *A61K 39/39* (2013.01); *A61K 47/549* (2017.08); *A61P 33/06* (2018.01); *A61P 35/00* (2018.01); *C07D 471/04* (2013.01); *C08F 8/00* (2013.01); *C08F 220/56* (2013.01); *A61K 2039/5154* (2013.01); *A61K 2039/55516* (2013.01); *A61K 2039/55561* (2013.01); *A61K 2039/55572* (2013.01); *A61K 2039/55577* (2013.01); *A61K 2039/55583* (2013.01); *A61K 2039/572* (2013.01); *A61K 2039/575* (2013.01); *A61K 2039/6087* (2013.01); *A61K 2039/6093* (2013.01); *A61K 2039/627* (2013.01); *C08F 2438/03* (2013.01)

(58) Field of Classification Search
CPC .... A61K 47/58; A61K 31/787; A61K 39/015; A61K 39/145; A61K 39/39; A61K 47/549; A61K 2039/5154; A61K 2039/55516; A61K 2039/55561; A61K 2039/55572; A61K 2039/55577; A61K 2039/55583; A61K 2039/572; A61K 2039/575; A61K 2039/6087; A61K 2039/6093; A61K 2039/627
See application file for complete search history.

(56) References Cited

U.S. PATENT DOCUMENTS

| 2007/0166384 A1* | 7/2007 | Zarraga ............ A61K 31/4745 424/486 |
| 2009/0081157 A1 | 3/2009 | Kornbluth et al. |
| 2012/0294885 A1 | 11/2012 | David et al. |
| 2014/0256922 A1 | 9/2014 | David et al. |
| 2015/0050313 A1 | 2/2015 | Mancini et al. |
| 2015/0110742 A1 | 4/2015 | Spiegel et al. |

FOREIGN PATENT DOCUMENTS

| CN | 103582640 | 2/2014 | |
| WO | WO 00/76505 | 12/2000 | |
| WO | WO 02/46193 | 6/2002 | |
| WO | WO 2006/009832 | 1/2006 | |
| WO | WO 2006/028545 | 3/2006 | |
| WO | WO 2006/029115 | 3/2006 | |
| WO | WO 2009/051837 | 4/2009 | |
| WO | WO 2012/167081 | 12/2012 | |
| WO | WO-2013166110 A1 * | 11/2013 | ............ A61K 31/53 |

OTHER PUBLICATIONS

Entry for "2-(ethoxymethyl)-1h-Imidazo[4,5-C]quinolin-4-Amine (CL-097)" in PubChem [online], retrieved from the internet on (Feb. 1, 2020) from URL<https://pubchem.ncbi.nlm.nih.gov/compound/11579618>.*
International Search Report and Written Opinion Issued in Corresponding PCT Application No. PCT/US2016/54315, dated Dec. 29, 2016.
Extended European Search Report issued in Corresponding Application No. 16852545.9, dated May 28, 2020.
Office Action issued in Corresponding Chinese Application No. 201680069873.5, dated Sep. 17, 2020 (English Translation provided).

* cited by examiner

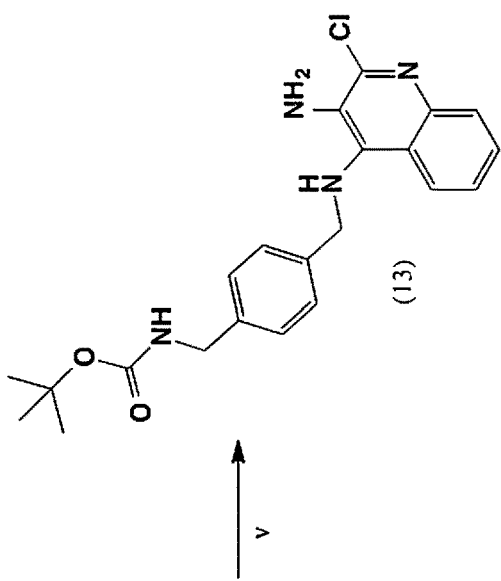
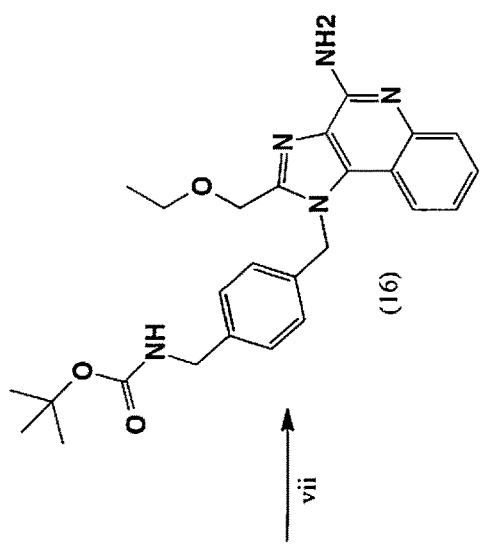
FIG. 1
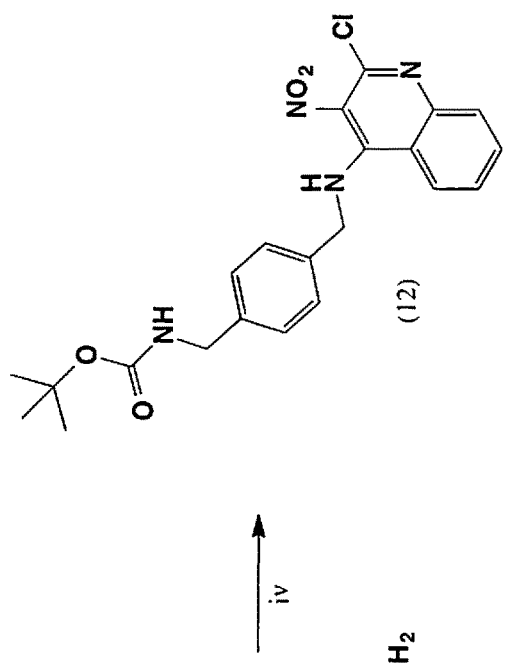
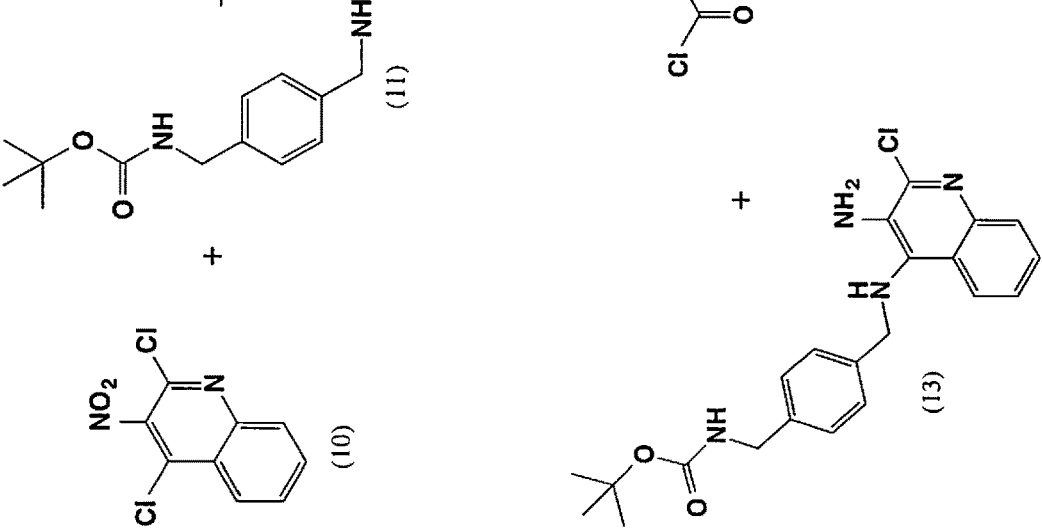
FIG. 2

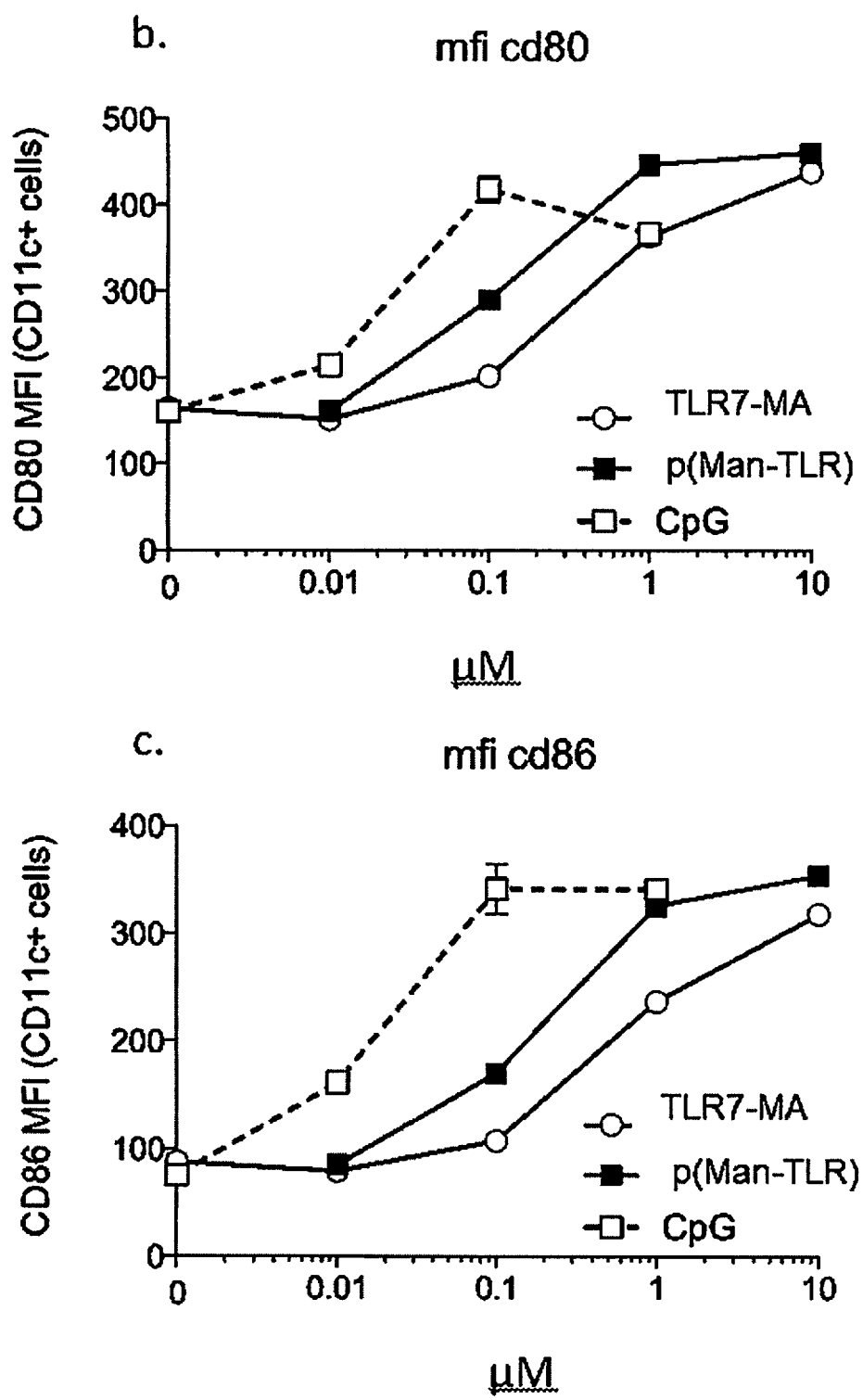
FIG. 8B-C

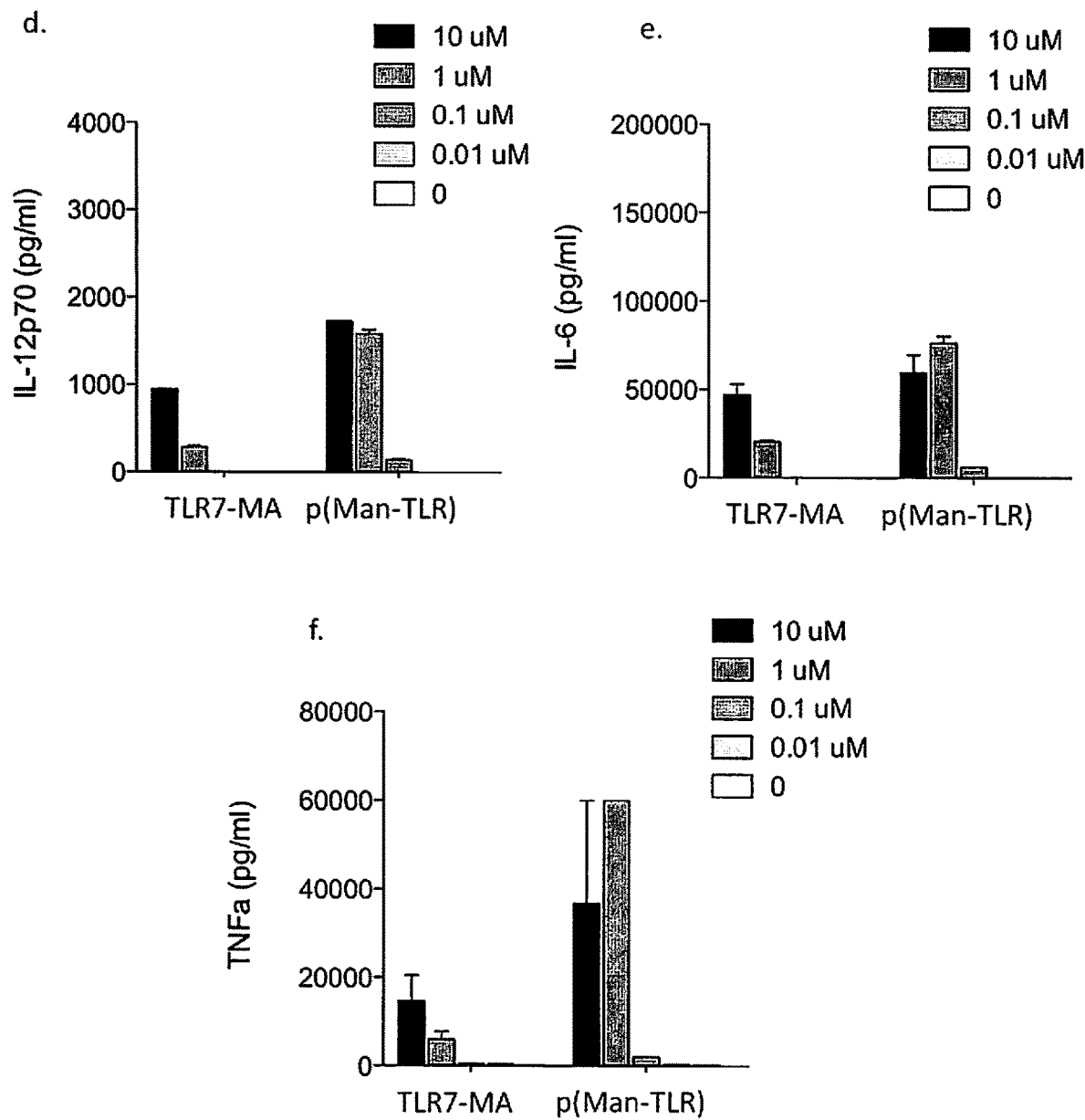
FIG. 8D-F

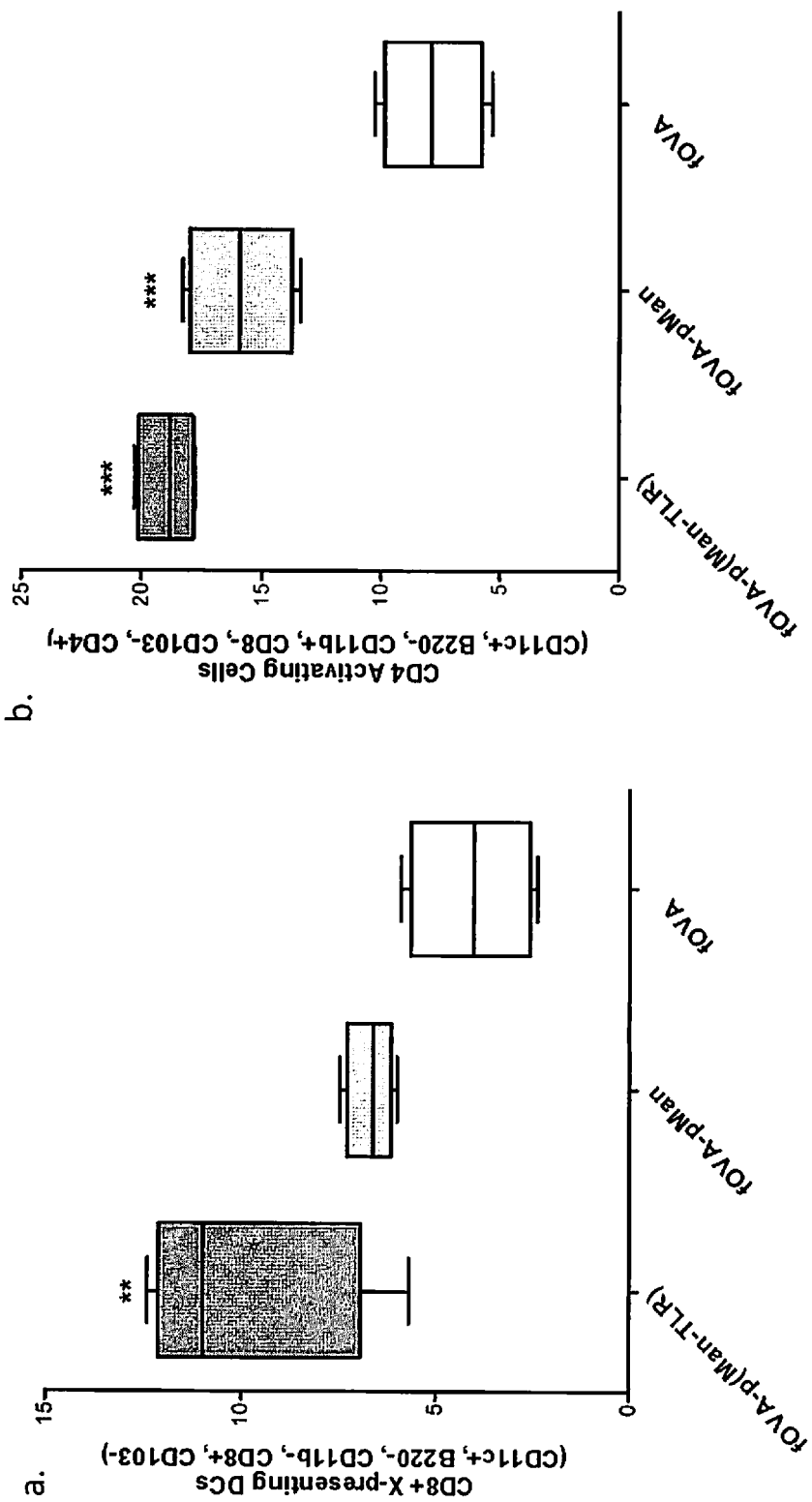
FIG. 9A-B

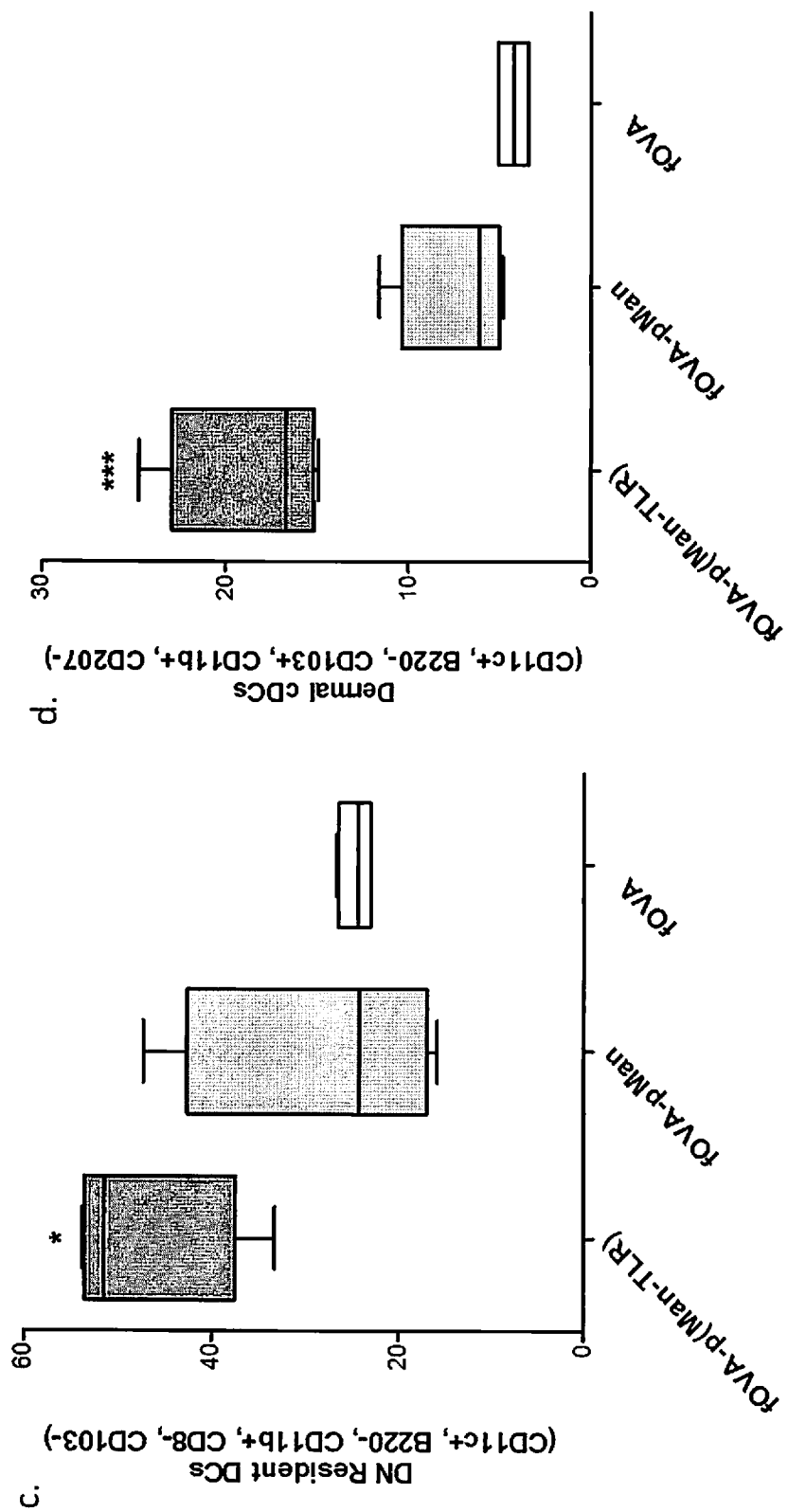
FIG. 9C-D

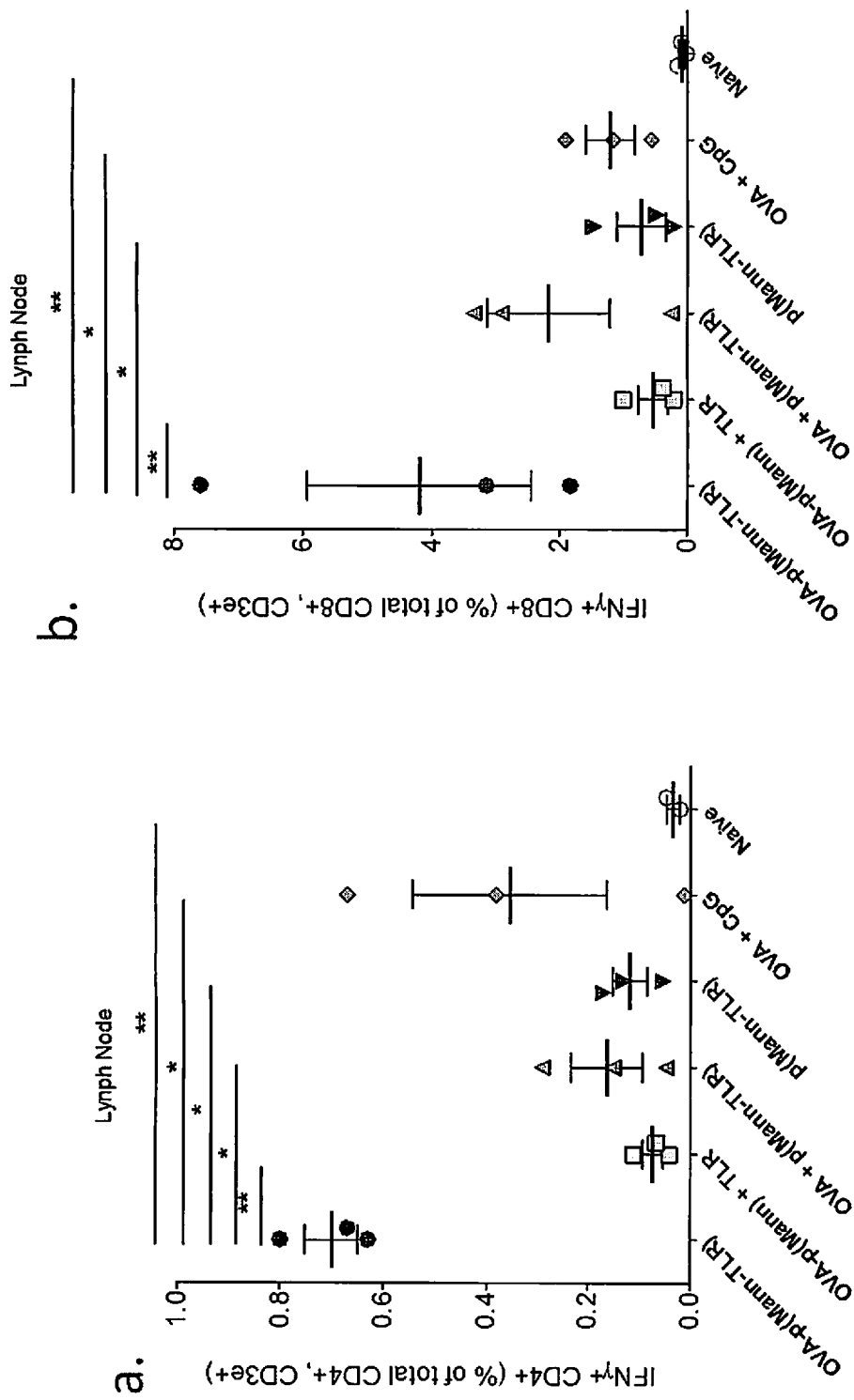
FIG. 10A-B

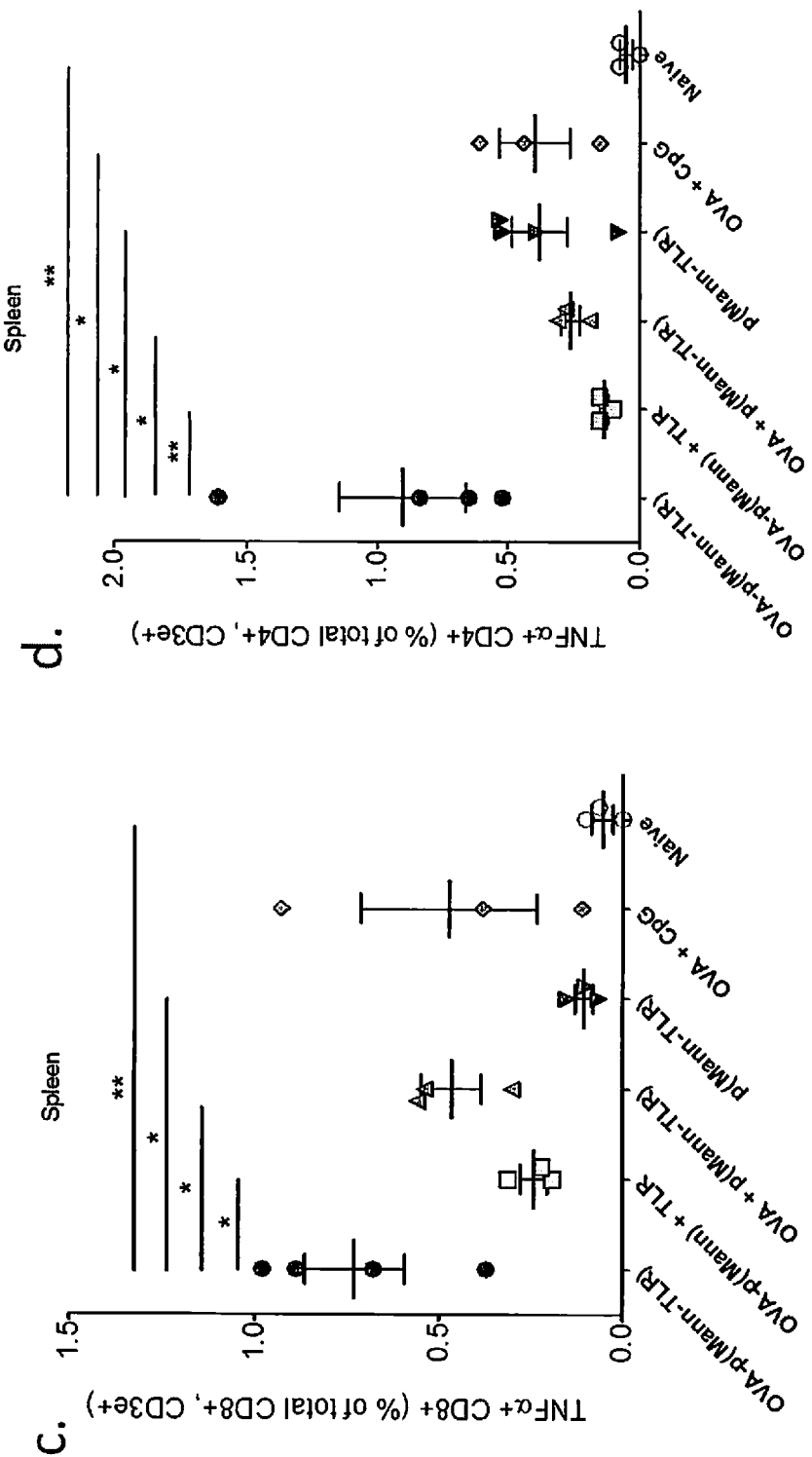
FIG. 10C-D

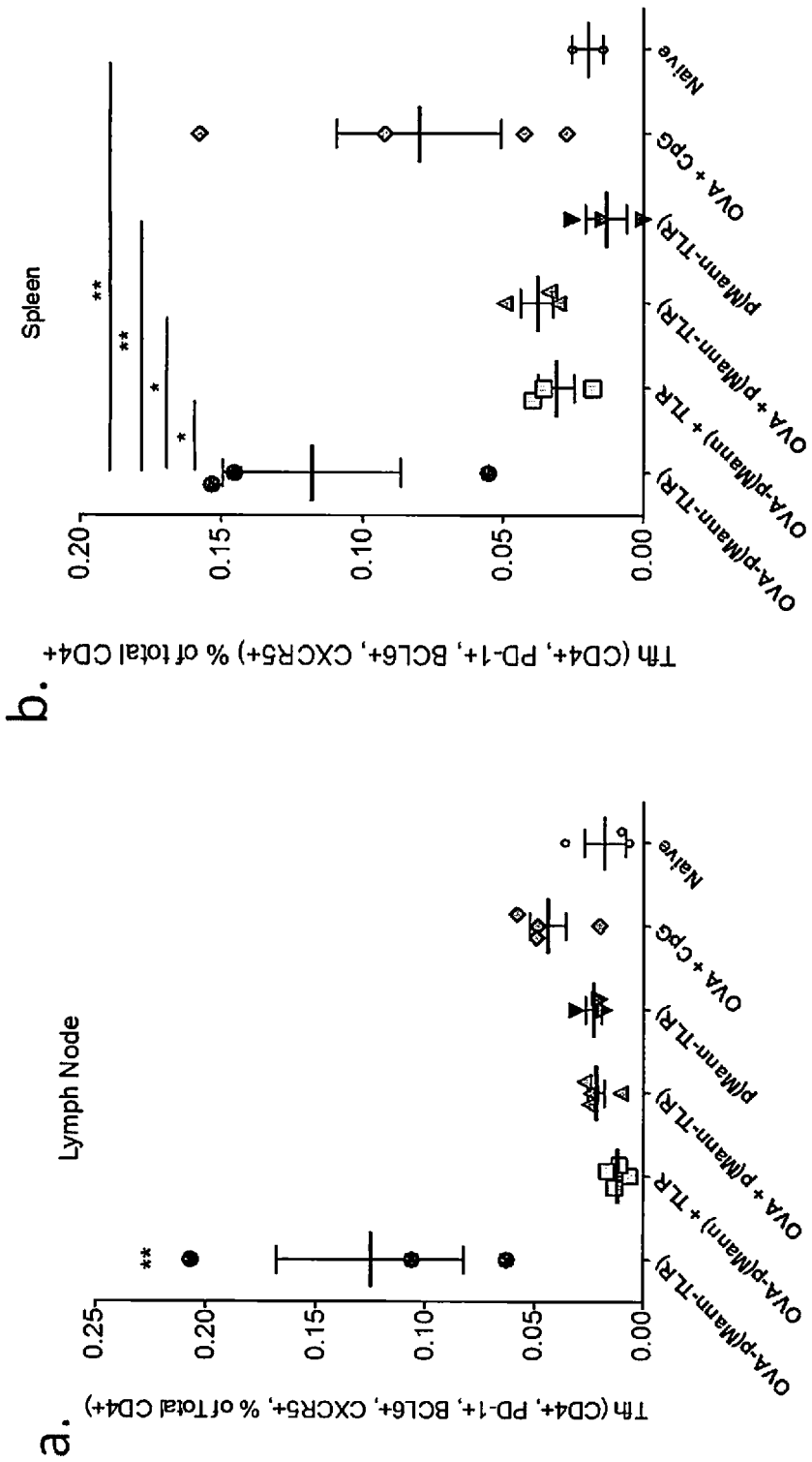
FIG. 11A-B

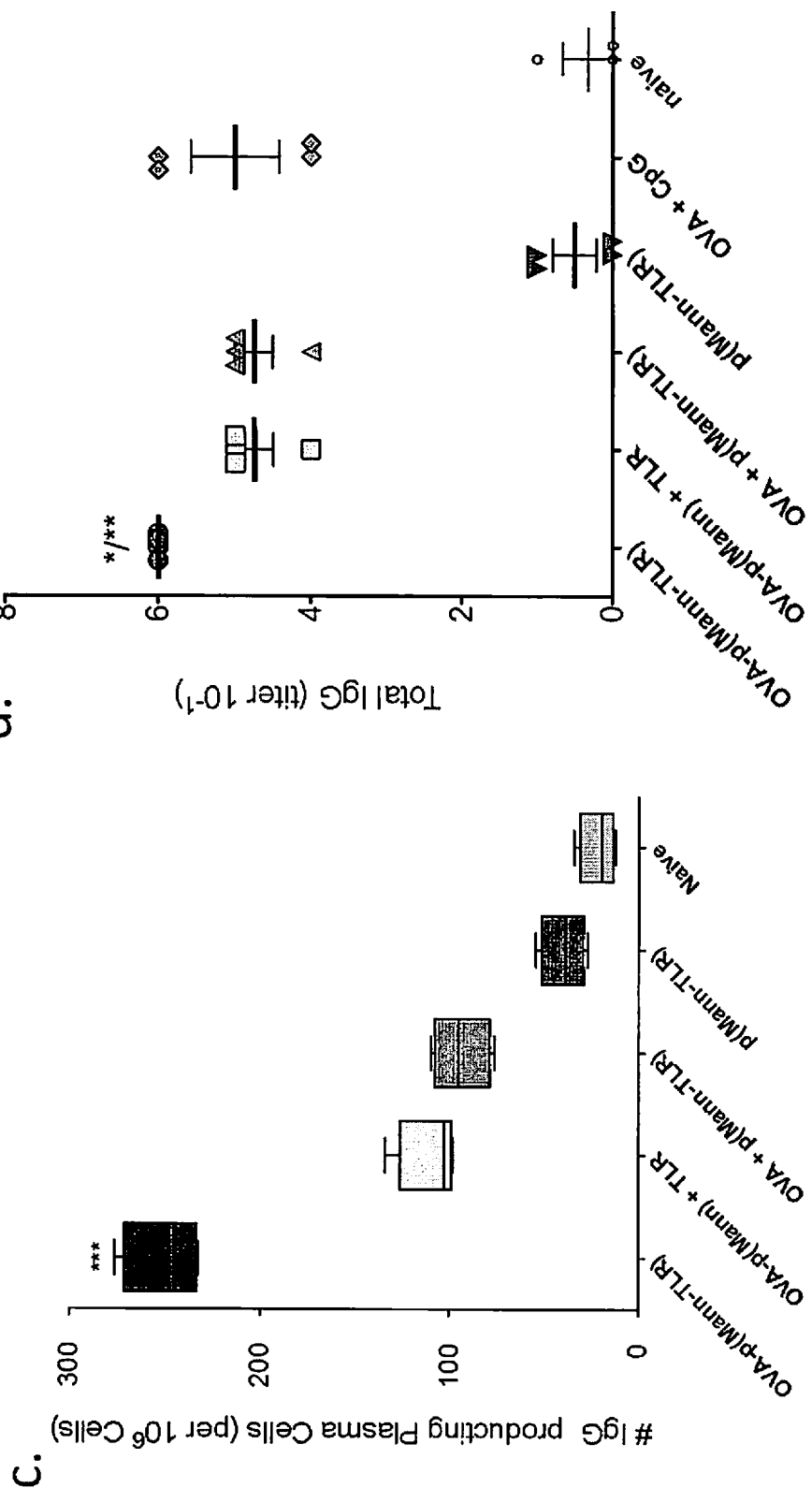
FIG. 11C-D

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Ser Ile Ile Asn Phe Glu Lys Leu
1               5
```

POLYMER CONJUGATE VACCINES

CROSS-REFERENCE TO RELATED APPLICATIONS

This application claims the benefit of priority of U.S. Provisional Patent Application No. 62/234,352, filed Sep. 29, 2015, which is hereby incorporated by reference in its entirety.

BACKGROUND OF THE INVENTION

1. Field of the Invention

The present invention relates generally to the field of medicine. More particularly, it concerns toll-ligand receptor (TLR) agonists-antigen presenting cell (APC) targeting molecules that are conjugated with antigens to increase antigen uptake and activation in dendritic cells (DC).

2. Background

The two major challenges in the development of effective subunit vaccines are the ability to target unmodified recombinant protein antigens to dendritic cells (DCs) and the identification of nontoxic DC-activating adjuvants that effectively enhance the immune response to targeted antigens. Targeting antigens to surface receptors on professional antigen-presenting cells (APCs) represents an attractive method for improving antigen presentation by APCs and thus the efficacy of subunit vaccines. Delivery strategies that target antigens to APCs preferably target receptors that are abundantly expressed on the surface of APCs as well as release these antigens in their native form in intracellular compartments that contain elements of the antigen-processing machinery. The mannose receptor (MR) and other C-type lectin receptors are abundant on APCs and designed to internalize antigens, process them and display the internalized antigen on both major histocompatibility complex (MHCI and MHCII) molecules. Although targeting the MR on APCs, specifically dendritic cells (DCs), increases antigen presentation and immune response to those antigens, it is clear that additional signals, in the form of cell-activating adjuvants, are preferably combined with MR-targeting strategies for the induction of a robust sustained immune response.

The inclusion of adjuvants in subunit vaccine formulations can improve vaccine-induced protection by inducing the maturation of immature DCs, which results in the production and surface expression of proinflammatory and co-stimulatory molecules that are necessary for T cell polarization. DC activation is initiated via toll-like receptors (TLRs), which recognize pathogen-associated molecular patterns that are specific to infectious agents. Recent vaccine development has focused on incorporating TLR ligands, such as bacterial and viral DNA, bacterial proteins, and synthetic small-molecules, into the formulation of subunit vaccines. Given their relative ease of production and low toxicity, small molecule TLR-7 and TLR-8 ligands known as imidazoquinolines overcome some of the challenges of using viral and bacterial-derived material as vaccine adjuvants. However, the hydrophobicity and relatively low activity of current imidazoquinolines limit their use in vaccine formulations, and thus the design of more effective imidazoquinolines and new strategies for their delivery are greatly needed.

SUMMARY OF THE INVENTION

This disclosure fulfills the aforementioned need in the art by providing novel TLR molecules and a novel copolymer composed of a monomer that targets the mannose receptor (MR) on APCs and a second monomer that serves as an adjuvant by activating toll-like receptor. These can then be conjugated to protein antigens to efficiently target antigens to DCs and simultaneously induce the up-regulation of co-stimulatory molecules that are essential for effective T cell activation. As shown in the examples of the application, this copolymer is a more efficient activator of DCs, as measured by the surface expression of co-stimulatory molecules and the release of pro-inflammatory cytokines, than the monomeric form of the TLR agonist used in the polymer formulation. Aspects of the disclosure relate to novel compounds, methods, and compositions for treating disease.

In one embodiment there is disclosed a copolymer having the structure (I):

where A includes at least one group that binds an Antigen Presenting Cell (APC) mannose receptor; Z includes at least one Toll-Like Receptor (TLR) agonist; W and Y, are each independently a polymerized monomer unit of a polymer; m is from 1 to 100000, from 5 to 50000, from 5 to 10000, from 5 to 1000, from 10 to 500. In some embodiments, m is from 10 to 150, and p is from 1 to 100000, from 1 to 50000, from 1 to 10000, from 1 to 1000, from 1 to 100, from 1 to 50, and from 1 to 20. It is understood that m and p are integers. In one aspect A is a mannose-containing compound that can be derived from mannose and N-(2-hydroxyethyl)methacrylamide. In another aspect of copolymer (I), Z has the general structure (II):

where X is a linker bonded to the TLR agonist and Y. X can be a heteroatom, an aliphatic group, a substituted aliphatic group, an alkoxy group, a heteroalkyl group, a substituted heteroalkyl group, an aryl group, a substituted aryl group, a benzyl group, a substituted benzyl group, a heteroaryl group, a substituted heteroaryl group, any combination thereof or a covalent bond. In a particular aspect, the TLR agonist is a TLR7 agonist, a TLR8 agonist, a TLR7/8 agonist, or any combination thereof and the TLR agonist has the general structure (III):

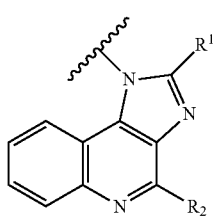

(III)

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, a substituted aryl group, a heteroaryl group, a substituted heteroaryl group, an alkoxy group, an alkoxyalkyl group, an alkoxyalkoxy group, and alkoxyalkoxyalkyl group, an amino group, or a hydroxyl group. In one aspect, $R_2$ is a free amine (—$NH_2$) and $R_1$ is an alkyl group or an alkoxy group, and preferably the alkoxyalkyl group is ethoxymethyl (—$CH_2OCH_2CH_3$). In one example, Z is:

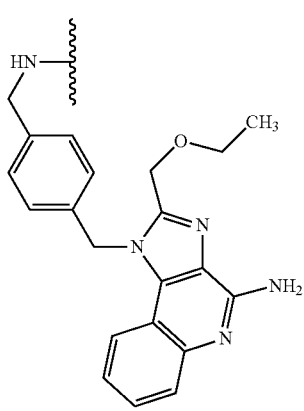 [SMILES: *NCc1ccc(Cn2c(COCC)nc3c(N)nc4ccccc4c32)cc1]

In another example, Z is:

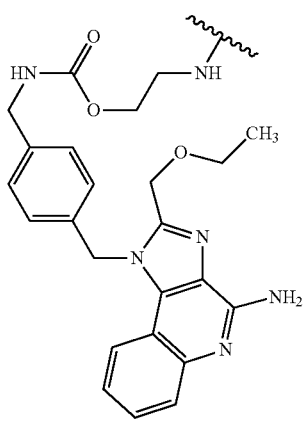 [SMILES: *NCCOC(=O)NCc1ccc(Cn2c(COCC)nc3c(N)nc4ccccc4c32)cc1]

In another aspect, a TLR agonist of structure (III) is disclosed, where $R_2$ is a free amine (—$NH_2$) and $R_1$ is a $C_1$-$C_6$ alkyl group, preferably n-butyl. In one example, Z is:

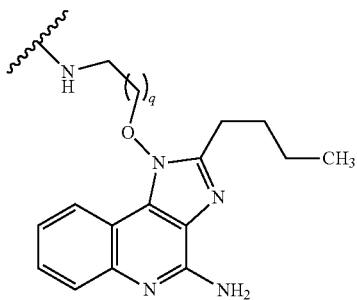

where q is from about 1 to 100, from about 1 to 50, or from about 2 to 20, and preferably from about 2 to 9.

In another embodiment, the copolymer includes end units, wherein the end units are each independently a residue of the polymer, a linker, an immunomodulating agent, or combinations thereof, and the copolymer has the general structure (IV):

where E and Q are end units, wherein E and Q are each independently a residue of the polymer, a linker, an immunomodulating agent, or any combination thereof. In one aspect, at least one of E or Q is at least one linker. The linker can be an azide containing linker. The azide containing linker can be formed from:

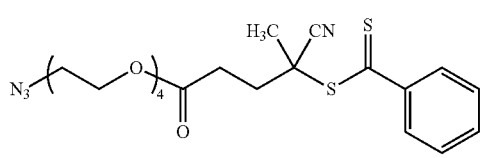

In another aspect, E or Q is an immunomodulating agent and the immunomodulating agent is an antigen, a TLR agonist, or any combination thereof. In certain aspects, the immunomodulating agent is an antigen covalently attached to the polymer by a linker, wherein the linker is a self-immolating linker and the linker is formed from:

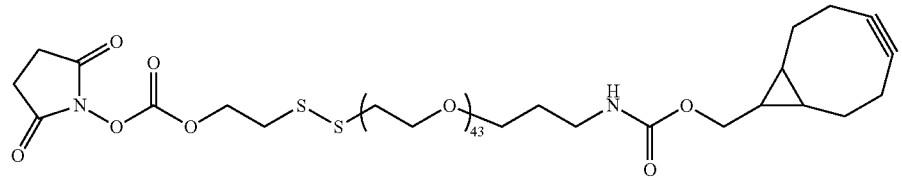

In yet another aspect, W and Y are each independently polymerized monomeric units of a polyacrylate, such as poly(acrylic acid) or poly(methacrylic acid) or poly(hydroxypropyl methacrylate), a polyacrylamide, a saturated polyolefin, a polyamide, such as poly(acrylamide) or poly(methacrylamide), a peptide, a polypeptide, an unsaturated olefin formed by ring opening metathesis polymerization, a siloxane, a polysiloxane, a polyether, a polysaccharide, a polyoxazoline, such as poly(ethyloxazoline), a polyimine, such as poly(ethylenimine), a polyvinyl derivative, such as poly(vinyl alcohol) and poly(vinylpyrrolidone), or any combination thereof, and copolymer (I) is:

where q is from 1 to 100, from 1 to 50, from 2 to 20, and from 2 to 9. In one example, Ri is n-butyl or ethoxymethyl (—CH2OCH2CH3) and R2 is a free amine (—NH2). The ratio of p:m for copolymer (I) as described herein ranges from about 10:90 to about 20:80 and any range therebetween, including 11:89, 12:88, 13:87, 14:86, 15:85, 16:84, 17:83, 18:82, and 19:81, preferably about 16:84. The average molecular weight ranges from about 30 to about 80 kDa and any weight therebetween, including about 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65,

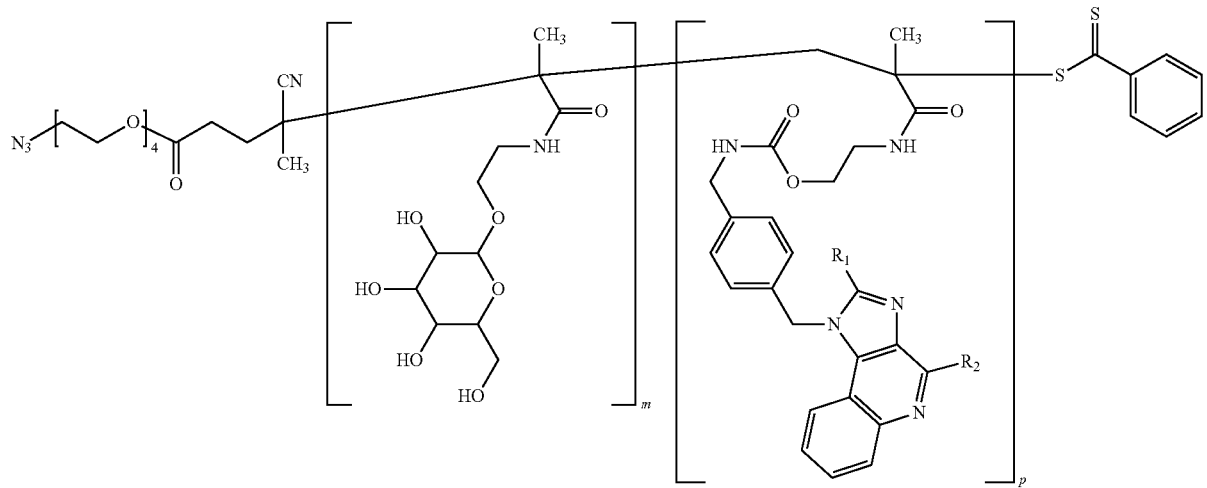

In one example, $R_1$ is ethoxymethyl (—CH$_2$OCH$_2$CH$_3$) and $R_2$ is a free amine (—NH$_2$). In another example, copolymer (I) is:

66, 67, 68, 69, 70, 71, 72, 73, 74, 75, 76, 77, 78, and 79, (and any range derivable therein); in one embodiment the average molecule weight is about 34 kDa.

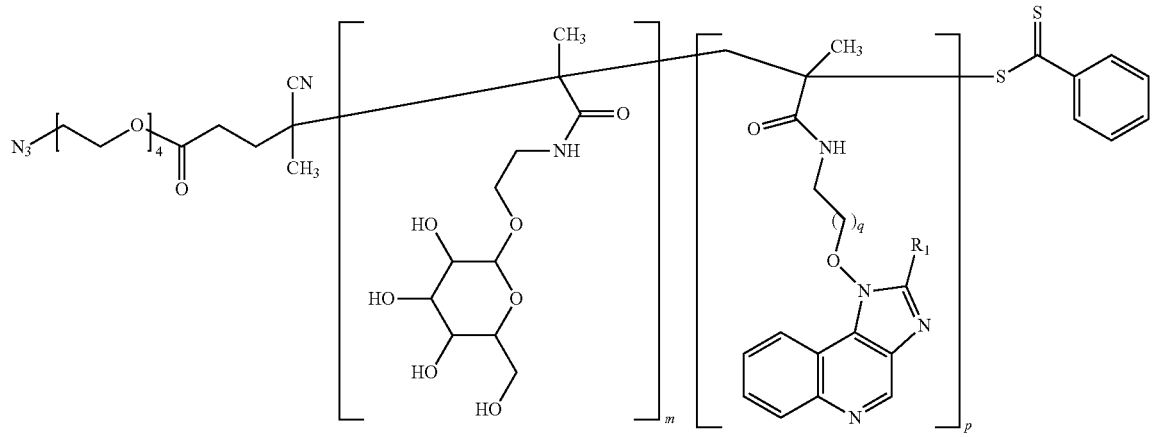

In some embodiments, copolymer (I) can further include a repeating unit (V):

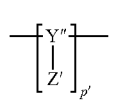

(V)

where Y" is a polymerized monomer unit of a polymer bonded to W or Y; Z' comprises at least one TLR agonist; and p' is from 1 to 100000, from 1 to 50000, from 1 to 10000, from 1 to 1000, from 1 to 100, from 1 to 50, and in specific embodiments, p' is from 1 to 20. Y' can be a polymerized monomer unit of polyacrylate, such as poly(acrylic acid) or poly(methacrylic acid) or poly(hydroxypropyl methacrylate), a polyacrylamide, a saturated polyolefin, a polyamide, such as poly(acrylamide) or poly(methacrylamide), a peptide, a polypeptide, an unsaturated olefin formed by ring opening metathesis polymerization, a siloxane, a polysiloxane, a polyether, a polysaccharide, a polyoxazoline, such as poly(ethyloxazoline), a polyimine, such as poly(ethylenimine), a polyvinyl derivative, such as poly(vinyl alcohol) and poly(vinyl pyrrolidone), or any combination thereof.

Also disclosed herein are compositions that include the copolymers as described above. In one embodiment, the compositions further include an antigen and the antigen can be operatively linked to copolymer (I), (IV), or (V). Alternatively the antigen can be covalently linked to the compound by a linker or non-covalently linked to the polymer. In some aspects of the composition, the antigen is covalently linked to the copolymer using a bifunctional linker having functional groups selected from amines, azides, alkynes, and N-succinimidyl carbonates. In a particular aspect, the linker is a self-immolating linker and can be formed from:

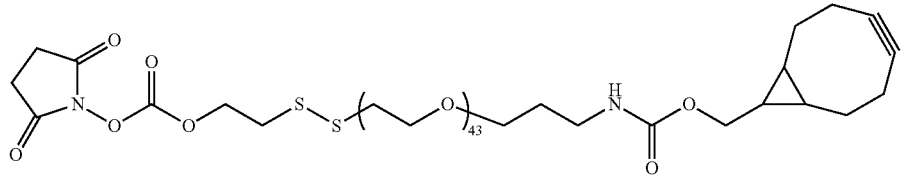

Also disclosed are methods for inducing the immune system, the methods can include administering the aforementioned copolymers and compositions. These methods also include preventing or treating an infection. The methods described herein may also be used to treat or prevent diseases such as, for example, cancer, infectious diseases described herein, and autoimmune diseases. Methods are provided to induce a specific immune response against one or more antigens included in a monomer or polymer.

Further, the methods described herein may be used to vaccinate subjects for certain diseases. In certain embodiments, the methods include multiple administrations of the composition. The administrations may be days, weeks, months, years, or decades apart. The compositions including the conjugate described herein may be administered orally, intravenously, subcutaneously, intradermally, intramuscularly, intranasally, by injection, by inhalation, mucosally, and/or by using a nebulizer.

In one embodiment of the methods described herein, the subject is a human subject. The term "subject," "individual" or "patient" is used interchangeably herein and refers to a vertebrate, for example a primate, a mammal or a human. Mammals include, but are not limited to equines, canines, bovines, ovines, murines, rats, simians, humans, farm animals, sport animals and pets.

In other embodiments, there is disclosed a monomer having a general structure of (VI):

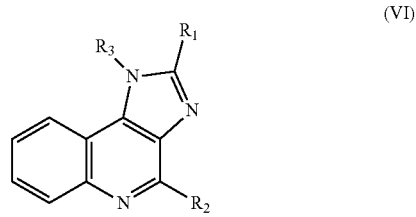

(VI)

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, a substituted aryl group; and $R_3$ is a ligand comprising a polymerizable group Y'. In one example, $R_2$ is a free amine (—$NH_2$) and $R_1$ is an alkyl group or an alkoxy group, preferably $R_1$ is a $C_1$ to $C_6$ alkyl group or a n-butyl group or alternatively $R_1$ is an ethoxymethyl group (—$CH_2OCH_2CH_3$). In another example, $R_3$ further contains a heteroatom, an aliphatic group, a substituted aliphatic group, an alkoxy group, a heteroalkyl group, a substituted heteroalkyl group, an aryl group, a substituted aryl group, a benzyl group, a substituted benzyl group, a heteroaryl group, or a substituted heteroaryl group. In one embodiment, $R_3$ has the general structure of

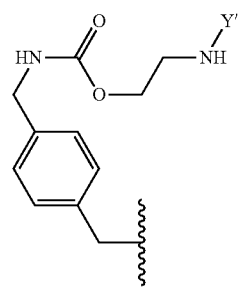

In one aspect, Y' includes an olefin and the monomer (VI) is:

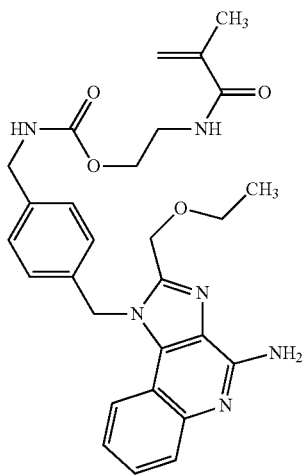 [SMILES: C=C(C)C(=O)NCCOC(=O)NCc1ccc(Cn2c(COCC)nc3c(N)nc4ccccc4c32)cc1]

In another embodiment monomer (VI) has the general structure of:

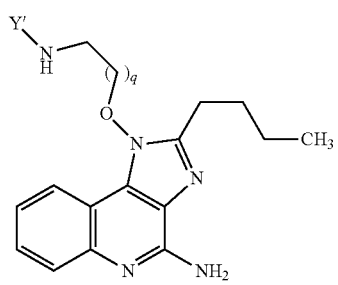

where q is from 1 to 100, from 1 to 50, from about 2 to 20, or from 2 to 9. In one aspect, Y' contains an olefin and the monomer (VI) is:

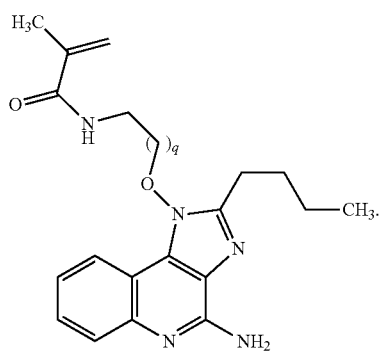

In some embodiments, a copolymer containing monomer (VI) is disclosed. The copolymer can further include a second monomeric unit, where the second monomeric group includes at least one group that binds to an APC mannose receptor coupled to a polymerizable group. In this instance, the copolymer has a general structure of (VII):

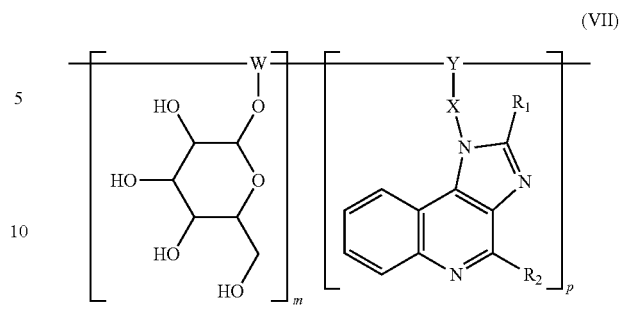

where W is a polymerized monomeric unit of a polymer backbone; Y is a polymerized monomeric unit of the polymerizable group Y'; m is from 1 to 100000, from 5 to 50000, from 5 to 10000, from 5 to 1000, from 10 to 500, or from 10 to 150, and p is from 1 to 100000, from 1 to 50000, from 1 to 10000, from 1 to 1000, from 1 to 100, from 1 to 50, or from 1 to 20. In a particular aspect, W is a derivative of derivative of N-(2-hydroxyethyl)methacrylamides. Copolymer (VII) may further contain an antigen and the antigen can be covalently bound to the copolymer.

In other embodiments, a polymer formed from monomer (VI) is disclosed.

The polymer is formed via the polymerization of Y' and the polymer comprises a general structure of (VIII):

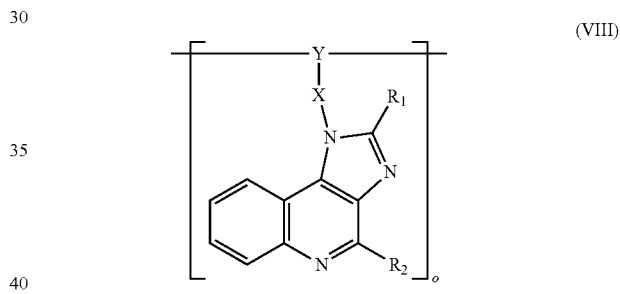

where o is from 2 to 100000, from 2 to 50000, from 2 to 10000, from 2 to 1000, from 2 to 100, from 2 to 50, or from 2 to 20, and Y is the product of polymerizing Y'. In one instance polymer (VIII) comprises:

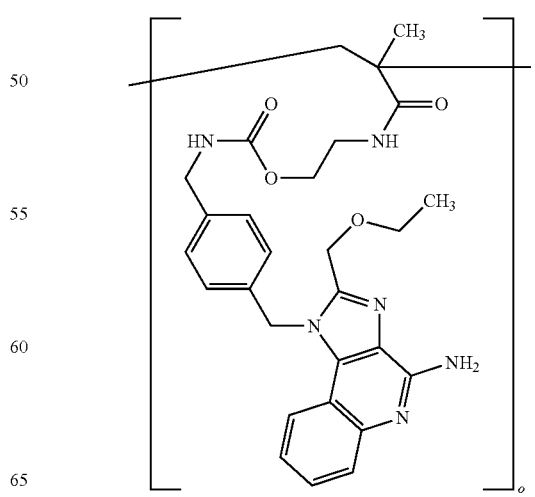

In another instance polymer (VIII) is:

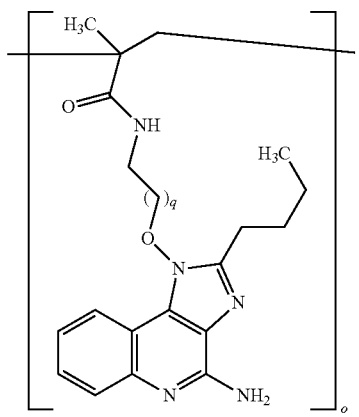

where q is from 1 to 100, from 1 to 50, from 2 to 20, or from 2 to 9. In one aspect, polymer (VIII) can be operatively linked to an APC-targeting molecule and the APC-targeting molecule can be a mannose-containing compound. In a particular aspect, polymer (VIII) is covalently linked to the mannose-containing compound and the mannose-containing compound is derived from mannose and N-(2-hydroxyethyl) methacrylamide. Polymer (VIII) can also be covalently linked to the mannose-containing compound to form a copolymer and the copolymer has the general structure of (VII):

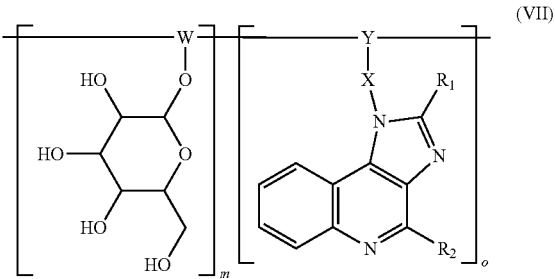

where W is a polymerized monomeric unit; and m is from 1 to 100000, from 5 to 50000, from 5 to 10000, from 5 to 1000, from 10 to 500, or from 10 to 150. Polymer (VII) may also further include an antigen and the antigen may be covalently bound. In a further aspect, any of the copolymers described above may be a block copolymer, an alternating copolymer or a random copolymer.

Methods of making a monomers, copolymers, and polymer are described herein. In some embodiments, the monomers are prepared by stepwise 2,4-dihalo-3-nitroquinolone nucleophilic aromatic substitution reactions, nitro reduction, imidazole heteroannulation, and amidation using protective group manipulation. In other embodiments, the copolymers and polymers are prepared by radical polymerization and antigen conjugation is accomplished by carbonate amidation and 1,3-dipolar cycloaddition reactions. Non-limiting examples of making the monomers, copolymers, and polymers of the present invention are provided in the Examples section.

Further embodiments relate to vaccine compositions comprising the copolymers, compositions, monomers, or polymers described herein. The vaccine composition may also comprise a pharmaceutically acceptable carrier and/or any further pharmaceutical ingredient described herein.

The use of the words "a" or "an" when used in conjunction with any of the terms "comprising," "including," "containing," or "having," in the claims or the specification may mean "one," but it is also consistent with the meaning of "one or more," "at least one," and "one or more than one.".

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows a reaction schematic for the preparation of tert-butyl (4-(((3-amino-2-chloroquinolin-4-yl)amino) methyl)benzyl)carbamate (13).

FIG. 2 shows a reaction schematic for the preparation of (4-((amino-2-(ethoxymethyl)-1H-imidazo[4,5-c]quinolin-1-yl)methyl)benzyl)carbamate (16).

FIGS. 8A-F shows graphical data demonstrating that p(Man-TLR) is a more of a TLR7 agonist than monomeric TLR7 agonist and induces surface expression of co-stimulatory molecules and release of proinflammatory cytokines by BMDCs. a. HEK-Blue TLR7 reporter cells were treated with either p(Man-TLR) (4), TLR7-MA (3), or the commercially available TLR-7 agonist Gardiquimod for 12 h. p(Man-TLR) is a more efficient ligand for TLR7 as compared to an equal amount of unpolymerized monomer. b,c. BMDCs were treated for 6 h with various concentrations of p(Man-TLR), TLR7-MA, or CpG. Cells were analyzed for the surface expression of the co-stimulatory molecules CD80 (b) and CD86 (c). p(Man-TLR) induces increased surface expression of the co-stimulatory molecules CD80 and CD86. d-f. BMDCs were treated with various concentrations of p(Man-TLR) or TLR7-MA. p(Man-TLR) induces increased production of IL-12p70 (d.), IL-6 (e.), and TNFα (f.) as compared to BMDCs treated an equal amount of unpolymerized monomer.

FIGS. 9A-D shows graphical data demonstrating that (Man-TLR) conjugation to OVA increases the uptake of OVA by various DC subsets as compared to unconjugated OVA. a-b. Mice were treated with an intradermal injection of fluorescently labeled OVA or fluorescently labeled OVA conjugated to either p(Man) or p(Man-TLR). After 12 h, the lymph nodes of the animals were harvested and the cells of the lymph nodes were analyzed for fluorescently labeled OVA content via flow cytometry. Conjugation of OVA to p(Man-TLR) increases the uptake of OVA by CD8+ cross-presenting DCs (a.), CD4+ activating DCs (b.), CD4−/CD8− lymph node resident DCs (c.), and conventional dermal DCs (d.).

FIGS. 10A-D shows graphical data demonstrating that mice immunized with OVA-p(Man-TLR) had more robust CD4+ and CD8+ T cell responses as compared to OVA administered with unconjugated p(Man-TLR) or OVA-p(Man) conjugates administered with TLR7-MA. a-d. Mice were immunized on day 0 and 28 with one of six formulations: 1.) 10 µg of OVA+30 µg, 2.) p(Man-TLR) (30 µg equivalent of TLR7-MA), 3.) 10 µg of OVA and unconjugated p(Man-TLR) (30 µg equivalent of TLR7-MA), 4.) 10 µg of OVA-p(Man) conjugate with 30 µg of TLR7-MA, or 5.) 10 µg of OVA-p(Man-TLR).

FIGS. 11A-E shows graphical data demonstrating that mice immunized with OVA-p(Man-TLR) mounted an increased plasma cell, Tfh cell, and antibody response as compared mice treated with other formulations. a-d. Mice were immunized on day 0 and 28 with one of six formulations: 1.) 10 µg of OVA+30 µg, 2.) p(Man-TLR) (30 µg equivalent of TLR7-MA), 3.) 10 µg of OVA and unconjugated p(Man-TLR) (30 µg equivalent of TLR7-MA), 4.) 10 µg of OVA-p(Man) conjugate with 30 µg of TLR7-MA, or 5.) 10 µg of OVA-p(Man-TLR).

DESCRIPTION OF ILLUSTRATIVE EMBODIMENTS

I. Definitions

Figure 3:
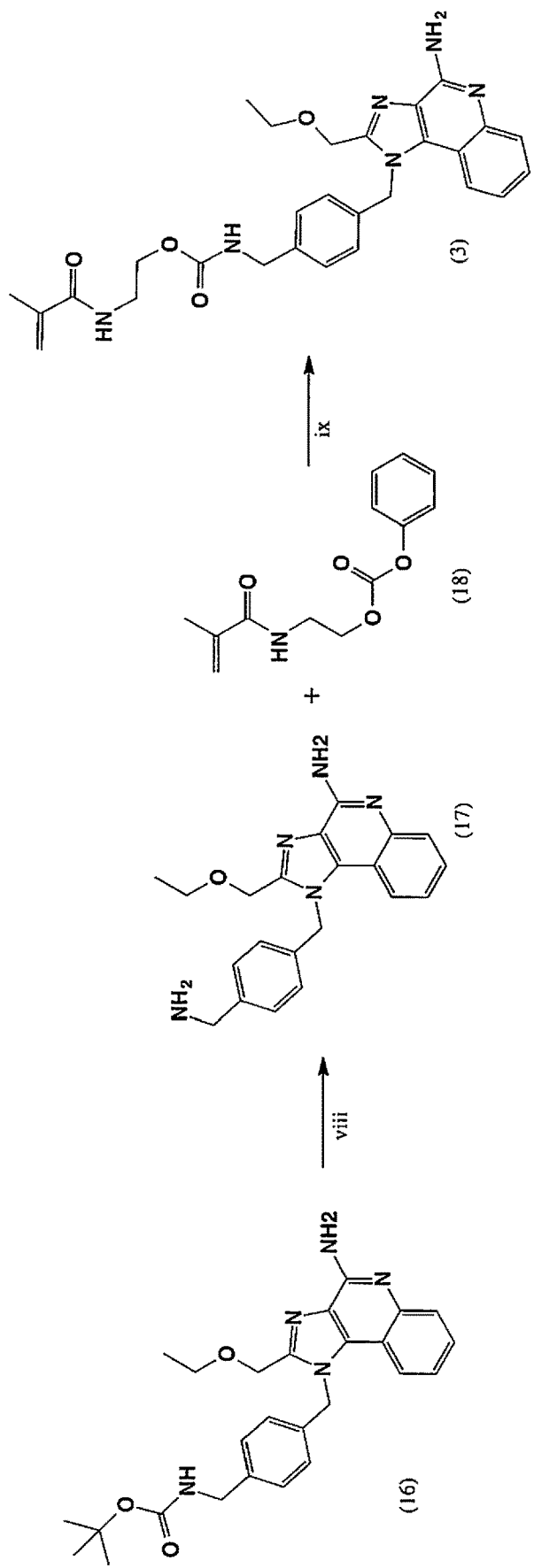
FIG. 3 shows a reaction schematic for the preparation of TLR7-MA (3).

The term "each independently" is used herein to indicate that the choices can be identical or different, i.e., in the case of R groups, for example, the term "each independently" indicates that the R groups (e.g., $R_1$, $R_2$) can be identical (e.g., $R_1$ and $R_2$ may both be substituted alkyl groups) or different (e.g., $R_1$ may be an alkyl group and $R_2$ may be an alkoxy group) specified otherwise, a named R group will have the structure recognized in the art as corresponding to R groups with that name. For the purposes of illustration, representative R groups are defined herein. These definitions are intended to supplement and illustrate, not preclude, the definitions known to those of skill in the art.

The term "aliphatic group" denotes an acyclic or cyclic, saturated or unsaturated hydrocarbon group excluding aromatic compounds. "Substituted aliphatic group" refers to an aliphatic group as just described in which one or more hydrogen atoms attached to carbon of the aliphatic group is replaced by any other group, such as halogen, aryl, substituted aryl, heteroaryl, substituted heteroaryl, cycloalkyl, alkoxy, amino, ester, amide, alcohol, and combinations thereof.

The term "alkyl group" denotes a monovalent linear or branched saturated hydrocarbon group of 1 to 12 carbon atoms. In certain embodiments, an alkyl group has 1 to 7 carbon atoms, and in more particular embodiments 1 to 4 carbon atoms. Non-limiting examples of alkyl groups include methyl, ethyl, propyl, isopropyl, n-butyl, iso-butyl, and sec-butyl. Particular alkyl groups include methyl, ethyl, propyl and isopropyl. More particular alkyl groups are methyl, ethyl and propyl.

The term "substituted alkyl group" refers to an alkyl group as just described in which one or more hydrogen atoms attached to at least one carbon of the alkyl group is replaced by any other group, such as halogen, aryl, substituted aryl, heteroaryl, substituted heteroaryl, cycloalkyl, alkoxy, amino, ester, amide, alcohol, and combinations thereof.

The term "cycloalkyl group" denotes a cyclized alkyl group, for example cyclopropyl, cyclobutyl, cyclopentyl, cyclohexyl, etc.

The term "substituted cycloalkyl group" refers to a cycloalkyl group as just described in which one or more hydrogen atoms attached to at least one carbon of the cycloalkyl group is replaced by another group, such as halogen, alkyl, substituted alkyl, aryl, substituted aryl, cycloalkyl, substituted cycloalkyl, heterocycloalkyl, heteroaryl, substituted heteroaryl, alkoxy, aryloxy, boryl, phosphino, amino, thio, ester, amide, alcohol and combinations thereof.

The term "heteroalkyl group" refers to an alkyl or a substituted alkyl group as described above in which one or more carbon atoms are replaced with a heteroatom from the group consisting of N, O, P, B, S, Si, Se and Ge. The bond between the carbon atom and the heteroatom may be saturated or unsaturated. Examples include an alkoxy group such as methoxy, ethoxy, propoxy, iso-propoxy, butoxy or t-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. Thus, an alkyl group substituted with a group such as heterocycloalkyl, substituted heterocycloalkyl, heteroaryl, substituted heteroaryl, alkoxy, aryloxy, boryl, phosphino, amino, imino, or thio is within the scope of the term heteroalkyl group.

The term "heterocycloalkyl group" refers to a cycloalkyl group as described, but in which one or more or all carbon atoms of the unsaturated group are replaced by a heteroatom from the group consisting of N, O, P, B, S, Si, Se and Ge. Suitable heterocycloalkyl groups include, for example, piperazinyl, morpholinyl, tetrahydropyranyl, tetrahydrofuranyl, piperidinyl and pyrrolidinyl.

The term "substituted heterocycloalkyl group" refers to a heterocycloalkyl group as just described, but in which one or more hydrogen atoms on any atom of the heterocycloalkyl group is replaced by another group such as a halogen, alkyl, substituted alkyl, aryl, substituted aryl, cycloalkyl, substituted cycloalkyl, heterocycloalkyl, heteroaryl, substituted heteroaryl, alkoxy, aryloxy, boryl, phosphino, amino, thio, and combinations thereof.

The term "aryl group" refers to an aromatic substituent, which may be a single aromatic ring or multiple aromatic rings which are fused together, linked covalently, or linked to a common group such as a methylene or ethylene moiety. The common linking group may also be a carbonyl as in benzophenone or a heteroatom, such as oxygen in the case of diphenylether or nitrogen in the case of diphenylamine. The aromatic ring(s) may include phenyl, naphthyl, biphenyl, diphenylether, diphenylamine and benzophenone among others. In certain embodiments, aryl groups have between 1 and 50 carbon atoms, 1 and 9 carbon atoms, or 1 and 6 carbon atoms.

The term "substituted aryl group" refers to an aryl group as just described in which one or more hydrogen atoms attached to any carbon atom is replaced by one or more functional groups such as alkyl, substituted alkyl, cycloalkyl, substituted cycloalkyl, heterocycloalkyl, substituted heterocycloalkyl, halogen, halogenated alkyl (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific example of substituted aryl groups include perfluorophenyl, chlorophenyl, 3,5-dimethylphenyl, 2,6-diisopropylphenyl and the like.

The term "heteroaryl group" refers to aromatic ring(s) in which one or more carbon atoms of the aromatic ring(s) are replaced by a heteroatom(s) such as nitrogen, oxygen, boron, selenium, phosphorus, silicon or sulfur. Heteroaryl group refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. Rings such as thiophene, pyridine, oxazole, isoxazole, thiazole, isothiazole, isophthalimide, pyrazole, indole, pyridine, pyrimidine, pyrazine, furan, etc. or benzo-fused analogues of these rings are defined by the term "heteroaryl group."

The term "substituted heteroaryl group" refers to a heteroaryl group as just described in which one or more hydrogen atoms on any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl groups include, for example, 4-N,N-dimethylaminopyridine.

The term "alkoxy group" refers to the —OZ' radical, where Z' is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy groups include, for example, methoxy, ethoxy, benzyloxy, t-butoxy, and the like. A related term is "aryloxy" where Z' is selected from the group consisting of aryl, substituted aryl, heteroaryl, substituted heteroaryl, and combinations thereof. Examples of suitable aryloxy groups include phenoxy, substituted phenoxy, 2-pyridinoxy, 8-quinalinoxy and the like.

The term "alkoxyalkyl group" denotes an alkyl group where at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl groups include methoxymethyl, methoxyethyl and ethoxymethyl.

The term "alkoxyalkoxy group" denotes an alkoxy group wherein at least one of the hydrogen atoms of the alkoxy group has been replaced by another alkoxy group. Examples of alkoxyalkoxy groups include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl group" denotes an alkyl group wherein at least one of the hydrogen atoms of the alkyl group has been replaced by an alkoxyalkoxy group. Examples of alkoxyalkoxyalkyl groups include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "amino group" refers to the group —NZ'Z", where each of Z' and Z" is each independently selected from hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, alkyloxyalkyl, aryloxy, and combinations thereof.

The term "halogen" means fluoro, chloro, bromo, or iodo, preferably fluoro or chloro.

The term "carbonyl" denotes a

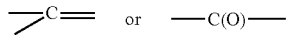

group.

The term "hydroxy" or "alcohol" denotes a —OH group.
The term "cyano" denotes a —C≡N group
The term "azide" denotes a —N₃ group.

The compounds and polymers of the present invention may have asymmetric centers. Compounds and polymers of the present invention containing an asymmetrically substituted atom may be isolated in optically active or racemic forms. According to the Cahn-Ingold-Prelog Convention the asymmetric carbon atom can be of the "R" or "S" configuration. It is well known in the art how to prepare optically active forms, such as by resolution of materials. All chiral, diastereomeric, meso, racemic forms are within the scope of this invention, unless the specific stereochemistry or isomeric form is specifically indicated.

Additionally, as used herein the term $C_1$-$C_6$ alkyl and terms derived therefrom includes all the possible isomeric forms of said $C_1$-$C_6$ alkyl group. Furthermore, the heteroaryl include all the positional isomers. Furthermore, all polymorphic forms and hydrates of monomer (VI), copolymers (I), (IV), (VII), or polymer (VIII) are within the scope of this invention.

The terms "compound" and "a compound of the invention" and "compound of the present invention" and the like, and their plural forms include the embodiment of formula (III) and (VI) and the other more particular embodiments encompassed by copolymers (I), (IV), (VII), or polymer (VIII) described herein and exemplified compounds described herein or a pharmaceutically acceptable salt of each of these embodiments. All references to compounds, include all isotopes of the atoms contained therein, including isotopically-labeled compounds.

The terms "polymer" and "a polymer of the invention" and "polymer of the present invention" and the like, and their plural forms include the embodiment of formula (VIII) and the other more particular embodiments encompassed by monomer (VI), copolymers (I), (IV) and (VII) described herein and exemplified compounds and polymers described herein or a pharmaceutically acceptable salt of each of these embodiments. All references to polymers, include all isotopes of the atoms contained therein, including isotopically-labeled polymers.

The compounds and polymers of the present invention may exist as tautomers. All tautomeric forms of the compounds of the invention are contemplated to be within the scope of the present invention.

The compositions also include the prodrugs of monomer (VI), copolymers (I), (IV), (VII), or polymer (VIII). The term prodrug is intended to represent covalently bonded carriers, which are capable of releasing the active ingredient of monomer (VI), copolymers (I), (IV), (VII), or polymer (VIII) respectively, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of monomer (VI), copolymers (I), (IV), (VII), or polymer (VIII) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups), amides (e.g., trifluoroacetylamino, acetylamino, and the like), and the like.

A "pharmaceutically acceptable salt" of a compound means a salt that is pharmaceutically acceptable and that possesses the desired pharmacological activity of the parent compound. Non-limiting examples of such salts include acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are nontoxic. Additional information on suitable pharmaceutically acceptable salts can be found in *Remington's Pharmaceutical Sciences*, 17th ed., Mack Publishing Company, Easton, Pa., 1985, which is incorporated herein by reference.

An "antigen" includes any substance that may be specifically bound by an antibody molecule. Thus, the term "antigen" encompasses biologic molecules including, but not limited to, simple intermediary metabolites, sugars, lipids, amino acids, and hormones, as well as macromolecules such as complex carbohydrates, phopholipids, nucleic acids and proteins, for example ovalbumin (OVA). In certain embodiments, the antigen is one that is related to the infection or disease to be treated. In specific embodiments, the antigen is from an infectious agent or from a tumor or cancer cell. The antigen may be all or part of a molecule from an infectious agent or tumor/cancer cell so long as it elicits an immune response against the antigen. In particular embodiments, the antigen is one in which an immune response is desired or intended.

The term "polymer" refers to a molecule composed of repeating structural units connected by covalent chemical bonds often characterized by a substantial number of repeating units (e.g., equal to or greater than 10 repeating units and often equal to or greater than 50 repeating units and often equal to or greater than 100 repeating units) and a high molecular weight (e.g., greater than or equal to 50,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, alternating, segmented, grafted, tapered and other copolymers. Useful polymers include organic polymers that are water miscible for vaccine administration.

An "oligomer" refers to a molecule composed of repeating structural units connected by covalent chemical bonds often characterized by a number of repeating units less than that of a polymer (e.g., equal to or less than 10 repeating units) and a lower molecular weights (e.g., less than or equal to about 50,000 Da) than polymers. Oligomers may be the polymerization product of one or more monomer precursors.

It is specifically contemplated that any of m, o, p, p' or the number of monomers are integers and may be, be at least, or be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000 or more, or any range derivable therein.

The term "operatively linked" refers to a situation where two components are combined to form the active complex prior to binding at the target site. For example, a molecule conjugated to one-half of a biotin-streptavidin complex and an antigen complexed to the other one-half of the biotin-streptavidin complex are operatively linked through complexation of the biotin and streptavidin molecules. The term operatively linked is also intended to refer to covalent or chemical linkages that conjugate two molecules together.

II. Compounds of Formula (VI)

In one embodiment, low toxicity, small molecule Toll-Like Receptor (TLR)-7 and/or TLR-8 imidazoquinoline ligands are provided as vaccine adjuvants with decreased hydrophobicity (c Log P) and increased activity for use in vaccine formulations. In one embodiment, the TLR7 agonist, TLR8 agonist, or TLR7/8 agonist monomer has the general structure (VI):

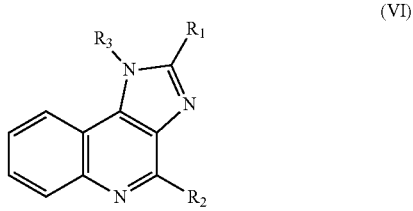

(VI)

where $R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, or a substituted aryl group; and $R_3$ is a ligand comprising a polymerizable group Y'.

Non-limiting examples of imidazoquinoline compounds of general structure (VI) for use in the current embodiments that are easily derived using various commercially available acid chlorides (e.g., substituting for (14) in the synthetic protocol described herein in FIG. 2, step vi) include 2-methacrylamidoethyl 4-((4-amino-2-methyl-1H-imidazo[4,5-c]quinolin-1-yl)methyl)benzylcarbamate, 2-methacrylamidoethyl 4-((4-amino-2-ethyl-1H-imidazo[4,5-c]quinolin-1-yl)methyl)benzylcarbamate, 2-methacrylamidoethyl 4-((4-amino-2-isopropyl-1H-imidazo[4,5-c]quinolin-1-yl)methyl)benzylcarbamate, 2-methacrylamidoethyl 4-((4-amino-2-isopropyl-1H-imidazo[4,5-c]quinolin-1-yl)methyl)benzylcarbamate, 2-methacrylamidoethyl 4-((4-amino-2-cyclopropyl-1H-imidazo[4,5-c]quinolin-1-yl)methyl)benzylcarbamate, 2-methacrylamidoethyl 4-((4-amino-2-butyl-1H-imidazo[4,5-c]quinolin-1-yl)methyl)benzylcarbamate, 2-methacrylamidoethyl 4-((4-amino-2-isobutyl-1H-imidazo[4,5-c]quinolin-1-yl)methyl)benzylcarbamate, 2-methacrylamidoethyl 4-((4-amino-2-sec-butyl-1H-imidazo[4,5-c]quinolin-1-yl)methyl)benzylcarbamate, 2-methacrylamidoethyl 4-((4-amino-2-cyclobutyl-1H-imidazo[4,5-c]quinolin-1-yl)methyl)benzylcarbamate, 2-methacrylamidoethyl 4-((4-amino-2-(oxetan-2-yl)-1H-imidazo[4,5-c]quinolin-1-yl)methyl)benzylcarbamate, 2-methacrylamidoethyl 4-((4-amino-2-(oxetan-3-yl)-1H-imidazo[4,5-c]quinolin-1-yl)methyl)benzylcarbamate, 2-methacrylamidoethyl 4-((4-amino-2-cyclopentyl-1H-imidazo[4,5-c]quinolin-1-yl)methyl)benzylcarbamate, 2-methacrylamidoethyl 4-((4-amino-2-(tetrahydrofuran-3-yl)-1H-imidazo[4,5-c]quinolin-1-yl)methyl)benzylcarbamate, 2-methacrylamidoethyl 4-((4-amino-2-(tetrahydrofuran-2-yl)-1H-imidazo[4,5-c]quinolin-1-yl)methyl)benzylcarbamate, 2-methacrylamidoethyl 4-((4-amino-2-(2-methoxyethyl)-1H-imidazo[4,5-c]quinolin-1-yl)methyl)benzylcarbamate, 2-methacrylamidoethyl 4-((4-amino-2-(ethoxymethyl)-1H-imidazo[4,5-c]quinolin-1-yl)methyl)benzylcarbamate (TLR-7-oxyethyl-methacrylamide(TLR-MA, 3)), 2-methacrylamidoethyl 4-((4-amino-2-((2-methoxyethoxy)methyl)-1H-imidazo[4,5-c]quinolin-1-yl)methyl)benzylcarbamate, 4-amino-1-(4-(((2-methacrylamidoethoxy)carbonylamino)methyl)benzyl)-1H-imidazo[4,5-c]quinoline-2-carboxylic acid, methyl 4-amino-1-(4-(((2-methacrylamidoethoxy)carbonylamino)methyl)benzyl)-1H-imidazo[4,5-c]quinoline-2-carboxylate, ethyl 4-amino-1-(4-(((2-methacrylamidoethoxy)carbonylamino)methyl)benzyl)-1H-imidazo[4,5-c]quinoline-2-carboxylate, 2-(4-amino-1-(4-(((2-methacrylamidoethoxy)carbonylamino)methyl)benzyl)-1H-imidazo[4,5-c]quinolin-2-yl)acetic acid, methyl 2-(4-amino-1-(4-(((2-methacrylamidoethoxy)carbonylamino)methyl)benzyl)-1H-imidazo[4,5-c]quinolin-2-yl)acetate, ethyl 2-(4-amino-1-(4-(((2-methacrylamidoethoxy)carbonylamino)methyl)benzyl)-1H-imidazo[4,5-c]quinolin-2-yl)acetate, 3-(4-amino-1-(4-(((2-methacrylamidoethoxy)carbonylamino)methyl)benzyl)-1H-imidazo[4,5-c]quinolin-2-yl)propanoic acid, methyl 3-(4-amino-1-(4-(((2-methacrylamidoethoxy)carbonylamino)methyl)benzyl)-1H-imidazo[4,5-c]quinolin-2-yl)propanoate, ethyl 3-(4-amino-1-(4-(((2-methacrylamidoethoxy)carbonylamino)methyl)benzyl)-1H-imidazo[4,5-c]quinolin-2-yl)propanoate, 2-methacrylamidoethyl 4-((4-amino-2-(thiazol-2-yl)-1H-imidazo[4,5-c]quinolin-1-yl)methyl)benzylcarbamate, 2-methacrylamidoethyl 4-((4-amino-2-(thiazol-5-yl)-1H-imidazo[4,5-c]quinolin-1-yl)methyl)benzylcarbamate, 2-methacrylamidoethyl 4-((4-amino-2-(isothiazol-5-yl)-1H-imidazo[4,5-c]quinolin-1-yl)methyl)benzylcarbamate, 2-methacrylamidoethyl 4-((4-amino-2-(isothiazol-3-yl)-1H-imidazo[4,5-c]quinolin-1-yl)methyl)benzylcarbamate, 2-methacrylamidoethyl 4-((4-amino-2-(isothiazol-4-yl)-1H-imidazo[4,5-c]quinolin-1-yl)methyl)benzylcarbamate, 2-methacrylamidoethyl 4-((4-amino-2-(thiazol-4-yl)-1H-imidazo[4,5-c]quinolin-1-yl)methyl)benzylcarbamate, 2-methacrylamidoethyl 4-((4-amino-2-(oxazol-4-yl)-1H-imidazo[4,5-c]quinolin-1-yl)methyl)benzylcarbamate, 2-methacrylamidoethyl 4-((4-amino-2-(isoxazol-4-yl)-1H-imidazo[4,5-c]quinolin-1-yl)methyl)benzylcarbamate, 2-methacrylamidoethyl 4-((4-amino-2-(isoxazol-3-yl)-1H-imidazo[4,5-c]quinolin-1-yl)methyl)benzylcarbamate, 2-methacrylamidoethyl 4-((4-amino-2-(furan-2-yl)-1H-imidazo[4,5-c]quinolin-1-yl)methyl)benzylcarbamate, 2-methacrylamidoethyl 4-((4-amino-2-(furan-3-yl)-1H-imidazo[4,5-c]quinolin-1-yl)methyl)benzylcarbamate, 2-methacrylamidoethyl 4-((4-amino-2-(thiophen-3-yl)-1H-imidazo[4,5-c]quinolin-1-yl)methyl)benzylcarbamate, 2-methacrylamidoethyl 4-((4-amino-2-(thiophen-2-yl)-1H-imidazo[4,5-c]quinolin-1-yl)methyl)benzylcarbamate, 2-methacrylamidoethyl 4-((4-amino-2-(oxazol-2-yl)-1H-imidazo[4,5-c]quinolin-1-yl)methyl)benzylcarbamate, 2-methacrylamidoethyl 4-((4-amino-2-(oxazol-5-yl)-1H-imidazo[4,5-c]quinolin-1-yl)methyl)benzylcarbamate, 2-methacrylamidoethyl 4-((4-amino-2-(isoxazol-5-yl)-1H-imidazo[4,5-c]quinolin-1-yl)methyl)benzylcarbamate, 2-methacrylamidoethyl 4-((4-amino-2-(pyridin-2-yl)-1H-imidazo[4,5-c]quinolin-1-yl)methyl)benzylcarbamate, 2-methacrylamidoethyl 4-((4-amino-2-(pyridin-3-yl)-1H-imidazo[4,5-c]quinolin-1-yl)methyl)benzylcarbamate, 2-methacrylamidoethyl 4-((4-amino-2-(pyridin-4-yl)-1H-imidazo[4,5-c]quinolin-1-yl)methyl)benzylcarbamate, 2-methacrylamidoethyl 4-((4-amino-2-(pyrimidin-4-yl)-1H-imidazo[4,5-c]quinolin-1-yl)methyl)benzylcarbamate, 2-methacrylamidoethyl 4-((4-amino-2-(pyrazin-2-yl)-1H-imidazo[4,5-c]quinolin-1-yl)methyl)benzylcarbamate, 2-methacrylamidoethyl 4-((4-amino-2-(pyridazin-3-yl)-1H-imidazo[4,5-c]quinolin-1-yl)methyl)benzylcarbamate, 2-methacrylamidoethyl 4-((4-amino-2-(pyridazin-4-yl)-1H-imidazo[4,5-c]quinolin-1-yl)methyl)benzylcarbamate, 2-methacrylamidoethyl 4-((4-amino-2-(pyrimidin-5-yl)-1H-imidazo[4,5-c]quinolin-1-yl)methyl)benzylcarbamate, and derivatives thereof. Exemplary imidazoquinoline derivatives further include: N-(3-(4-amino-2-(ethoxymethyl)-1H-imidazo[4,5-c]quinolin-1-yloxy)propyl)methacrylamide, N-(4-(4-amino-2-(ethoxymethyl)-1H-imidazo[4,5-c]quinolin-1-yloxy)butyl)methacrylamide, N-(4-(4-amino-2-(ethoxymethyl)-1H-imidazo[4,5-c]quinolin-1-yloxy)pentyl)methacrylamide, N-(4-(4-amino-2-(ethoxymethyl)-1H-imidazo[4,5-c]quinolin-1-yloxy)hexyl)methacrylamide, N-(4-(4-amino-2-

(ethoxymethyl)-1H-imidazo[4,5-c]quinolin-1-yloxy)heptyl) methacrylamide, N-(4-(4-amino-2-(ethoxymethyl)-1H-imidazo[4,5-c]quinolin-1-yloxy)octyl)methacrylamide, N-(4-(4-amino-2-(ethoxymethyl)-1H-imidazo[4,5-c]quinolin-1-yloxy)nonyl)methacrylamide, N-(4-(4-amino-2-(ethoxymethyl)-1H-imidazo[4,5-c]quinolin-1-yloxy)decyl) methacrylamide, as well as those N—O bond containing structures containing the above mentioned 4- and 2-position imidazoquinoline substitutions and derivatives thereof. The 4-amino group in common to the above mentioned variously 2-substituted imidazoquinoline derivatives installed in FIG. 2 (step vii) could be any other nucleophile capable of a nucleophilic aromatic substitution ($S_NAr$) reaction with 4-substituted heteroaryl chloride, for example hydroxide, methylamine, dimethylamine, ethylamine, methylethylamine, propylamine, azetidine, cyclopropylamine, pyrrolidine, etc. Alternatively the 4-substituted heteroaryl chloride may be replaced with hydrogen by a hydro or radical dehalogenation reaction or participate as a coupling partner in a transition metal catalyzed carbon-carbon bond formation reaction.

In select embodiments of the current disclosure, any of the disclosed TLR agonist monomers can be linked with another monomer that contains at least one group that binds to an Antigen Presenting Cell (APC) mannose receptor as polymers, homopolymers, copolymers, copolymeric blends, terpolymers, quaterpolymers, or oligomers, etc., and can be present in compositions and conjugated to, for example, antigens. Any of the copolymers may be a block copolymer, an alternating copolymer or a random copolymer. Preferably the compounds, copolymers, and polymers of the present invention are hydrophilic. Non-limiting examples of water-soluble polymers that may find use in the current embodiments include polyacrylates, such as poly(acrylic acid) or poly(methacrylic acid) or poly(hydrxypropyl methacrylate), polyamides, such as poly(acrylamide) or poly(methacrylamide), polysaccharides, polyoxazoline, such as poly(ethyloxazoline), polyimine, such as poly(ethylenimine), and polyvinyl derivatives, such as a poly(vinylalcohol) or poly(vinylpyrrolidone). Linking of monomers to form polymers, homopolymers, copolymers, polymeric blends, terpolymers, quaterpolymers, or oligomers and conjugation to, for instance, antigens as disclosed in the current embodiments, may be accomplished using synthetic organic techniques using polymerizable and linking groups which would be readily apparent to one of ordinary skill in the art, based on the present disclosure. Non-limiting examples of making the compounds, copolymers, and polymers of the present invention are provided in the Examples section.

III. Linkers

In one application, linkers include compounds for molecular conjugation reactions to provide structural stability or assistance in protein-protein, protein-peptide, protein-polymer, polymer-small molecule, peptide/protein-small molecule interactions, immobilization for assays or purification, as well as various peptide-nucleic acid and nucleic acid-nucleic acid conjugations, among many others. Typically, linkers contain functional groups, such as primary amines, sulfhydryls, acids, alcohols, azides, alkynes and halides. Specifically, maleimide (sulfhydryl reactive) and succinimidyl ester (NETS) or isothiocyanate (ITC) groups that react with amines may find use in the current embodiments.

1. Bifunctional Linkers

In one embodiment, a bifunctional linker can be used as a latent spacer between a therapeutic or diagnostic moiety and a polymer. In one aspect, the latency is selected such that a first linking group (functional group) of the bifunctional linker can be selectively conjugated in the presence of a second linking group. In another aspect, the latency can be selected such that after both linking groups on the bifunctional linker are conjugated one group can be selectively cleaved. For example, the hydrolysis of the spacer-polymer bond can be rate limiting in the release of the therapeutic or diagnostic moiety from the polymeric prodrug. Cleavage and release of the therapeutic or diagnostic moiety from the polymeric prodrug can occur in vivo, for example by an enzymatic or non-enzymatic hydrolysis mechanism using linking groups such as ester, carbonate, carbamate, imine (hydrazone), amide, maleimide, succinimidyl, vinylsulfone, conjugated C═C double bond, epoxy, aldehyde, ketone, silane or siloxane functionalities. It is within the purview of those skilled in the art to appreciate the release of a therapeutic or diagnostic moiety from polymeric prodrugs employing aqueous hydrolysis depends on a multitude of factors like hydration of the linkage, the nature of the leaving group and steric crowding around the linkage. Substrate specificity, hydrophilicity, and steric crowding all influence the release from enzyme susceptible linkages and subtle changes made to the specific embodiments disclosed herein can still obtain the same result without departed from the spirit and scope of the invention. In certain aspects, the bifunctional linkers can be first conjugated with the copolymers and polymers of the current invention through a first functional group on the bifunctional linker and then the product can be further conjugated through a second functional group on the bifunctional linker. Once both functional groups of the bifunctional linker are conjugated, the portion derived from the bifunctional linker can be referred to as a linking group or linker. Exemplary compounds used as bifunctional linkers in the preparation of the polymeric conjugated vaccines of the current invention including any of the above mentioned functional groups can include alkyne-PEG5-acid, N-alloc-1,4-butandiamine hydrochloride, N-alloc-1,6-hexanediamine hydrochloride, allyl(4-methoxyphenyl)dimethyl silane, 6-(allyloxycarbonylamino)-1-hexanol, 3-(allyloxycarbonylamino)-1-propanol, 4-aminobutyraldehyde diethyl acetal, (E)-N-(2-aminoethyl)-4-{2-[4-(3-azidopropoxy)phenyl]diazenyl}benzamide hydrochloride, N-(2-aminoethyl) maleimide trifluoroacetate salt, amino-PEG4-alkyne, benzyl N-(3-hydroxypropyl)carbamate, 4-(Boc-amino)-1-butanol, 4-(Boc-amino)butyl bromide, 2-(Boc-amino)ethanethiol, 2-[2-(Boc-amino)ethoxy]ethoxyacetic acid, (dicyclohexylammonium) salt, 2-(Boc-amino)ethyl bromide, 6-(Boc-amino)-1-hexanol, 21-(Boc-amino)-4,7,10,13,16,19-hexaoxaheneicosanoic acid, 6-(Boc-amino)hexyl bromide, 5-(Boc-amino)-1-pentanol, 3-(Boc-amino)-1-propanol, 3-(Boc-amino)propyl bromide, 15-(Boc-amino)-4,7,10,13-tetraoxapentadecanoic acid, N-Boc-1,4-butanediamine, N-Boc-cadaverine, N-Boc-ethanolamine, N-Boc-ethylenediamine, N-Boc-2,2'-(ethylenedioxy)diethylamine, N-Boc-1,6-hexanediamine, N-Boc-1,6-hexanediamine hydrochloride, N-Boc-4-isothiocyanatoaniline, N-Boc-4-isothiocyanatobutylamine, N-Boc-2-isothiocyanatoethylamine, N-Boc-3-isothiocyanatopropylamine, N-Boc-N-methylethylenediamine, N-Boc-m-phenylenediamine, N-Boc-p-phenylenediamine, 2-(4-Boc-1-piperazinyl)acetic acid, N-Boc-1,3-propanediamine, N-Boc-1,3-propanediamine, N-Boc-N'-succinyl-4,7,10-trioxa-1,13-tridecanediamine, N-Boc-4,7,10-trioxa-1,13-tridecanediamine, N-(4-Bromobutyl)phthalimide, 4-bromobutyric acid, 4-bromobutyryl chloride, 4-bromobutyryl chloride, N-(2-bromoethyl)phthalimide, 6-bromo-1-hexanol, 3-(bromomethyl)benzoic acid N-succinimidylester, 4-(bromomethyl) phenyl isothiocyanate, 8-bromooctanoic acid, 8-bromo-1-octanol, 4-(2-bromopropionyl)phenoxyacetic acid, N-(3-bromopropyl)phthalimide, 4-(tert-Butoxymethyl)benzoic acid, tert-butyl 2-(4-{[4-(3-azidopropoxy)phenyl] azo}benzamido)ethylcarbamate, 2-[2-(tert-butyldimethylsilyloxy)ethoxy]ethanamine, tert-butyl 4-hydroxybutyrate, chloral hydrate, 4-(2-chloropropionyl)phenylacetic acid, 1,11-diamino-3,6,9-trioxaundecane, di-Boc-cystamine, diethylene glycol monoallyl ether, 3,4-Dihydro-2H-pyran-2-methanol, 4-[(2,4-Dimethoxyphenyl)(Fmoc-amino) methyl]phenoxyacetic acid, 4-(Diphenylhydroxymethyl) benzoic acid, 4-(Fmoc-amino)-1-butanol, 2-(Fmoc-amino) ethanol, 2-[2-(Fmoc-amino)ethoxy]ethylamine hydrochloride, 2-(Fmoc-amino)ethyl bromide, 6-(Fmoc-amino)-1-hexanol, 5-(Fmoc-amino)-1-pentanol, 3-(Fmoc-amino)-1-propanol, 3-(Fmoc-amino)propyl bromide, N-Fmoc-2-bromoethylamine, N-Fmoc-1,4-butanediamine hydrobromide, N-Fmoc-cadaverine hydrobromide, N-Fmoc-ethylenediamine hydrobromide, N-Fmoc-1,6-hexanediamine hydrobromide, N-Fmoc-1,3-propanediamine hydrobromide, N-Fmoc-N"-succinyl-4,7,10-trioxa-1,13-tridecanediamine, (3-Formyl-1-indolyl)acetic acid 6-Guanidinohexanoic acid 4-Hydroxybenzyl alcohol N-(4-hydroxybutyl)trifluoroacetamide, 4'-hydroxy-2,4-dimethoxybenzophenone, N-(2-hydroxyethyl)maleimide, 4-[4-(1-hydroxyethyl)-2-methoxy-5-nitrophenoxy]butyric acid, N-(2-hydroxyethyl)trifluoroacetamide, N-(6-hydroxyhexyl) trifluoroacetamide, 4-hydroxy-2-methoxybenzaldehyde, 4-hydroxy-3-methoxybenzyl alcohol, 4-(hydroxymethyl) benzoic acid, 4-hydroxymethyl-3-methoxyphenoxyacetic acid, 4-(4-hydroxymethyl-3-methoxyphenoxy)butyric acid, 4-(hydroxymethyl)phenoxyacetic acid, 3-(4-hydroxymethylphenoxy)propionic acid, N-(5-hydroxypentyl)trifluoroacetamide, 4-(4'-hydroxyphenylazo)benzoic acid, N-(3-hydroxypropyl)trifluoroacetamide, 2-maleimidoethyl mesylate, 4-mercapto-1-butanol, 6-mercapto-1-hexanol, phenacyl 4-(bromomethyl)phenylacetate, phenacyl 4-(bromomethyl)phenylacetate, 4-sulfamoylbenzoic acid, 4-sulfamoylbutyric acid, N-trityl-1,2-ethanediamine hydrobromide, 4-(Z-amino)-1-butanol, 6-(Z-amino)-1-hexanol, 5-(Z-amino)-1-pentanol, N—Z-1,4-butanediamine hydrochloride, N—Z-ethanolamine, N—Z-ethylenediamine hydrochloride, N—Z-ethylenediamine hydrochloride, N—Z-1,6-hexanediamine hydrochloride, N—Z-1,5-pentanediamine hydrochloride, and N—Z-1,3-propanediamine hydrochloride. Non-limiting examples of trifunctional linkers used to link three separate molecules together include N1,N4-bis-Boc-spermidine, N1,N5-bis-Boc-spermidine, N-Boc-diethanolamine, N1-Boc-2,2'-iminodiethylamine, N-Boc-iminodipropionic acid, N1-Boc-3,3'-iminodipropylamine, N,N"-Di-Z-diethylenetriamine. In specific aspects, the bifunctional linker contains a radical conjugation functional group, such as found in 2-(2-(2-(2-azidoethoxy)ethoxy)ethoxy)ethyl 4-cyano-4-(phenylcarbonothioyl-thio)pentanoate that can be first conjugated with monomers in a polymerization reaction (i.e., reversible addition-fragmentation chain transfer (RAFT) polymerization) to afford an azide functionalized agent. The azide agent can then be used in subsequent conjugation reactions to prepare polymer conjugate vaccines or polymer conjugate vaccine precursors. A non-limiting example of a commercial source of the above mentioned bifunctional and trifunctional linkers is Sigma Aldrich® (U.S.A).

2. Self-Immolating Linkers

In other embodiments, polymeric compositions using methods of site-specific controlled release of antigens are disclosed. These polymers and methods provide the impetus for a diverse range of applications spanning drug delivery, biological and chemical sensors, and diagnostics. One such novel substrate-polymer coupling moiety that finds use in the current embodiments includes self-immolating linkers. Self-immolating linkers utilize polymeric release of a stable bond between protecting and leaving groups, which becomes labile upon activation, leading to the rapid disassembly of the parent polymer by electronic cascade, dendrimer or polymer disassembly, or chemical amplified release. Chemical amplifiers are structures that translate a single bond-breaking event into release of numerous chemical outputs. In this way, a single bond cleavage input reaction (e.g., a reaction triggered by an analyte, a photon, or an enzyme) can be translated into the release of numerous output chemical cargoes. Outputs can take the form of reporting molecules (e.g., fluorescent dyes), biomolecules, antigens, or drugs. The current embodiments include self-immolating linker technologies comprising a trigger, linker and effector units such as those used in non-toxic prodrugs to enhance the selectivity in cancer chemotherapy, i.e., using monoclonal antibodies to specifically deliver highly potent, conjugated small molecule therapeutics to cancer cells. In another aspect, a self-immolating linker such as PABC or PAB (para-aminobenzyloxycarbonyl) and derivatives are self-immolating electronic cascade linkers formed by linking a carboxy terminus and para-aminobenzyl of PAB or derivative and are cleavable under enzymatic, hydrolytic, or other metabolic conditions. The aromatic para-amine becomes electron-donating and initiates an electronic cascade that leads to the expulsion of the leaving group by 1,6-elimination and fragmentation, which can become a free-amine antigen after elimination of carbon dioxide. In one example cathepsin B is an intracellular ubiquitous cysteine protease except in pathological conditions, such as metastatic tumors or rheumatoid arthritis. PABC and derivative conjugates produced with cathepsin B-cleavable linkers are stable in circulation. Upon cleavage of a peptide bond adjacent to the PABC, i.e., by an intracellular enzyme, the free-amine antigen is released. In another aspect, cis-aconityl amides formed with cis-aconityl anhydride can also release free-amine antigens by an electronic mechanism inspired by the hydrolysis of phthalamic acid protected amides under acidic conditions (pH 5). The 2-nitroimidazol-5-ylmethyl group may also find use in the current embodiment as a fragmenting antigen unit.

The self-immolating linkers in certain current embodiments function through reductive cleavage of linking disulfide bond that activates a trigger on the linker that causes snapback 1,4-intramolecular cyclization, carbon dioxide elimination, and release of the free antigen. One example includes a disulfide-bearing 4-mercaptopentanoate linker for antibody-maytansinoid conjugates of maytansinoids (DM1 and DM4). Other self-immolating linkers are envisioned that use disulfide cleavage in combination with a 1,6-elimination mechanism using ester or ethane-1,1-diol 4-oxymethyl-phenoxy-linked derivatives as shown below:

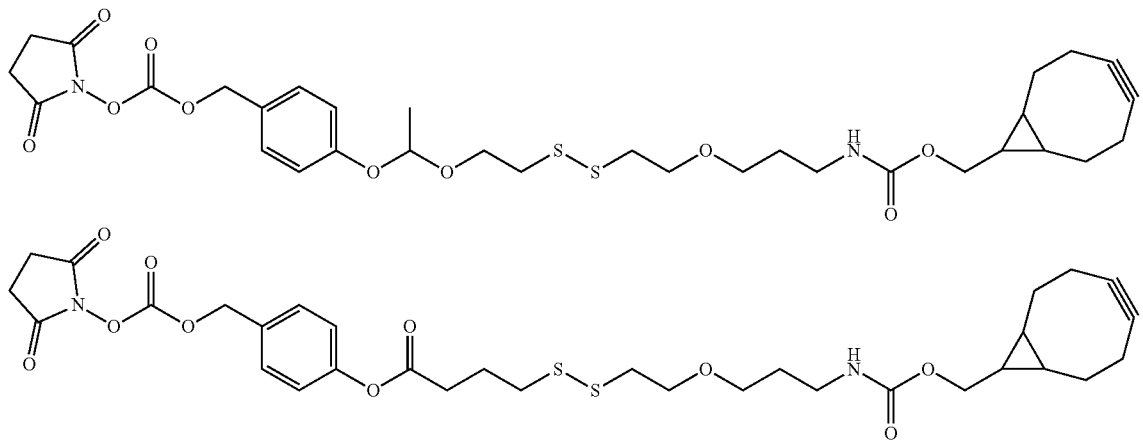

In specific aspects, the self-immolating linkers of the current invention contain functional groups that allow conjugation through stepwise reactions to link an azide functional group to an amine of an antigen.

3. Other Linkers

Without limitation to theory, the current invention also encompasses all cleavable linkers used in chemical biology classified according to their cleavage conditions by enzymes, nucleophilic/basic reagents, reducing agents, photo-irradiation, electrophilic/acidic reagents, organometallic and metal reagents, or oxidizing reagents.

IV. TLR Agonists

In some embodiments, the copolymer of formula I is operably linked to a TLR agonist. In some embodiments, the TLR agonist is a compound of general formula (VI), as described herein. In some embodiments, the TLR agonist is one known in the art and/or described herein. The TLR agonists may include an agonist to TLR1 (e.g., peptidoglycan or triacyl lipoproteins), TLR2 (e.g., lipoteichoic acid; peptidoglycan from *Bacillus subtilis, E. coli* 0111:B4, *Escherichia coli* K12, or *Staphylococcus aureus*; atypical lipopolysaccharide (LPS) such as *Leptospirosis* LPS and *Porphyromonas gingivalis* LPS; a synthetic diacylated lipoprotein such as FSL-1 or Pam2CSK4; lipoarabinomannan or lipomannan from *M. smegmatis*; triacylated lipoproteins such as Pam3CSK4; lipoproteins such as MALP-2 and MALP-404 from mycoplasma; *Borrelia burgdorferi* OspA; Porin from *Neisseria meningitidis* or *Haemophilus influenza; Propionibacterium acnes* antigen mixtures; *Yersinia* LcrV; lipomannan from *Mycobacterium* or *Mycobacterium tuberculosis; Trypanosoma cruzi* GPI anchor; *Schistosoma mansoni* lysophosphatidylserine; *Leishmania major* lipophosphoglycan (LPG); *Plasmodium falciparum* glycophosphatidylinositol (GPI); zymosan; antigen mixtures from *Aspergillus fumigatus* or *Candida albicans*; and measles hemagglutinin), TLR3 (e.g., double-stranded RNA, polyadenylic-polyuridylic acid (Poly(A:U)); polyinosine-polycytidylic acid (Poly(I:C)); polyinosine-polycytidylic acid high molecular weight (Poly(I:C) HMW); and polyinosine-polycytidylic acid low molecular weight (Poly (I:C) LMW)), TLR4 (e.g., LPS from *Escherichia coli* and *Salmonella* species); TLR5 (e.g., Flagellin from *B. subtilis, P. aeruginosa*, or *S. typhimurium*), TLR8 (e.g., single stranded RNAs such as ssRNA with 6UUAU repeats, RNA homopolymer (ssPolyU naked), HIV-1 LTR-derived ssRNA (ssRNA40), or ssRNA with 2 GUCCUUCAA repeats (ssRNA-DR)), TLR7 (e.g., imidazoquinoline compound imiquimod, Imiquimod VacciGrade™ Gardiquimod VacciGrade™, or Gardiquimod™; adenine analog CL264; base analog CL307; guanosine analog loxoribine; TLR7/8 (e.g., thiazoquinoline compound CL075; imidazoquinoline compound CL097, R848, or R848 VacciGrade™), TLR9 (e.g., CpG ODNs); and TLR11 (e.g., *Toxoplasma gondii* Profilin). In certain embodiments, the TLR agonist is a specific agonist listed above. In further embodiments, the TLR agonist is one that agonizes either one TLR or two TLRs specifically.

In some embodiments, the TLR agonist is a TLR7, TLR8, or a TLR7/8 agonist. The TLR agonist may be multiple (polymerized) molecules of the same TLR agonist or may be a mixture of linked different TLR agonists. The TLR agonist may be linked or polymerized by methods known in the art and/or described herein. In some embodiments, the compound (e.g., TLR agonist) is water soluble. Water solubility affects the shelf-life, stability, and pharmaceutical composition of the compound. Due to the structure of TLR7 and TLR8, most TLR7 and/or TLR8 agonists are poorly soluble in water. However, the compounds of Formula (I) have the advantage of water solubility.

V. Antigens

Certain aspects of the disclosure include methods and compositions concerning antigenic components including segments, fragments, or epitopes of polypeptides, peptides, nucleic acids, carbohydrates, lipids and other molecules that provoke or induce an antigenic response, generally referred to as antigens. In one embodiment, the antigen is a peptide. In particular, antigens, or antigenic segments or fragments of such antigens, which lead to the destruction of a cell via an immune response, can be identified and used in the methods and compositions described herein.

Antigens associated with various diseases and infections are known in the art. It is contemplated that any antigen may be used in the methods and compositions described herein.

Non-limiting examples of viral antigens include, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components; picornavirus antigens, such as enteroviruses, rhinoviruses, heparnavirus, cardioviruses and aphthoviruses; viral antigens derived from a pestivirus, such as bovine viral diarrhea (BVDV), classical swine fever (CSFV) or border disease (BDV); or antigens derived from a coronavirus, SARS, human respiratory coronavirus, avian infectious bronchitis (IBV), mouse hepatitis virus (MHV), and porcine transmissible gastroenteritis virus (TGEV). See, Vaccines, 6th Edition (Plotkin, Orenstein and Offit ed. 2012); Medical Microbiology 8th Edition (Murray, et al. ed. 2015) Fundamental Virology, 4th Edition, (Knipe, D. M., et al. eds. 2001) for additional examples of viral antigens.

Non-limiting examples of bacterial antigens include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; Staphylococcal antigens, such as *Staphylococcus aureus* antigens, gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: *Haemophilus influenza; Plasmodium falciparum; Neisseria meningitidis; Streptococcus pneumoniae; Neisseria gonorrhoeae*; salmonella serotype typhi; shigella; *Vibrio cholerae*; Dengue Fever; Encephalitides; Japanese Encephalitis; Lyme disease; *Yersinia pestis*; west nile virus; yellow fever; Zika virus; tularemia; hepatitis (viral; bacterial); RSV (respiratory syncytial virus); HPIV 1 and HPIV 3; adenovirus; small pox; allergies and cancers.

Non-limiting examples of fungal antigens include, but are not limited to, e.g., candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, e.g., *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components; malaria antigens such as *Plasmodium* Glutamate dehydrogenase, histidine rich protein II, lactate dehydrogenase, and aldolase.

The antigen may also be one or more of viruses (inactivated, attenuated, and modified live), bacteria, parasites, nucleotides, polynucleotides, peptides, polypeptides, recombinant proteins, synthetic peptides, protein extract, cells (including tumor cells), tissues, polysaccharides, carbohydrates, fatty acids, teichioc acid, peptidoglycans, lipids, or glycolipids, individually or in any combination thereof. The antigen may be wild-type or mutated.

The antigens used in methods and compositions described herein also include immunogenic fragments of nucleotides, polynucleotides, peptides, and polypeptides that can be isolated from the organisms referred to herein.

Live, modified-live, and attenuated viral strains that do not cause disease in a subject have been isolated in non-virulent form or have been attenuated using methods well known in the art, including serial passage in a suitable cell line or exposure to ultraviolet light or a chemical mutagen. Inactivated or killed viral strains are those which have been inactivated by methods known to those skilled in the art, including treatment with formalin, betapropriolactone (BPL), binary ethyleneimine (BEI), sterilizing radiation, heat, or other such methods.

Two or more antigens can be combined to produce a polyvalent composition that can protect a subject against a wide variety of diseases caused by the pathogens. Currently, commercial manufacturers of vaccines, as well as end users, prefer polyvalent vaccine products. While conventional adjuvants are often limited in the variety of antigens with which they can be effectively used (either monovalently or polyvalently), the compositions and methods described herein can be used effectively with a wide range of antigens, both monovalently and polyvalently. Thus, the antigens described herein can be combined in a single composition comprising the conjugates described herein.

The cancer antigen can be any type of cancer antigen known in the art. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen.

In one embodiment, the cancer antigen is a melanoma cancer antigen. Melanoma cancer antigens are useful for treating melanoma. Non-limiting exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

In some embodiments, the antigen is a malaria antigen such as *Plasmodium* glutamate dehydrogenase, histidine rich protein II, *P. falciparum* lactate dehydrogenase, fructose-bisphosphate aldolase, or circumsporozite protein (CSP). In some embodiments, the antigen is an antigenic component found in *Plasmodium* sp. Such as *P. falciparum*.

VI. APC Targeting Molecules

In some embodiments, the methods, compounds, and compositions herein relate to APC (antigen presenting cell)-targeted molecules. Typically an APC targeting molecule is one that is operatively linked to a molecule that binds to a receptor in APCs or on the cell surface of an APC. In some embodiments, the APC is a dendritic cell.

In some embodiments, the APC targeting molecule is an antibody selected from an antibody that specifically binds to MHC class I, MHC class II, CD1d, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASGPR, CLEC-6, BDCA-2, MARCO, DEC-205, mannose receptor, Langerin, DECTIN-1, B7-1, B7-2, IFN-γ receptor, IL-2 receptor, ICAM-1, Fc γ receptor, LOX-1, and/or ASPGR.

In some embodiments, the APC targeting molecule is a mannose, glucosamine, or galactosamine. In some embodiments, the APC targeting molecule is a lectin.

VII. Pharmaceutical Compositions

Embodiments include methods and compositions for increasing immune responses in a subject in need thereof. They include compositions that can be used to induce or modify an immune response against an antigen, e.g., a polypeptide, a peptide, a carbohydrate, a lipid or other molecule or molecular fragment and against developing a condition or disease associated with such antigen.

Administration of the compositions will typically be via any common route. This includes, but is not limited to oral, parenteral, orthotopic, intradermal, subcutaneous, intramuscular, intraperitoneal, intranasal, by inhalation, by using a nebulizer, or by intravenous injection. In certain embodiments, a vaccine composition may be inhaled (e.g., U.S. Pat. No. 6,651,655, which is specifically incorporated by reference). Additional formulations, which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Typically, compositions are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. In some embodiments, the compositions are lyophilized. In some embodiments, the composition is a water-based composition (i.e., aqueous). In some embodiments, the composition does not comprise an emulsion.

The manner of application may be varied widely. Any of the conventional methods for administration of an antibody are applicable. These are believed to include oral application on a solid physiologically acceptable base or in a physiologically acceptable dispersion, parenterally, by injection and the like. The dosage of the pharmaceutical composition will depend on the route of administration and will vary according to the size and health of the subject.

In many instances, it will be desirable to have multiple administrations of at most about or at least about 2, 3, 4, 5, 6, 7, 8, 9, 10 or more. The administrations may range from 2 day to twelve week intervals to six month intervals or longer, more usually from one to two week intervals. The course of the administrations may be followed by assays for reactive immune responses and T cell activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The compounds can be formulated for parenteral administration, e.g., formulated for injection via the intravenous, intradermal, intramuscular, subcutaneous, or even intraperitoneal routes. The preparation of an aqueous composition that contains compounds and/or polymers of the current disclosure that modifies the subject's immune condition will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form is preferably sterile and preferably fluid to the extent that it may be easily injected. It also should be stable under the conditions of manufacture and storage and is preferably preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

VIII. Therapeutic Applications

Aspects of the disclosure relate to a method for inducing the immune system comprising administering a compound, copolymer, or composition of the current disclosure. Further aspects relate to a method for preventing or treating an infection comprising administering a compound, copolymer, or composition of the current disclosure. Further aspects relate to a method for preventing infectious disease or treating cancer in humans, comprising administering a compound, copolymer, or composition of the current disclosure.

The methods, compounds, and compositions described herein can be used to treat or prevent a variety of diseases. In specific embodiments, the methods and compositions are used in vaccines to prevent illness from common infectious agents or to prevent cancer. More specifically, in certain embodiments the compositions are used as an adjuvant. Methods and compositions described herein may be used to treat cancerous tumors of all types, locations, sizes, and characteristics. For example, the methods and compositions may be used to treat a cancer such as, for example, epithelial cancer (e.g., breast, gastrointestinal, lung), prostate cancer, bladder cancer, lung (e.g., small cell lung or non-small cell lung) cancer, colon cancer, ovarian cancer, brain cancer, renal cell carcinoma, pancreatic cancer, colorectal cancer, pancreatic canceracute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye Cancer, intraocular melanoma eye Cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian epithelial cancer (surface epithelial-stromal tumor), ovarian germ cell tumor, ovarian low malignant potential tumor, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

Non-limiting examples of infectious diseases that can be prevented or treated by the methods described herein include anthrax, cervical cancer (human papillomavirus), diphtheria, hepatitis A, hepatitis B, *Haemophilus influenzae* type b (Hib), human papillomavirus (HPV), influenza (Flu), japanese encephalitis (JE), lyme disease, Zika, malaria, measles, meningococcal, monkeypox, mumps, pertussis, pneumococcal, polio, rabies, rotavirus, rubella, shingles (herpes zoster), smallpox, tetanus, typhoid, tuberculosis (TB), varicella (Chickenpox), yellow fever, HIV/AIDS, giardiasis, infectious mononucleosis, pneumonia, rocky mountain spotted fever, salmonella infections, severe acute respiratory syndrome, shingles, toxic shock syndrome, hepatitis C, West Nile virus, sexually transmitted diseases, including gonorrhea, chlamydia, and syphilis, and the like.

It is also contemplated that the methods and compositions described herein may be used to treat or prevent certain types of cancer including but not limited to an epithelial cancer, (e.g., breast, gastrointestinal, lung), prostate cancer, bladder cancer, lung (e.g., small cell lung) cancer, colon cancer, ovarian cancer, brain cancer, skin cancer, gastric cancer, renal cell carcinoma, pancreatic cancer, liver cancer, esophageal cancer, head and neck cancer, or a colorectal cancer.

IX. Examples

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1-7 Overview

Figure 4:
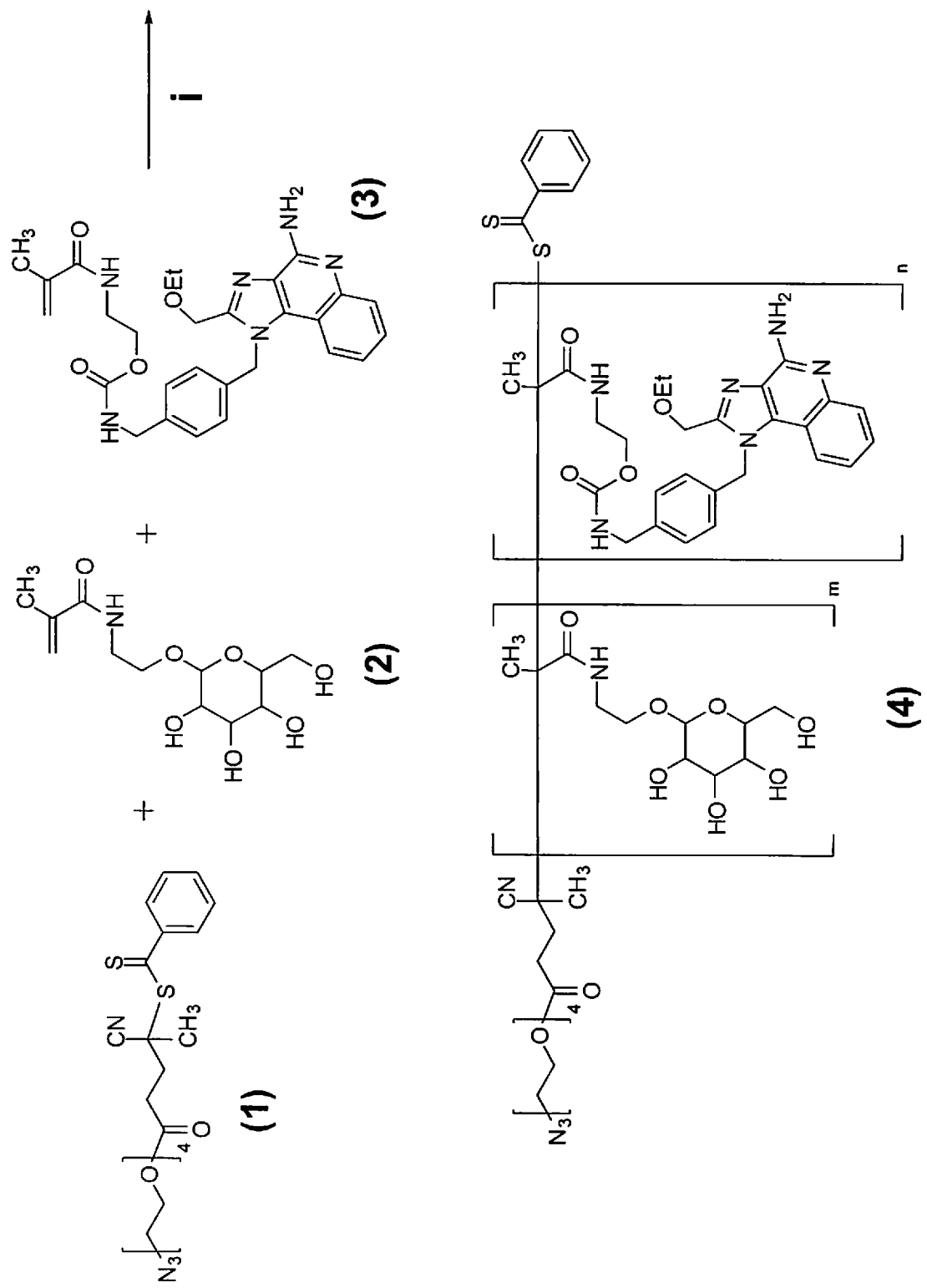
FIG. 4 shows a reaction schematic for the preparation of azide-functionalized p(Man-TLR) (4).
Figure 5:
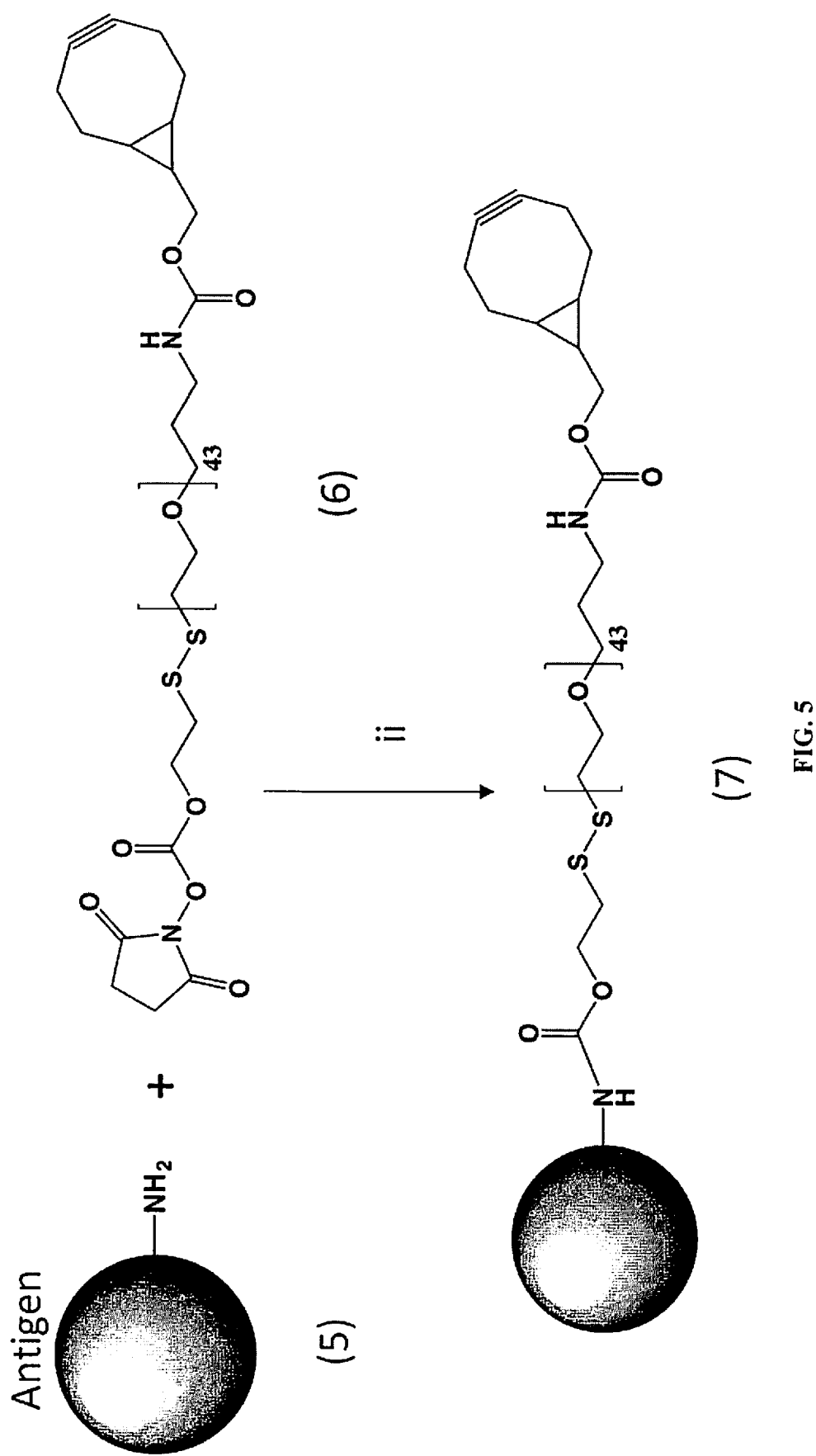
FIG. 5 show a reaction schematic for the preparation of an antigen-self-immolative linker conjugate (7).
Figure 6A:
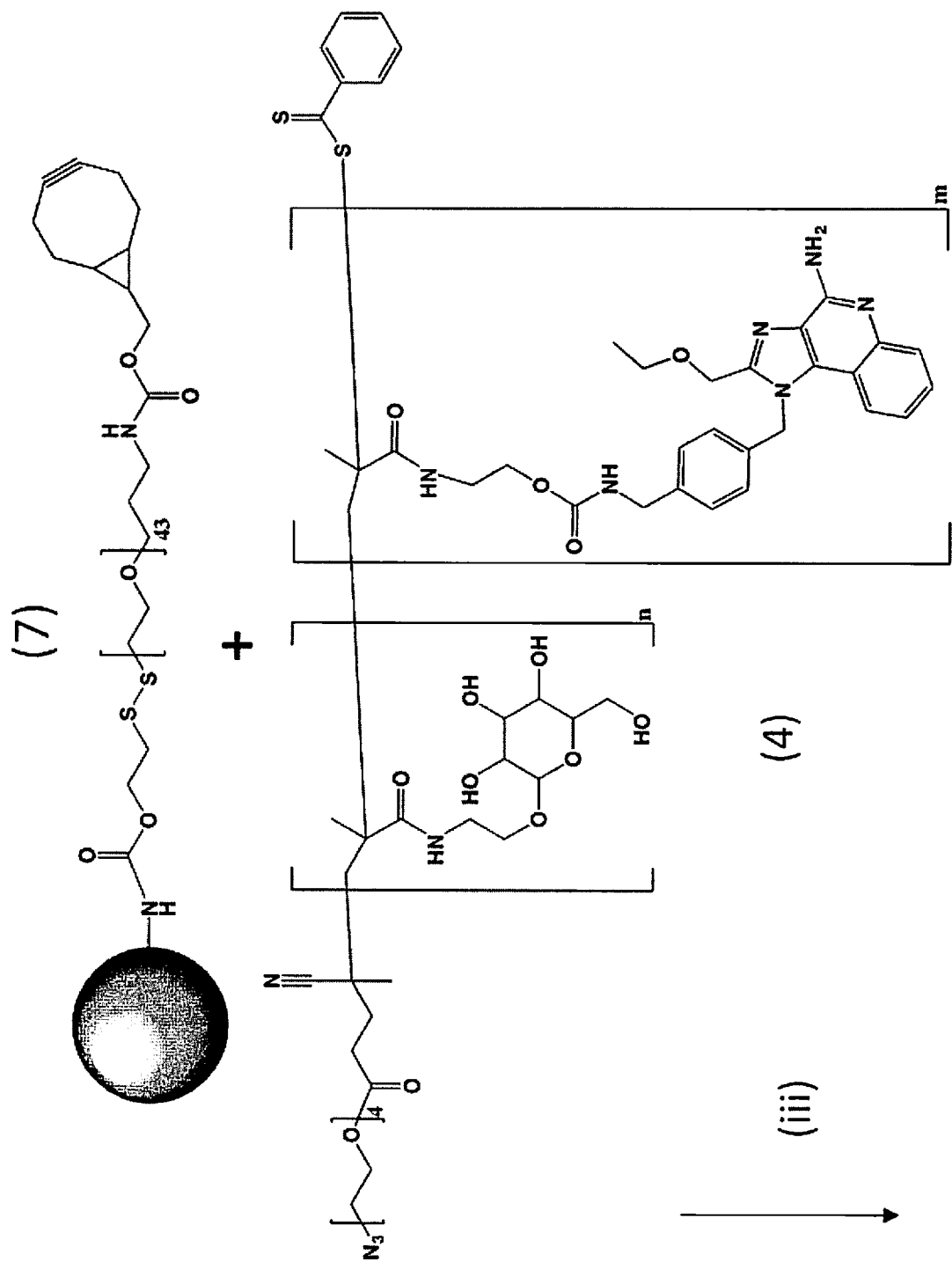
FIG. 6A-B show a reaction schematic for the preparation of antigen-p(Man-TLR) conjugate (8).
Figure 6B:
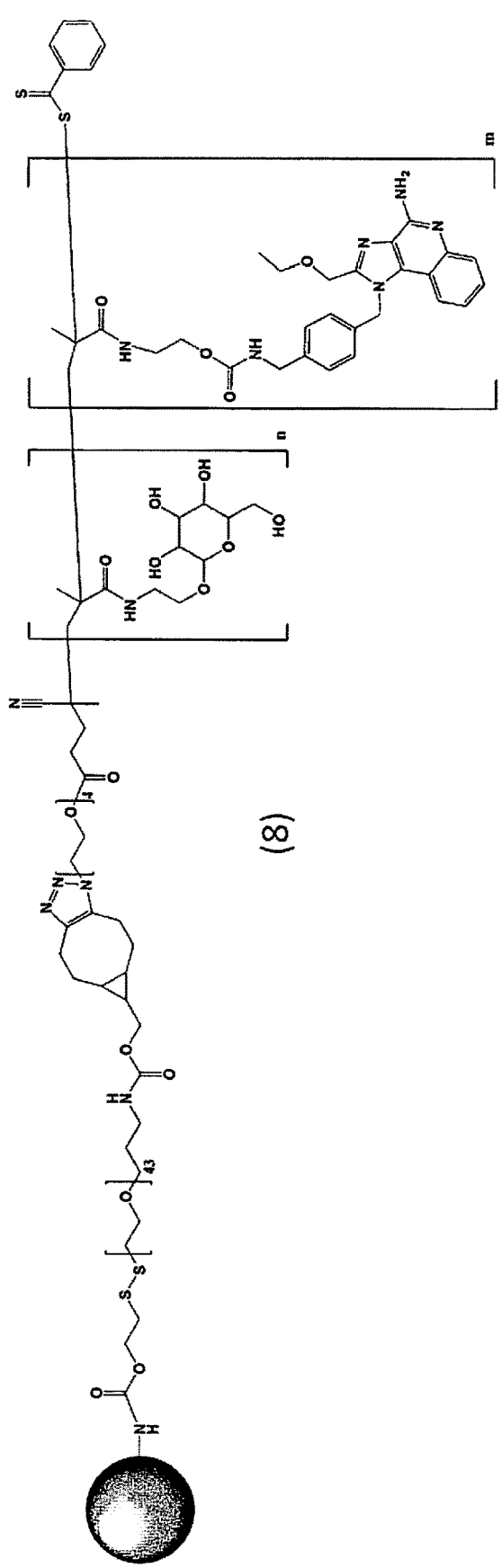
Figure 7:
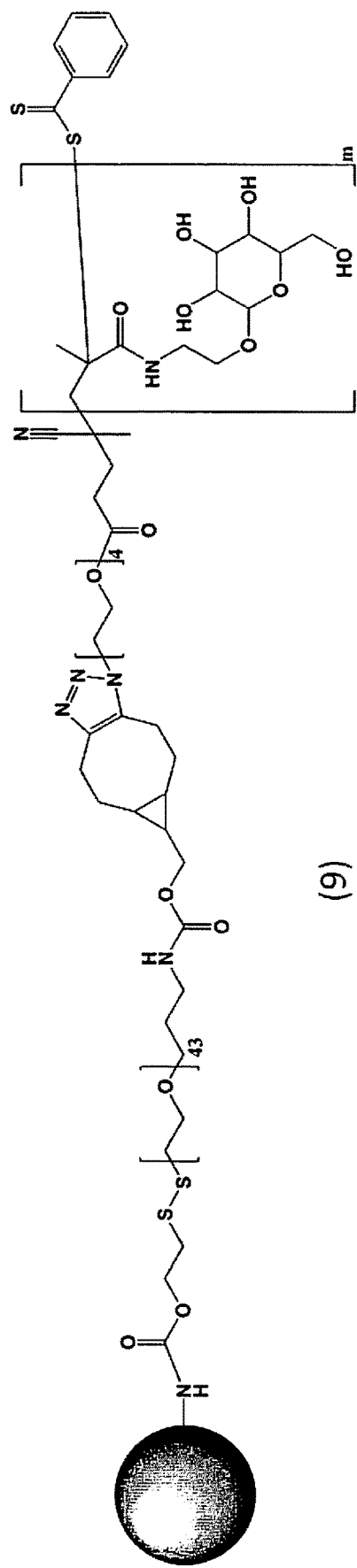
FIG. 7 shows an antigen-p(Man) conjugate (9).

As shown in FIG. 4, p(Man-TLR) (4) was synthesized from a mannose containing monomer (mannose-oxyethyl-methacrylamide (MOMA)) (2) and a second monomer that incorporates a novel TLR-7 ligand, for example TLR-7-oxyethyl-methacrylamide (TLR-MA) into structure (3). In order to tether antigens to p(Man-TLR), a bifunctional self-immolating linker was utilized that contained an amine-reactive end and a bicyclic alkyne that would react under mild conditions with the azide of (4). As shown in FIG. 5, the bifunctional linker can be conjugated to antigens (step ii), then the resulting functionalized antigen (7) can be purified and conjugated to (4). As shown in FIG. 6, antigen conjugation with (4) results in the formation of antigen-p (Man-TLR) conjugate (8). When the antigen being conjugated is the model antigen ovalbumin (OVA), the conjugate is referred to as OVA-p(Man-TLR). In addition to conjugates containing the TLR monomer, OVA-polymer conjugates prepared with a homopolymer that only contains MOMA are also disclosed, termed p(Man), as shown in FIG. 7.

Example 1: Synthesis of tert-butyl (4-(((3-amino-2-chloroquinolin-4-yl)amino)methyl)benzyl)carbamate (13)

FIG. 1 depicts the synthesis pathway to produce compound (13). 13 was prepared as shown in FIG. 1 by steps (iv) and (v). In step (iv), tert-butyl(4-(aminomethyl)benzyl)carbamate (11) (1.0 equiv) was added to a solution of dichloromethane (DCM), 2,4-dichloro-3-nitroquinoline (10) (1.0 equiv), and triethylamine (1.2 equiv.). The reaction mixture was stirred for 30 min at 45° C. The solvent was then evaporated under vacuum, and washed several times with water, then dried to yield tert-butyl (4-(((3-nitroquinolin-4-yl)amino)methyl)benzyl)carbamate (12). In step v), tert-butyl (4-(((2-methyl-3-nitroquinolin-4-yl)amino)methyl) benzyl)carbamate (12) (1.0 equiv) was added to a solution of methanol and palladium on carbon (0.1 equiv). The solution was stirred under 1 bar of hydrogen for 6 h. The reaction product was filtered and the solvent was removed under reduced pressure to yield tert-butyl (4-(((3-amino-2-chloroquinolin-4-yl)amino)methyl)benzyl)carbamate (13).

Example 2: Synthesis of tert-butyl (4-((amino-2-(ethoxymethyl)-1H-imidazo[4,5-c]quinolin-1-yl) methyl)benzyl)carbamate (16)

Compound (16) was prepared as shown in FIG. 2 by steps (vi) and (vii). In step (vi), 2-ethoxyacetyl chloride (14) (1.0 equiv) was added to a stirred solution of tert-butyl (4-(((3-amino-2-chloroquinolin-4yl)amino)methyl)benzyl)carbamate (13) (1.0 equiv), triethylamine (1.0 equiv), in DMC at 0° C. The reaction was allowed to warm to room temperature and stirred for 6 h. Solvent was removed from the reaction product under reduced pressure, and the product tert-butyl (4-((4-chloro-2-(ethoxymethyl)-1H-imidazo[4,5-c]quinolin-1-yl)methyl)benzyl)carbamate (15) was isolated via flash chromatography. In step vii), tert-butyl (4-((4-chloro-2-(ethoxymethyl)-1H-imidazo[4,5-c]quinolin-1-yl)methyl) benzyl)carbamate (15) was added to a solution of ammonia in methanol and heated at 150° C. for 1 h. The solvent was removed under reduced pressure and the product tert-butyl (4-((amino-2-(ethoxymethyl)-1H-imidazo[4,5-c]quinolin-1-yl)methyl)benzyl)carbamate (16) was isolated via flash chromatography.

Example 3: Synthesis of TLR-7-Oxyethyl-Methacrylamide(TLR-MA) (3)

Compound (3) was prepared as shown in FIG. 3 by steps (viii) and (ix). In step (viii), tert-butyl (4-((amino-2-(ethoxymethyl)-1H-imidazo[4,5-c]quinolin-1-yl)methyl) benzyl)carbamate (16) was added to an excess of trifluoroacetic acid and DCM. After 4 h, the solvent was removed under reduced pressure to give 1-(4-(aminomethyl)benzyl)-2-(ethoxymethyl)-1H-imidazo[4,5-c]quinolin-4-amine (17). In step (ix), 2-methacylamidoethyl (4-nitrophenyl) carbonate(18) (1.2 equiv) was added to a solution of 1-(4-(aminomethyl)benzyl)-2-(ethoxymethyl)-1H-imidazo[4,5-c]quinolin-4-amine (17) (1.0 equiv), and triethylamine (1.1 equiv) in DCM. The reaction was stirred for 3 h at room temperature then the solvent was removed under reduced pressure. The product TLR-MA (3) was isolated via flash chromatography.

Example 4: Synthesis of Azide-functionalized p(Man-TLR) (4)

Azide-functionalized p(Man-TLR) polymers were synthesized using reversible addition-fragmentation chain transfer (RAFT) polymerization as shown in FIG. 4 by step (i). In step (i), azide functionalized microRAFT agent (0.01 equiv.) (1), mannose-oxyethyl-methacrylamide (MEMA) (2) (0.75 equiv.), TLR-7-oxyethyl-methacrylamide(TLR-MA) (3) (0.25 equiv), and azobisisobutyronitrile (0.005 equiv.) were mixed with DMF (10 equiv.). The reaction mixture was subjected to 4 freeze-pump-thaw cycles before being heated and stirred at 70° C. for 8 h. Next, the polymer product was isolated via precipitation in acetone. After decanting the solvent portion the residual acetone was removed under reduced pressure. The polymers produced via this protocol have an average molecular weight of 34.3 kDa and contain 16% TLR-MA monomers and 84% MEMA monomers as determined by NMR analysis.

Example 5: Conjugation of Self-Immolative Linker (7)

Amine-containing antigens (5) can be easily conjugated to a bifunctional-PEG linker that contains an amine-reactive group and a bicyclic-octyne. Compound (7) was synthesized as shown in FIG. 5 by step (ii). An amine-containing antigen, i.e., ovalbumin (OVA) (1.0 equiv.) was added to a pH 7.8 phosphate buffer containing (6) (10.0 equiv.) and stirred at room temperature for 1 h. The product antigen-self-immolative linker conjugate (7) was isolated via size exclusion chromatography.

Example 6: Copper-Free Click Conjugation of Modified Amine with p(Man-TLR) (8)

Modified antigens can be conjugated to p(Man-TLR) under mild conditions in the absence of catalyst. When the antigen conjugated to the polymer is OVA, these conjugates, referred to as OVA-p(Man-TLR), were synthesized as shown in FIG. 6 by step (iii). An antigen-self-immolative linker conjugate (7), i.e., OVA conjugated to difunctional linker (1.0 equiv) was added to a pH 7.0 phosphate buffer containing (4) (5.0 eq.) and stirred at room temperature for 1 h. The product antigen-p(Man-TLR) conjugate (8) was isolated via size exclusion chromatography.

Example 7: Antigens Tethered to Polymers that Only Contain MOMA Monomers

The reaction scheme of Example 4 can be modified by omitting the TLR-MA monomer and continuing with the synthesis as shown in Examples 5-7 to produce antigen-p (Man) conjugates (9) as shown in FIG. 7. When the antigen is OVA these conjugates are referred to as OVA-p(Man).

Example 8: Polymer Conjugate Vaccines

The two major challenges in the development of effective subunit vaccines are the ability to target unmodified recombinant protein antigens to dendritic cells (DCs) and the identification of nontoxic DC-activating adjuvants that effectively enhance the immune response to targeted antigens. In order to target antigens to DCs and simultaneously activate the targeted DCs, Applicants developed a random copolymer composed of a monomer that targets the mannose receptor (MR) on APCs and a second monomer that serves as an adjuvant by activating toll-like receptor 7 (TLR7). When conjugated to protein antigens via a self-immolate linker, the polymer, termed p(Man-TLR7), efficiently targets antigens to DCs and simultaneously induces the up-regulation of co-stimulatory molecules that are essential for effective T cell activation. Importantly, p(Man-TLR7) is a more efficient activator of DCs, as measured by the surface expression of co-stimulatory molecules and the release of proinflammatory cytokines, than the monomeric form of the TLR7 agonist used in the polymer formulation (FIG. 8). In order to test the efficacy of p(Man-TLR7)-antigen conjugates in vivo, Applicants conjugated p(Man-TLR7) to the model antigen ovalbumin (OVA) and vaccinated mice on days zero and 28 with p(Man-TLR7)-OVA conjugates or appropriate controls. After 35 days, Applicant's results show that p(Man-TLR7)-OVA conjugates improved B-cell, $CD4^+$ Tcell, and $CD8^+$ T cell responses as compared to formulations containing OVA and unconjugated p(Man-TLR7) or OVA and the monomeric TLR7 agonist used in p(Man-TLR7). Given the ability to conjugate p(Man-TLR7) to any protein antigen, this molecule has numerous applications for p(Man-TLR7)-antigen conjugates in the prevention of infectious diseases and the treatment of cancer.

Targeting antigens to surface receptors on professional antigen-presenting cells (APCs) represents an attractive method for improving antigen presentation by APCs and thus the efficacy of subunit vaccines. Delivery strategies that target antigens to APCs preferably target receptors that are abundantly expressed on the surface of APCs as well as release these antigens in their native form in intracellular compartments that contain elements of the antigen-processing machinery. The mannose receptor (MR) and other C-type lectin receptors are abundant on APCs and designed to internalize antigens, process them and display the internalized antigen on both major histocompatibility complex (MHCI and MHCII) molecules. Although targeting the MR on APCs, specifically dendritic cells (DCs), increases antigen presentation and immune response to those antigens, it is clear that additional signals, in the form of cell-activating adjuvants, are preferably combined with MR-targeting strategies for the induction of a robust sustained immune response.

The inclusion of adjuvants in subunit vaccine formulations can improve vaccine-induced protection by inducing the maturation of immature DCs, which results in the production and surface expression of proinflammatory and co-stimulatory molecules that are necessary for T cell polarization. DC activation is initiated via toll-like receptors (TLRs), which recognize pathogen-associated molecular patterns that are specific to infectious agents. Recent vaccine development has focused on incorporating TLR ligands, such as bacterial and viral DNA, bacterial proteins, and synthetic small-molecules, into the formulation of subunit vaccines. Given their relative ease of production and low toxicity, small molecule TLR-7 and TLR-8 ligands known as imidazoquinolines overcome some of the challenges of using viral and bacterial-derived material as vaccine adjuvants. However, the hydrophobicity and relatively low activity of current imidazoquinolines limits their use in vaccine formulations, and thus the design of more effective imidazoquinolines and new strategies for their delivery are greatly needed.

In order to target antigens in their native form to DCs while simultaneously delivering DC activating molecules, Applicants engineered a random copolymer that when conjugated to antigens targets these antigens to DCs via the MR, activates the targeted DC with a novel polymeric TLR-7 ligand, and releases the antigen in its unmodified form via intracellular-specific stimuli. When the antigen being conjugated is the model antigen ovalbumin (OVA), the conjugate is referred to as OVA-p(Man-TLR).

Figure 8A:
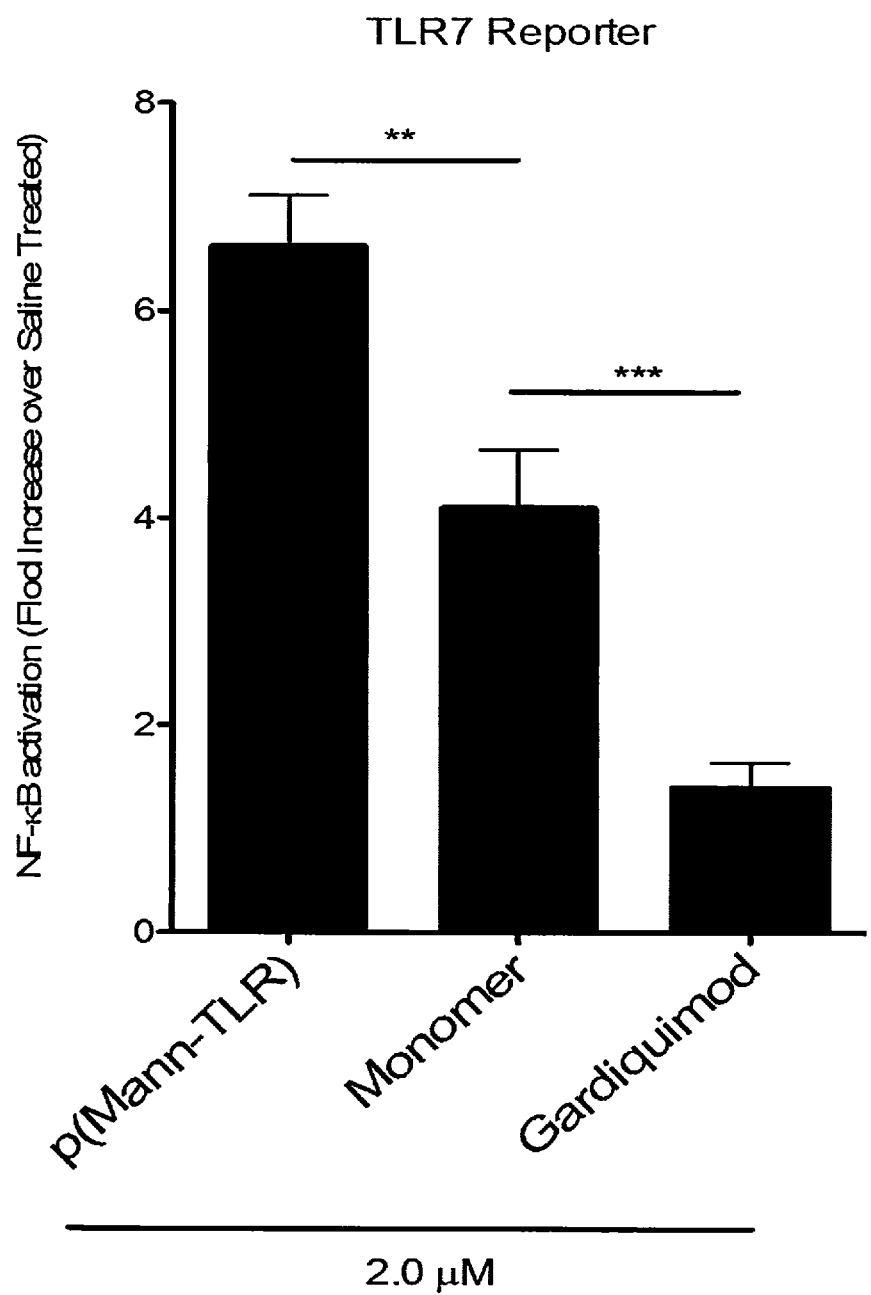

In order to demonstrate that incorporating TLR ligands into a polymeric construct increases their efficacy, Applicants treated HEK-Blue TLR7-activation reporter cells with media that contained 2.0 µM of a known TLR-7 agonist, gardiquimod, 2.0 µM of TLR7-MA, or an amount of p(Man-TLR) such that the media contained 2.0 µM of TLR7-MA in polymeric form. After 12 h, the cells were analyzed for TLR7 activation. The results show that p(Man-TLR) is a more efficient TLR-7 agonist as compared to TLR7-MA and gardiquimod (FIG. 8A). Treating cells with p(Man-TLR) resulted in a nearly 7-fold increases in TLR7 activation as compared to treating cells with the TLR-MA or gardiquimod, which initiated a 4- and almost 2-fold increase in TLR-7 activation, respectively.

Given that DCs are the primary target for the polymer-conjugates, Applicants treated bone marrow derived dendritic cells (BMDCs) with various concentrations of TLR7-MA, p(man-TLR), or the synthetic oligonucleotide CpG, a powerful TLR-9 agonist. After 6 hours, the cells were stained for the upregulation of the co-stimulatory molecules CD80 and CD86 and analyzed for the surface-expression of these molecules via flow cytometry. The results, shown in FIG. 8A-B, demonstrate that, at concentrations from 0.01 µl\4 to 1.0 µM, p(Man-TLR) increases the amount of CD80 and CD86 on BMDCs as compared to TLR7-MA. Although CpG outperforms both p(Man-TLR) and TLR7-MA at concentrations below 1.0 µM, at 1.0 µM p(Man-TLR) is equally effective as CpG in increasing the surface expression of CD80 and CD86. Importantly, the toxicity of CpG when used at 10 µM made it impossible to collect data at this concentration. However, cells treated with 10 µM p(Man-TLR) or 10 µM TLR7-MA showed no significant decrease in viability as compared with cells treated with lower concentrations of these compounds.

In addition to the upregulation of co-stimulatory molecules, effective adjuvants preferably also increase the production of proinflammatory cytokines by DCs. Thus, BMDCs were treated with various concentrations of TLR7-MA or p(Man-TLR) then the cell media were analyzed for the concentration of IL-12p70, IL-6, and TNFα via ELISA (FIG. 8D-F). Again, p(Man-TLR) is a more effective activator of BMDCs as evidenced by the increased production of proinflammatory cytokines. BMDCs treated with media containing 1.0 µM of p(MAN-TLR) produced 5-fold more IL-12p70, 3-fold more IL-6 and 6-fold more TLRα as compared to cells treated with 1.0 µM of TLR7-MA. These results, in concert with the results demonstrating that p(Man-TLR) is a more efficient upregulator of co-stimulatory molecules, demonstrate that incorporating TLR7 ligands into polymeric structures increases their ability to activate dendritic cells, an important factor in vaccine efficacy.

It is contemplated that conjugating p(Man-TLR) to antigens will improve their uptake by DCs and increased DC activation. To demonstration that p(Man-TLR) is able to target DCs, mice were treated with an i.d. injection of fluorescently labeled Ovalbumin (fOVA) as either free fOVA, fOVA-pMan, or fOVA-p(Man-TLR). After 12 h, the lymph node resident DC subsets of these animals were analyzed for fOVA. DCs from animals treated with fOVA-p(Man-TLR) took up significantly more OVA as compared to DCs from animals treated with fOVA. More than twice as many CD8+ cross presenting DCs in animals treated with fOVA-p(Man-TLR) were fOVA positive as compared to animals treated with fOVA (FIG. 9A). Conjugating fOVA to p(Man-TLR) induced a 3-fold increase in the number of CD4 activating DCs that were positive for fOVA as compared to the same DC subset in mice treated with fOVA (FIG. 9B). fOVA-p(Man-TLR) was also able to target both double negative DCs and dermal conventional DCs as compared to free fOVA (FIG. 9C-D). These results are a clear indicator that OVA-p(Man-TLR) is more efficiently taken up by DCs as compared to free OVA.

Given the ability of p(Man-TLR) to activate BMDCS and target tethered proteins to various DC-subsets, mice were treated with OVA-p(Man-TLR) and the OVA-specific immune response was analyzed. Animals were treated on day 0 and 28 with an i.d. injection of OVA-p(Man-TLR), OVA-p(Man)+TLR7-MA, OVA and unconjugated p(Man-TLR), p(Man-TLR), or OVA+CpG. Mice receiving formulations that contained either free or polymer-conjugated OVA were treated with 10 µg of OVA on days 0 and 28. Mice treated with formulations containing either TLR7-MA or p(man-TLR) either free or OVA conjugated received 30 µg of TLR7-agonist as TLR7-MA or the total weight of TLR7-MA monomer units in the polymer on days 0 and 28. Mice treated with OVA and CPG received 30 µg of CPG on days 0 and 28. After 35 days, the lymphocytes from the spleen and lymph node were harvested and restimulated with either whole OVA or the CD8 immunodominant peptide SIINFEKL. After restimulation, lymphocytes taken from mice treated with OVA-p(Man-TLR) had significantly more IFNγ+CD4+ T cells as compared to mice receiving other treatments (FIG. 10A). Vaccinating mice with OVA-p(Man-TLR) also increased the number of IFNγ+CD8 T cells in the lymph nodes as compared to mice treated with OVA-p(Man) and TLR7-MA and mice treated with OVA and CpG (FIG. 10B). Restimulation of the splenocytes and subsequent FACS analysis revealed that OVA-p(Man-TLR) significantly increased the number of CD8+ and CD4+ T cells that are positive for TNFα as compared to other formulations containing either TLR7-MA or p(Man-TLR) (FIG. 10C-D). Here, Applicants show that OVA-p(Man-TLR) induces a more robust T cell response than both OVA-p(Man-TLR)+ TLR7-MA and OVA administered with unconjugated p(Man-TLR). This result demonstrates that both the ability to target OVA to DCs and the increased DC activation that results from incorporating the TLR7 agonist into the polymer are central to the improved efficacy of OVA-p(Man-TLR).

Figure 11E:
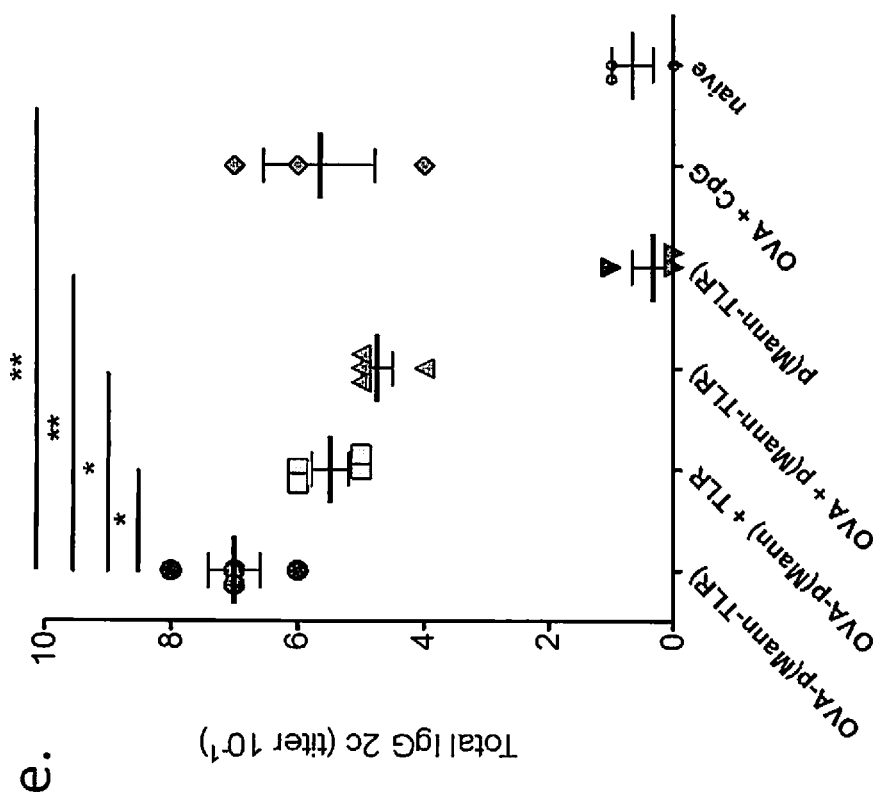

In order to initiate protection against extracellular microorganisms and to prevent the spread of intracellular infections, effective vaccines preferably induce a strong humoral immune response. The ability of OVA-p(Man-TLR) to mount an effective humoral immune response was analyzed by determining the percentage of T follicular helper (Tfh) cells in the LN and spleen, the number of antigen specific plasma cells in the spleen, and the OVA specific antibody titers of vaccinated mice. The results show that on day 35, following vaccination on days 0 and 28, OVA-p(Man-TLR) significantly increases the percentage of Tfh in the lymph node and spleen as compared to other treatments (FIGS. 11A-B). Not surprisingly, this increase in Tfh cells resulted in an increase in the number of OVA-specific IgG-producing plasma cells. As shown in FIG. 11C, vaccination with OVA-p(Man-TLR) results in a more than 2-fold increase in the number IgG-producing plasma cells as compared to mice treated with OVA+p(Man-TLR) or other formulations containing TLR7-MA or p(Man-TLR). Given these impressive results, we analyzed the blood of vaccinated animals for total OVA-specific IgG titers as well as OVA-specific IgG2C titers. These results show that OVA-p(Man-TLR) induces a significant increase in both total IgG and IgG2C titers as compared to other vaccine formulations. These results demonstrate that OVA-p(Man-TLR) induces a robust humoral immune response as compared to the other formulations tested. Again, the ability of OVA-p(Man-TLR) to induce a superior humoral response compared to OVA-p(Man)+TLR and OVA+p(Man-TLR) highlights the importance of targeting antigens to DC in combination with polymerized TLR7 agonists.

Example 9: APC Activation of Polymer Conjugates with TLR7 Compared to Unconjugated TLR7 (mTLR7)

Figure 12:
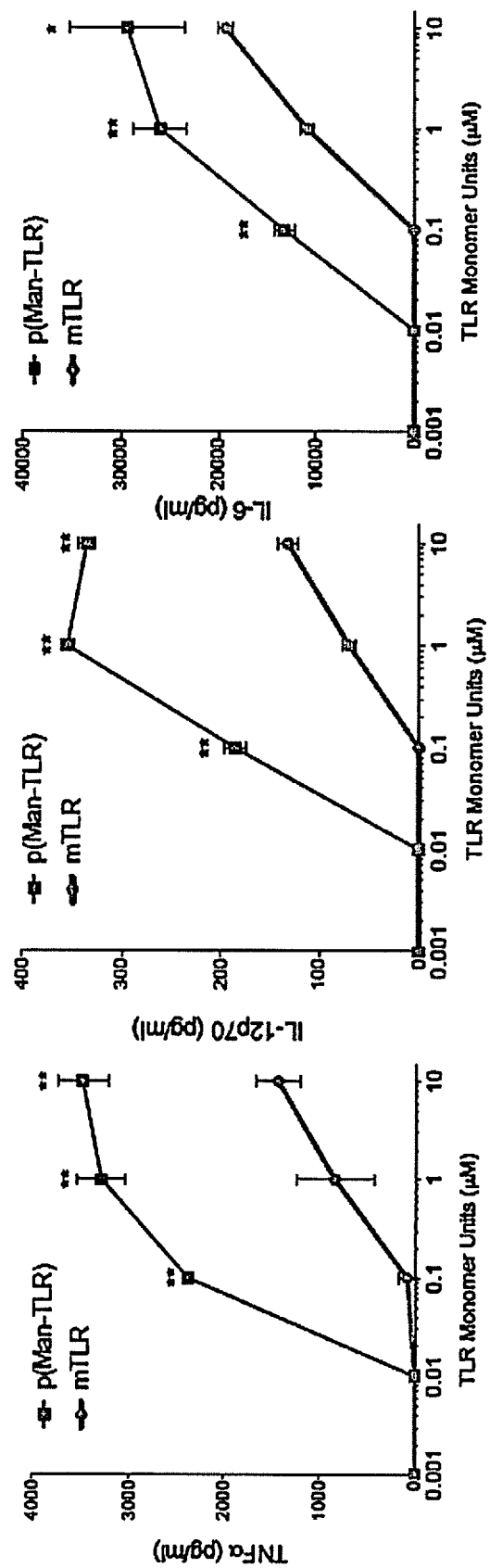
FIG. 12 shows that, in vitro, the p(Man-TLR) (i.e., the polymer that bears both mannosylation and TLR agonist conjugation) activates bone marrow-derived DCs much more potently than the monomeric form of the same TLR agonist on a dose-equivalent basis.

To demonstrate that incorporating TLR7 ligands into a polymer that targets the mannose receptor on antigen presenting cells (APCs) increases cellular activation as compared to the free TLR7 agonist, bone marrow derived dendritic cells (BMDCs) were treated with equal amounts of free TLR7 ligand (mTLR) or the same TLR7 ligand polymerized into p(Man-TLR). BMDCs were treated with media containing various concentrations (0.001 to 10 $\mu$M) of free TLR7 ligand (i.e., mTLR) or the same molar amount of TLR7 ligand incorporated into p(Man-TLR). After 24 hours, the media was collected from the BMDCs and assayed for the presence of the proinflammatory cytokines IL-12p70, IL-6 and TNF-$\alpha$ via ELISA. The results showed that at a concentration of 0.01 $\mu$M and above p(Man-TLR) induces more cellular activation than free mTLR7 agonist. (FIG. 12). At a TLR7 agonist concentration of 0.01 $\mu$M and above, p(Man-TLR) induces more production of the proinflammatory cytokines IL-12p70, IL-6 and TNF-$\alpha$ as compared to the equivalent concentration of free mTLR7 agonist. These results demonstrate that incorporating a TLR7 ligand into our polymeric formulation, p(Man-TLR), increases the TLR's ability to activate APCs and thus improves its efficacy as an adjuvant.

Example 10: Antigen Delivery and APC Activation

Figure 13:
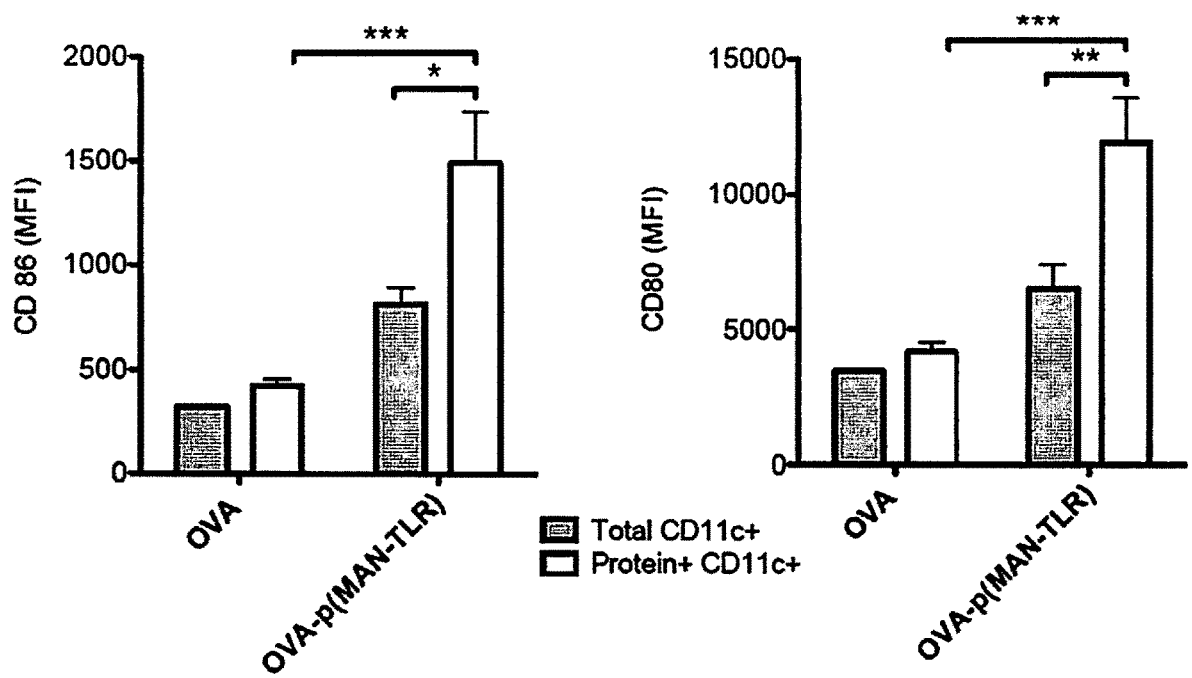
FIG. 13 shows that, in vivo, 24 hr after foot pad injections, DCs resident in the dLN remain strongly activated by the Ag-p(Man-TLR7) polymeric formulation, as indicated by expression of the co-stimulatory molecules CD86 and CD80. Activation is highest in DCs that collect the formulation and thus are also antigen-positive. Thus, both antigen and adjuvant are co-delivered to the same DCs, which are then the cells that are activated. This is one of the benefits of selecting TLR7 as an adjuvant target, based on its intracellular, endosomal localization.

In order to be an effective adjuvant/delivery system for vaccine development, p(Man-TLR) conjugates preferably target antigens to APCs and activate these cells in vivo. Mice were injected in the footpads with 50 $\mu$g of fluorescently-labeled OVA conjugated to p(Man-TLR) or free non-conjugated fluorescently-labeled OVA. After 24 h, the draining lymph nodes of these animals were collected and processed into single cells suspensions. The lymphocytes were then analyzed via flow cytometry for the presence of the co-stimulatory molecule markers CD86 and CD80 on APCs. The results show that DCs (i.e., CD11c+ cells) taken from the lymph nodes of mice treated with OVA-p(Man-TLR) express significantly more CD80 and CD86 as compared to mice treated with free OVA (FIG. 13). Furthermore, CD11c+ cells that had taken up OVA-p(Man-TLR) conjugates (i.e., Protein+CD11c+ cells) had higher levels of expression of CD80 and CD86 as compared to the expression of CD80 and CD86 on the total CD11c+ population of mice treated with OVA-p(Man-TLR). This result demonstrates that conjugating p(Man-TLR) induces activation of the DCs that are targeted by OVA-p(Man-TLR).

Example 11: In Vivo Immune Response after Vaccination

Figure 14:
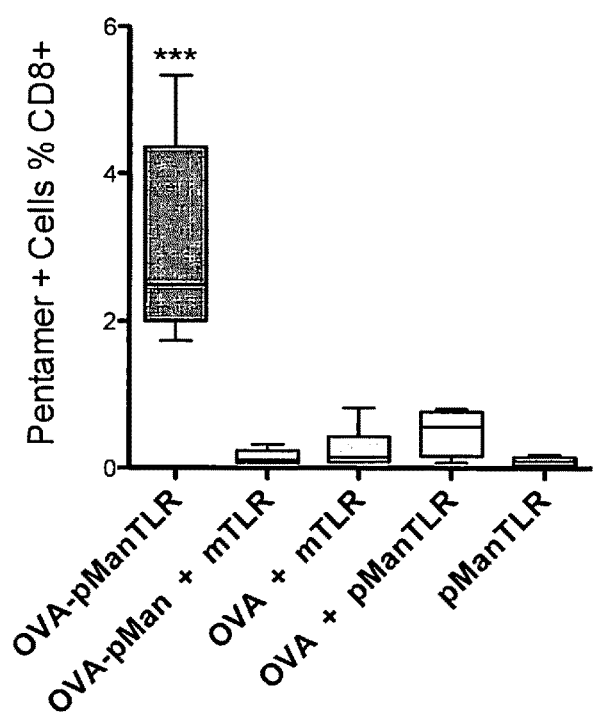
FIG. 14: Mice were vaccinated at day 0 and day 28 with 10 µg OVA equivalent of the various forms and combinations shown, and were sacrificed on day 35 for analysis. The intensity of the CD8+ T cell response was judged by measuring the frequency of SIINFEKL (SEQ ID NO. 1) pentamer-binding cells. As can be seen from the figure, the full OVA-p(Man-TLR) formulation form generated a much stronger response than did the various component parts, including OVA+p(Man-TLR), i.e., the vaccine without conjugation of the antigen to the polymer chain.
Figure 15:
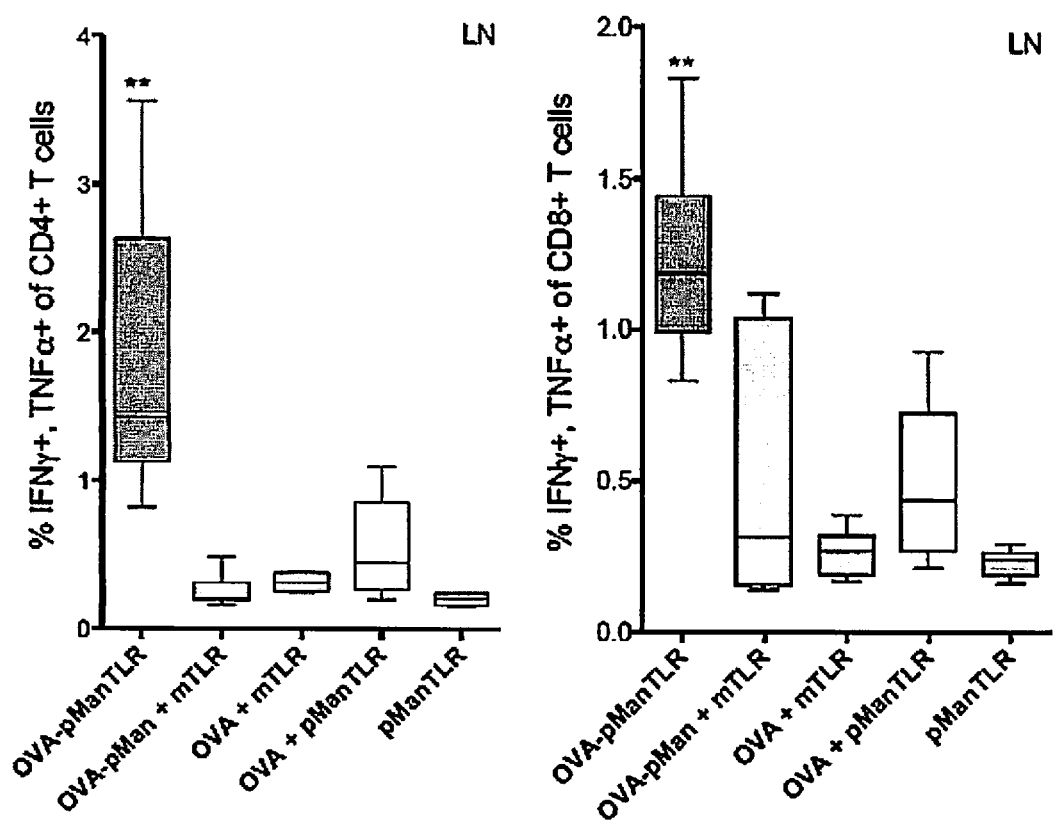
FIG. 15: Mice were vaccinated at day 0 and day 28 with 10 µg OVA equivalent of the various forms and combinations shown, and were sacrificed on day 35 for analysis. The cytokine responsiveness of cells in the LN was determined after antigen re-exposure. The most potent effector T cells are polyfunctional in terms of cytokine response, here examining cells that express both IFNγ and TNFα. As can be seen from the results, the full polymer conjugate formulation OVA-p(Man-TLR) produced robust responses in both the CD4+ (left) and the CD8+ (right) T cell compartments. Separation of the formulation into its component parts was not effective: of particular note, free antigen mixed with but not conjugated to the p(Man-TLR) nanoadjuvant (OVA+pManTLR, yellow) was not nearly as effective, showing the need for the conjugate.
Figure 16:
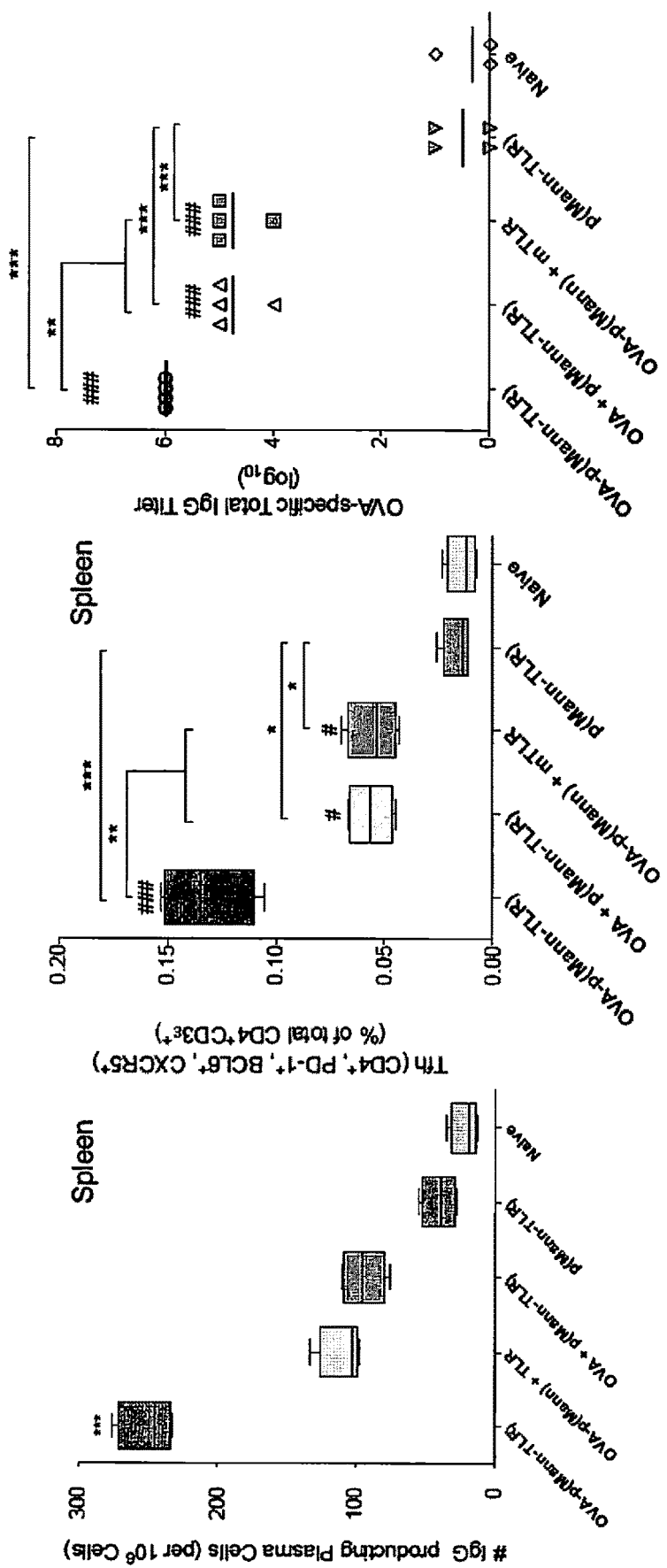
FIG. 16: The humoral response to vaccination was characterized by measuring the frequency of antibody-producing plasma cells and the frequency of Tfh cells in the spleen, and the antibody titers in the blood. As can be seen, the full polymer conjugate formulation OVA-p(Man-TLR) out-performs all other forms and combinations, including the mixture of non-conjugated antigen with the p(Man-TLR) nanoadjuvant (OVA+pMan-TLR). OVA-specific total IgG was elevated by more than an order of magnitude compared to the non-conjugate vaccine (OVA+pMan-TLR). #'s represents difference from naïve group.

Mice were vaccinated in the four footpads on day 0 and 28 with either OVA-p(Man-TLR), OVA and mTLR, OVA conjugated to p(Man) (OVA-p(Man)) and mTLR, OVA+p(Man-TLR) or just p(Man-TLR). Animals treated with formulations containing OVA received 10 $\mu$g of OVA in its free or conjugated form, and animals treated with formulations containing TLR received 30 $\mu$g of TLR in its free or unconjugated form. The animals were sacrificed on day 35 and the spleens and lymph nodes were analyzed for the resulting immune response. Our results show that mice treated with OVA-p(Man-TLR) have significantly more OVA pentamer+ cells in the lymph nodes and spleens as compared to mice receiving other therapies (FIG. 14). Additionally, upon restimulation, splenocytes for the lymph nodes of mice treated with OVA-p(Man-TLR) have significantly more CD8+ and CD4+ T cells that are positive for both the proinflammatory cytokines TNF$\alpha$ and IFN$\gamma$ as compared to restimulated splenocytes from mice receiving other treatments (FIG. 15). Finally, mice treated with OVA-p(Man-TLR) had significantly more splenic IgG producing plasma cells and T follicular helper cells as compared to the spleens of mice receiving other treatments, which resulted in significantly more OVA-specific antibodies in the blood of mice treated with OVA-p(Man-TLR) (FIG. 16).

Example 12: Comparison with Other Vaccine Formulations

Figure 17:
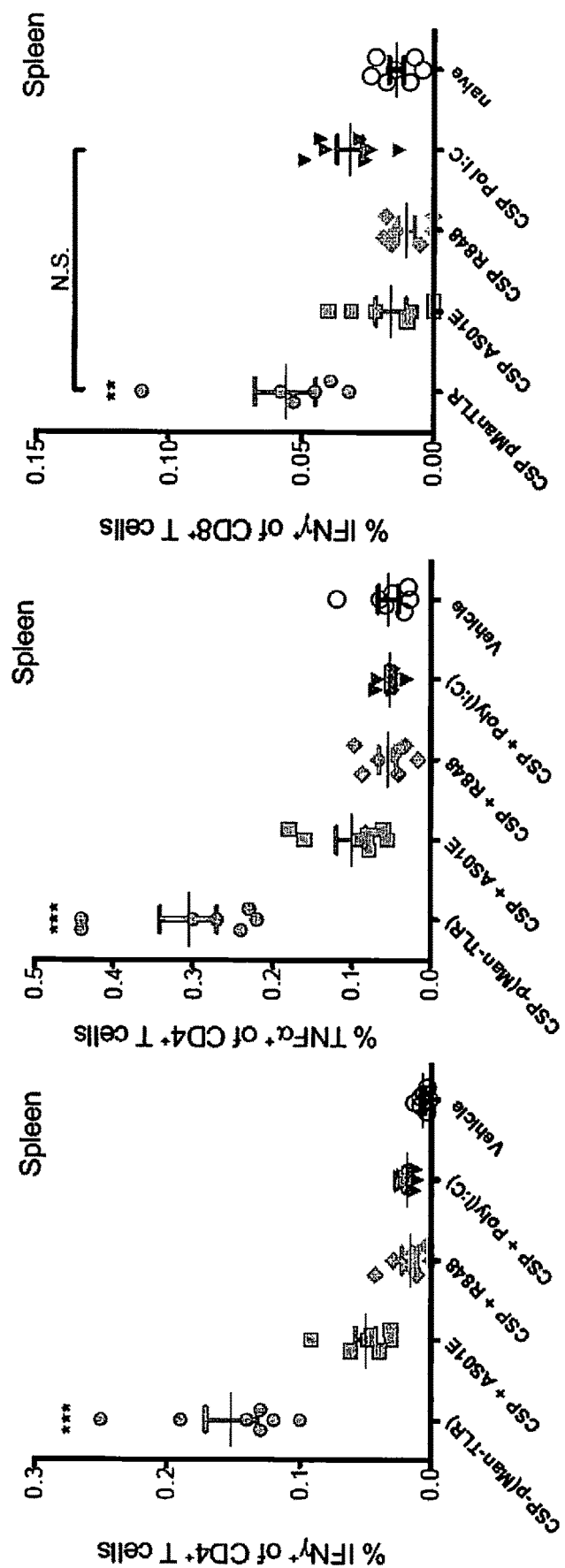
FIG. 17: To characterize the response to an actual vaccinal antigen, and to compare to an advanced clinical adjuvant, the inventors made the polymer conjugate formulation with the P. falciparum antigen CSP (the full-length protein). The inventors compared responses in the mouse to soluble CSP formulated with AS01E (a clinical adjuvant, formed from MPL-A (a TLR4 agonist) and QS21 (a saponin)), R848 (a TLR7 agonist from 3M, and poly(I:C) (a TLR3 agonist). Importantly, AS01 is the adjuvant used in the most advanced clinical malaria vaccine candidate, RTS,S, developed by GSK. Upon antigen re-exposure (to one CD8 and two CD4 peptide epitopes for 6 hr), cytokine responses were measured in the CD4+ (left, center) and the CD8+ (right) T cell compartments. As can be seen, the polymer conjugate formulation CSP-p(Man-TLR) consistently out-performed the most advanced clinical candidate (CSP+AS01E).
Figure 18:
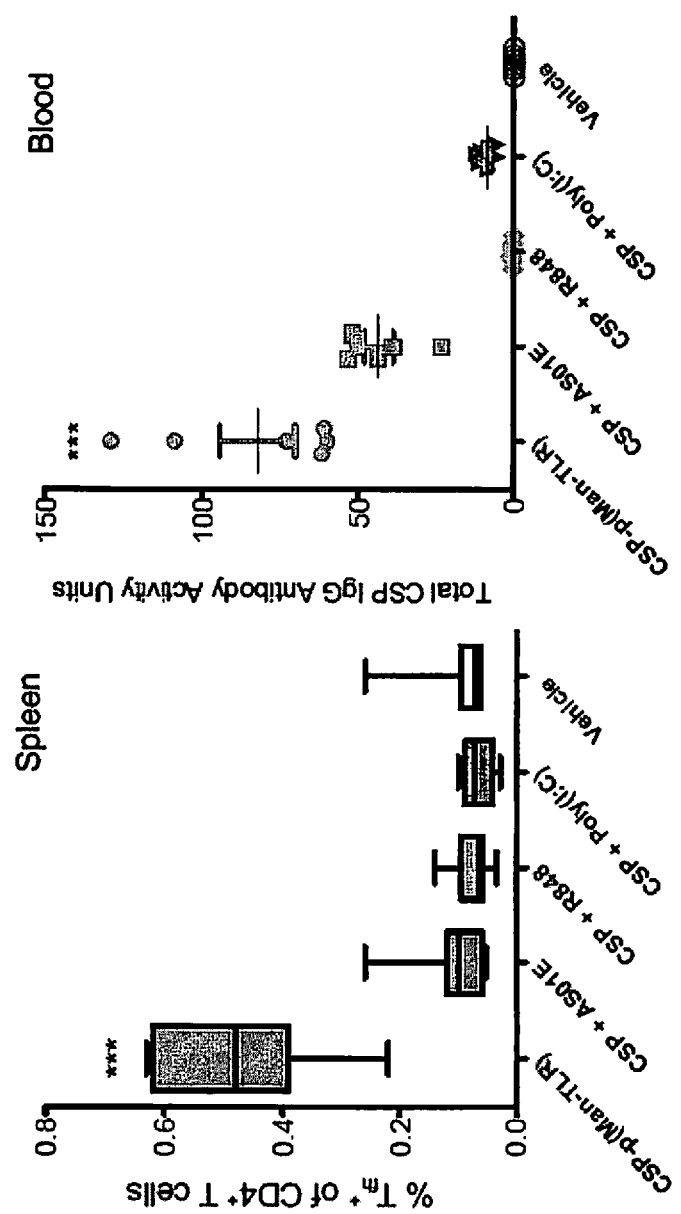
FIG. 18: To characterize humoral responses to the CSP-p(Man-TLR) polymer conjugate formulation, Tfh cells were characterized in the spleen and IgG concentrations were measured in the blood. As can be seen, the CSP-p(Man-TLR) formulation (first set of data in each graph) out-performed the most advanced clinical candidate adjuvant, AS01E (CSP+AS01E, second set of data in each graph).

The inventors benchmarked the performance of antigen-p(Man-TLR) conjugates against other vaccine adjuvant formulations that have been reported to produce effective immune responses, using a malaria antigen, specifically circumsporozite protein (CSP) from *Plasmodium falciparum*. Mice were treated on days 0 and 21 via intradermal injection into the 4 footpads with CSP-p(Man-TLR), CSP and MPLA/QS-21 liposomes (AS01E), CSP and the adjuvant R848, CSP and poly(I:C), or saline (Vehicle). AS01E is used in a clinical malaria vaccine formulation. All animals treated with formulations containing CSP received 10 $\mu$g of CSP. Animals treated with CSP-p(Man-TLR) received 20 $\mu$g TLR agonist in the polymeric form. Animals treated with AS01E received 2.5 µg of QS21. Animals treated with CSP and R848 were treated with 20 µg of R848. Animals treated with CSP and poly(I:C) received 15 µg poly(I:C). Our results show that CSP-p(Man-TLR) induces more IFNγ+ and TNFα+ cCD4+ T cells in the spleen as compared to animals receiving other therapies (FIG. 17). CSP-p(Man-TLR) also induced more IFNγ+CD8+ cells in the lymph nodes of animals treated compared to treatment with CSP and R848 and CSP and AS01E. CSP-p(Man-TLR) induced a robust humoral response. CSP-p(Man-TLR) generated more splenic T follicular helper cells and a more robust total IgG response in the blood as compared to the blood of the animals receiving other treatments (FIG. 18).

Figure 21:
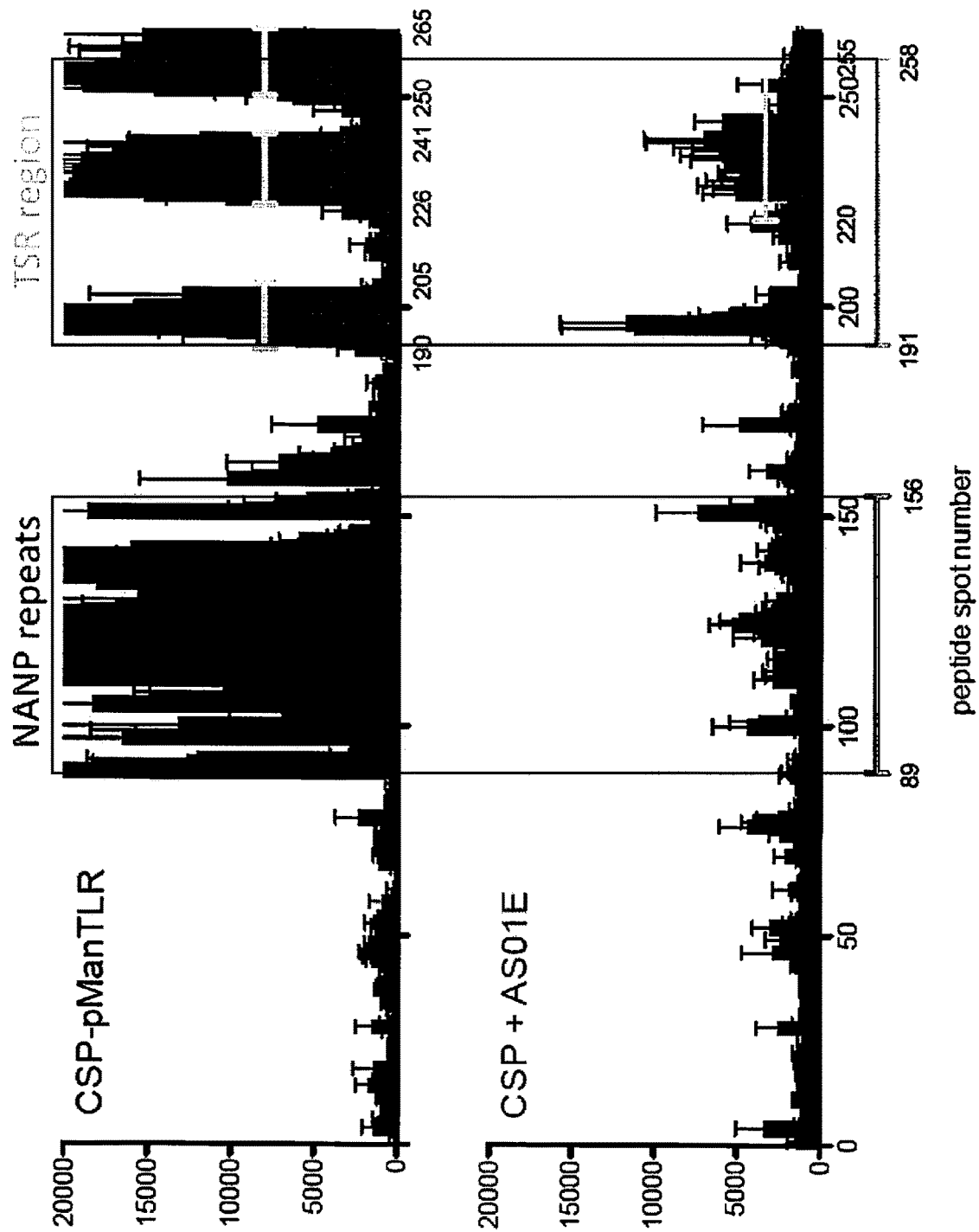
FIG. 21 shows graphical data demonstrating that the mice immunized with CSP-p(Man-TLR) mounted a broader immune response than the mice immunized with CSP+AS01E in the described experiments. The response in two major antigenic targets, namely the NANP repeat and the TSR region, where much stronger in the CSP-p(Man-TLR) formulation. To allow the responses to be compared, the two graphs are plotted on the same scale, even though several values in the plot of CSP-p(Man-TLR) are above that scale. For further comparison, the highest value in the plot of CSP+AS01E is approx. 12000 units, whereas the highest value in the plot of CSP-p(Man-TLR) is approx. 60000 units.

Of interest in addition to the quantity of the IgG response is the quality of the response, of most relevance the breadth of the response, i.e., the number of epitopic domains on the antigen against which IgGs are generated. One way to characterize this is to generate arrays of peptides from the sequence of CSP, and to measure antibodies binding to these particular peptide stretches. It was demonstrated that the GSK adjuvant AS01E generated a broader response than did resiquimod (R848) and poly(I:C) (data not shown), and very pleasingly, the CSP-p(Man-TLR) formulation induced a broader and/or qualitatively distinct IgG response than did CSP adjuvanted with a mimic of AS01E. One can see extensive coverage of domains within the NAMP repeat region and the TSR region of the CSP antigen, more so than was obtained with CSP+AS01E (FIG. 21).

The breadth of response is particularly important in response to a highly mutating virus, as in influenza. One important feature of a vaccine related to its ability to prevent disease, and especially cross-react across related serotypes such as in seasonal influenza variations, is the breadth of the antibody response. The breadth of response to CSP-p(Man-TLR) was measured and compared to CSP adjuvanted with other adjuvants, including an AS01E-like adjuvant mimicking what is used in GSK's RTS,S malaria vaccine. It was found that CSP-p(Man-TLR) yielded a broader humoral response than did CSP+AS01E or any of the other adjuvants Seasonal variations in the influenza virus lead to antigenic drift in some epitopes from season to season; when one season's vaccine response is highly broad, then there remains cellular and humoral responses to more of the next season's conserved epitopes. A broader response would likely lead to greater efficacy in the face of seasonal antigenic drift. Thus, the broader response seen by the CSP-p (Man-TLR) provides evidence for more efficacious vaccines, particularly vaccines to diseases that experience antigenic drift, such as influenza.

Example 13: In Vivo Efficacy of Cancer Vaccination

Figure 19:
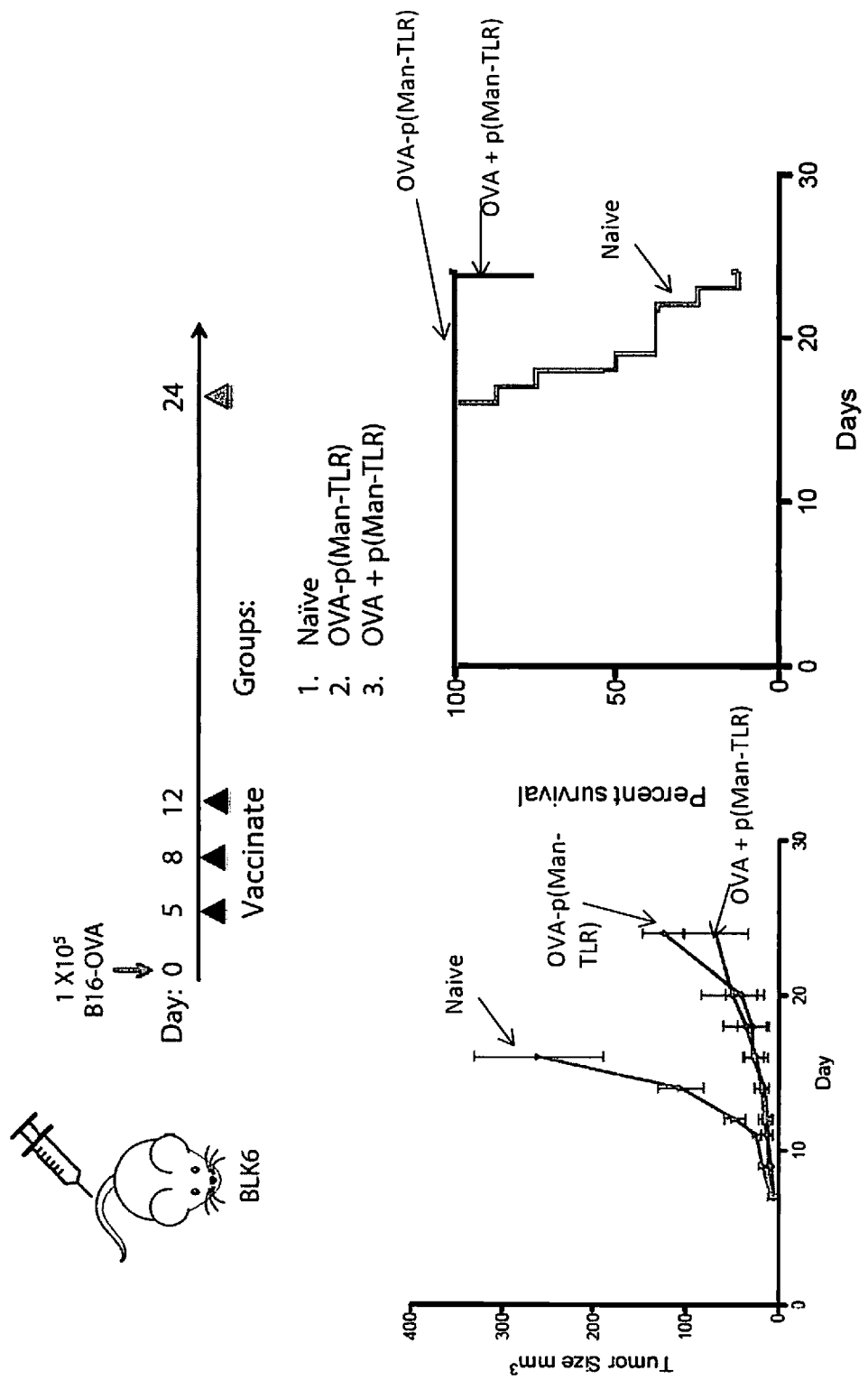
FIG. 19 demonstrates growth inhibition of tumors by OVA-p(Man-TLR) and OVA+p(Man-TLR).
Figure 20:
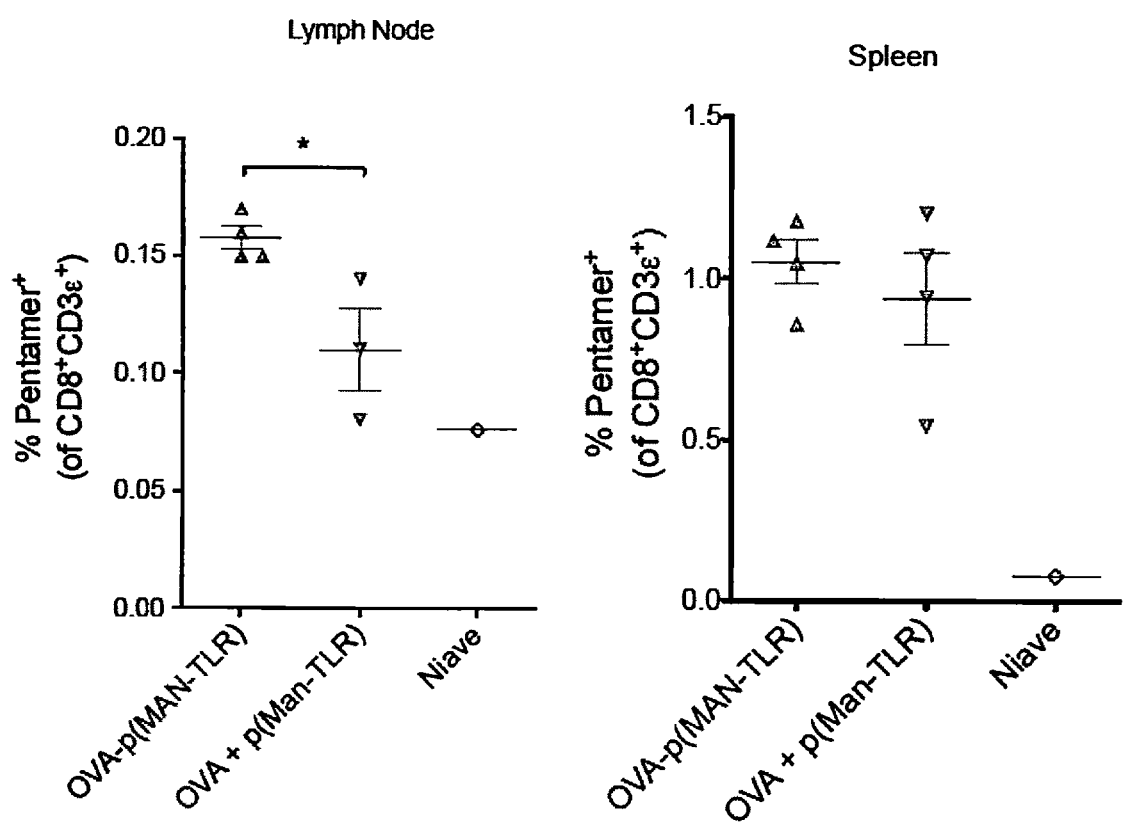
FIG. 20 shows that both OVA-p(Man-TLR) and OVA and p(Man-TLR) increased the percentage of OVA pentamer+ cells in the draining lymph nodes.

In order to determine if OVA-p(Man-TLR) conjugates could inhibit the growth of OVA-expressing tumors, mice bearing B16F10/OVA tumors (that is, B16F10 melanoma cells expressing the xeno-antigen OVA as a model tumor antigen) were treated with OVA-p(Man-TLR). $10^5$ B16F10/OVA cells were inoculated subcutaneously (s.c.) between the scapulae in C57BL/6 mice on day 0 and left to engraft and grow for 4 days. On day 4, 7, and 14, mice were administered saline or vaccinated with OVA-p(Man-TLR) or OVA and free p(Man-TLR). Animals treated with OVA received 10 µg OVA and 40 µg of TLR. The results demonstrate that both OVA-p(Man-TLR) and OVA administered with p(Man-TLR) are capable of inhibiting the growth of B16/OVA tumors (FIG. 19). Both OVA-p(Man-TLR) and OVA and p(Man-TLR) increased the percentage of OVA pentamer+ cells in the draining lymph nodes (FIG. 20). However, OVA-p(Man-TLR) induced significantly more pentamer+CD8+ cells in the draining lymph nodes as compared to animals treated with OVA+p(Man-TLR).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Any patent publication or journal publication cited herein is specifically incorporated by reference for all purposes.

The invention claimed is:

1. A copolymer comprising the structure (I):

(I) where:

A comprises at least one group that binds an Antigen Presenting Cell (APC) mannose receptor;
Z comprises at least one Toll-Like Receptor (TLR) agonist;
W and Y, are each independently a polymerized monomer unit of a polymer;
m is 10 to 150; and
p is 1 to 20;
wherein each monomer W is bound to a molecule that binds an Antigen Presenting Cell (APC) mannose receptor;
and wherein each monomer Y is bound to a TLR agonist; and
further comprising a protein antigen operatively linked to the copolymer.

2. The copolymer of claim 1, wherein A is a mannose-containing compound.

3. The copolymer of claim 1, wherein Z has the general structure (II):

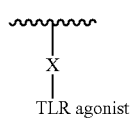

TLR agonist where X is a linker bonded to the TLR agonist and Y; and wherein X is further defined as selected from a heteroatom, an aliphatic group, a substituted aliphatic group, an alkoxy group, a heteroalkyl group, a substituted heteroalkyl group, an aryl group, a substituted aryl group, a benzyl group, a substituted benzyl group, a heteroaryl group, a substituted heteroaryl group, any combination thereof or a covalent bond.

4. The copolymer of claim 3, wherein the TLR agonist is a TLR7 agonist, a TLR8 agonist, a TLR7/8 agonist, or any combination thereof.

5. The copolymer of claim 3, wherein the TLR agonist has the general structure (III),

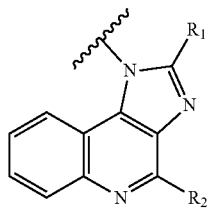

where:

$R_1$ and $R_2$ are each independently a hydrogen atom, a halogen, an alkyl group, a substituted alkyl group, a heteroalkyl group, a substituted heteroalkyl group, a cycloalkyl group, a substituted cycloalkyl group, a heterocycloalkyl group, a substituted heterocycloalkyl group, an aryl group, a substituted aryl group, a heteroaryl group, a substituted heteroaryl group, an alkoxy group, an alkoxyalkyl group, an alkoxyalkoxy group, and alkoxyalkoxyalkyl group, an amino group, or a hydroxyl group.

6. The copolymer of claim 5, wherein $R_1$ is an alkyl group or an alkoxyalkyl group.

7. The copolymer of claim 6, wherein Z is:

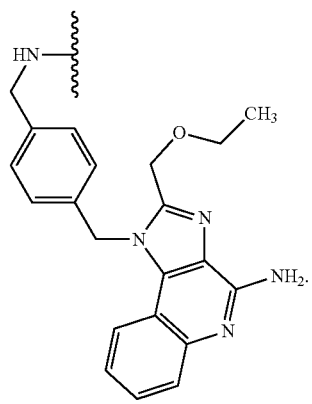 [SMILES: *NCc1ccc(Cn2c(COCC)nc3c(N)nc4ccccc4c32)cc1]

8. The copolymer of claim 1, wherein Z is:

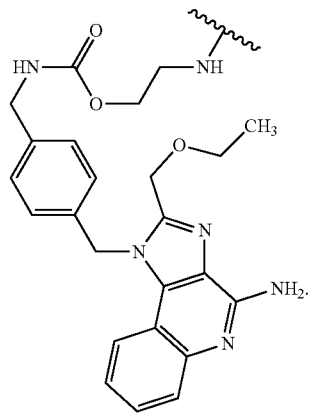 [SMILES: *NCCOC(=O)NCc1ccc(Cn2c(COCC)nc3c(N)nc4ccccc4c32)cc1]

9. The copolymer of claim 6, wherein Z is:

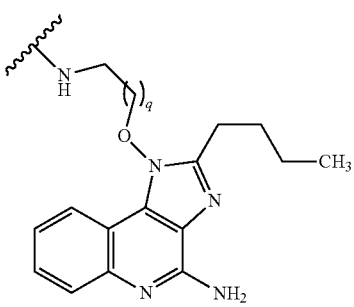

where q is 2 to 9.

10. The copolymer of claim 1, wherein the copolymer comprises end units, wherein the end units are each independently a residue of the polymer, a linker, an immunomodulating agent, or combinations thereof.

11. The copolymer of claim 10, wherein the copolymer has the general structure (IV):

(IV)

wherein E and Q are end units and each independently comprise a residue of the polymer, a linker, an immunomodulating agent, or any combination thereof; and
wherein W and Y are each independently polymerized monomer units of polyacrylate, a polyacrylamide, a saturated polyolefin, a polyamide, a peptide, a polypeptide, an unsaturated olefin formed by ring opening metathesis polymerization, a siloxane, a polysiloxane, a polyether, a polysaccharide, a polyoxazoline, a polyimine, a polyvinyl derivative or any combination thereof.

12. The copolymer of claim 11, wherein the copolymer (I) is:

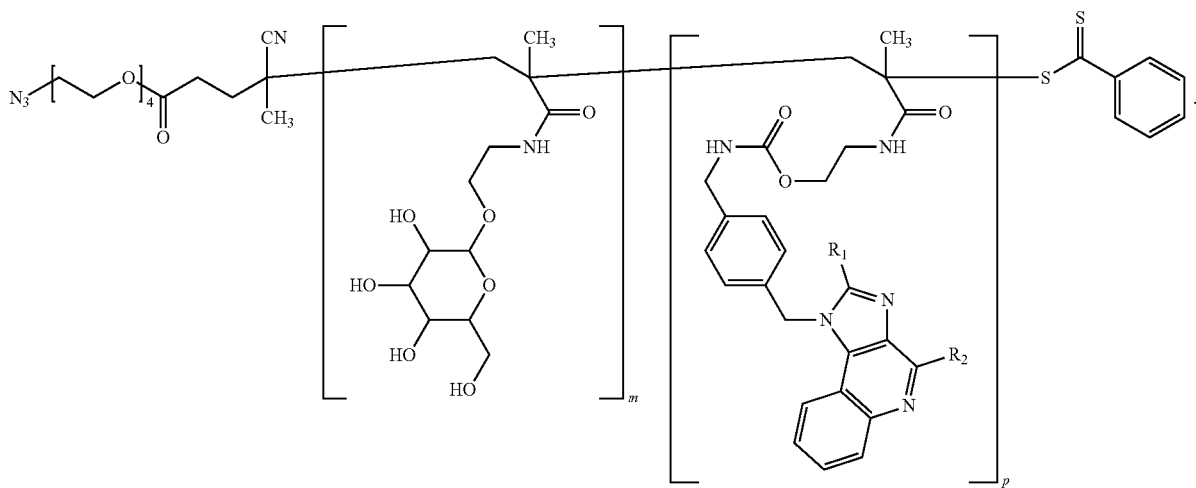

13. The copolymer of claim 11, wherein the copolymer (I) is:

where q is 2 to 9.

14. The copolymer of claim 1, wherein the copolymer is a block, alternating, random, segmented, grafted, or tapered copolymer.

15. A method for inducing the immune system comprising administering the copolymer of claim 1.

16. A composition comprising, a copolymer comprising the structure (I):

(I)

where:
A comprises at least one group that binds an Antigen Presenting Cell (APC) mannose receptor;
Z comprises at least one Toll-Like Receptor (TLR) agonist;
W and Y, are each independently a polymerized monomer unit of a polymer;
m is 10 to 150; and
p is 1 to 20;

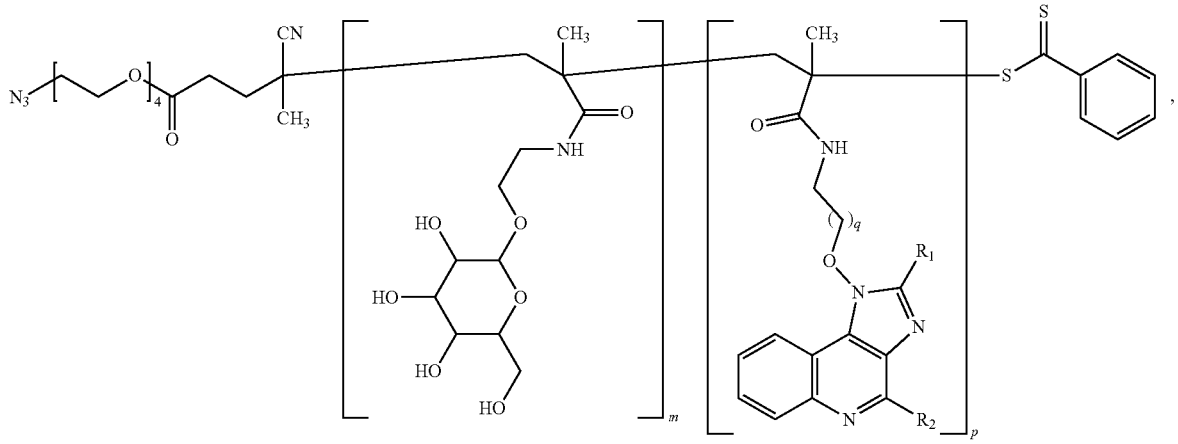

wherein the composition further comprises a protein antigen operatively linked to copolymer (I);
and wherein the protein antigen is operatively linked to the copolymer by a linker formed from:
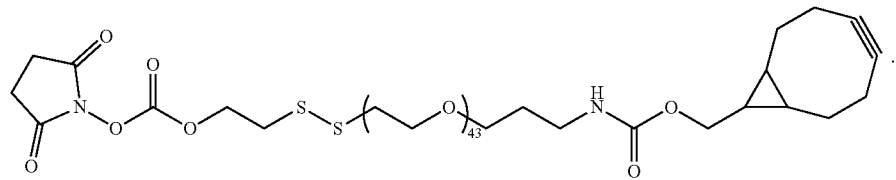
* * * * *